(12) United States Patent
Capone et al.

(10) Patent No.: US 9,649,436 B2
(45) Date of Patent: May 16, 2017

(54) ASSEMBLY METHOD FOR A FLUID PUMP DEVICE FOR A CONTINUOUS MULTI-FLUID DELIVERY SYSTEM

(71) Applicant: Bayer Medical Care Inc., Indianola, PA (US)

(72) Inventors: Christopher D. Capone, Pittsburgh, PA (US); Ronald Heller, Monroeville, PA (US); John A. Haury, Sewickley, PA (US); Richard A. Seman, Delmont, PA (US); Joseph C. Mator, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 185 days.

(21) Appl. No.: 14/346,196

(22) PCT Filed: Sep. 20, 2012

(86) PCT No.: PCT/US2012/056364
§ 371 (c)(1),
(2) Date: Mar. 20, 2014

(87) PCT Pub. No.: WO2013/043889
PCT Pub. Date: Mar. 28, 2013

(65) Prior Publication Data
US 2015/0157789 A1    Jun. 11, 2015

Related U.S. Application Data

(60) Provisional application No. 61/537,371, filed on Sep. 21, 2011.

(51) Int. Cl.
*A61M 5/168* (2006.01)
*F04B 49/06* (2006.01)
(Continued)

(52) U.S. Cl.
CPC ........ *A61M 5/16881* (2013.01); *A61M 5/007* (2013.01); *A61M 5/1408* (2013.01);
(Continued)

(58) Field of Classification Search
CPC ............ A61M 5/16881; A61M 5/1422; A61M 5/1408; A61M 39/223; A61M 5/007;
(Continued)

(56) References Cited

U.S. PATENT DOCUMENTS 205,069 A    6/1878  Farnsworth
339,417 A    4/1886  Horen
(Continued)

FOREIGN PATENT DOCUMENTS

CN    2829775        10/2006
DE    4336336 A1     5/1994
(Continued)

OTHER PUBLICATIONS

The Written Opinion, International Search Report and International Preliminary Report on Patentability from corresponding PCT Application No. PCT/US12/56328 filed Sep. 20, 2012.
(Continued)

*Primary Examiner* — Ryan J Walters
(74) *Attorney, Agent, or Firm* — Joseph L. Kent; David Schramm; James R. Stevenson

(57) ABSTRACT

A system and method of assembling a disposable fluid pump device is provided. The fluid pump device includes a pump body having a plurality of pump cylinders and at least one inlet selector valve for controlling fluid input to the pump cylinders. The method includes the steps of identifying at least one initial inlet selector valve position; generating, with at least one processor, encoded data representing at
(Continued)

least the at least one inlet selector valve position; and setting the at least one selector valve to the at least one initial inlet selector valve position.

12 Claims, 33 Drawing Sheets

(51) Int. Cl.
*F04B 49/22* (2006.01)
*F04B 53/16* (2006.01)
*A61M 5/00* (2006.01)
*A61M 5/14* (2006.01)
*B05B 11/00* (2006.01)
*A61M 5/142* (2006.01)
*F16K 11/07* (2006.01)
*B23P 15/00* (2006.01)
*G05D 7/06* (2006.01)
*A61M 39/22* (2006.01)
*A61M 5/145* (2006.01)

(52) U.S. Cl.
CPC ........ *A61M 5/1422* (2013.01); *A61M 39/223* (2013.01); *B05B 11/3015* (2013.01); *B23P 15/001* (2013.01); *F04B 49/06* (2013.01); *F04B 49/065* (2013.01); *F04B 49/22* (2013.01); *F04B 53/16* (2013.01); *F16K 11/07* (2013.01); *G05D 7/0635* (2013.01); *A61M 5/1452* (2013.01); *A61M 2039/229* (2013.01); *A61M 2205/50* (2013.01); *A61M 2205/6063* (2013.01); *A61M 2207/00* (2013.01); *Y10T 29/49229* (2015.01); *Y10T 29/49236* (2015.01); *Y10T 29/49412* (2015.01); *Y10T 29/5191* (2015.01); *Y10T 137/86879* (2015.04)

(58) Field of Classification Search
CPC ........ F04B 49/065; F04B 53/16; F04B 49/22; F04B 49/06; G05D 7/0635; B23P 15/001; B05B 11/3015; F16K 11/07; Y10T 29/49412; Y10T 29/5191; Y10T 29/492
See application file for complete search history.

(56) References Cited

U.S. PATENT DOCUMENTS

| | | | |
|---|---|---|---|
| 372,093 A | 10/1887 | Struck |
| 373,292 A | 11/1887 | Jacobson et al. |
| 375,160 A | 12/1887 | Housel |
| 388,876 A | 9/1888 | Humans |
| 503,778 A | 8/1893 | Trimble |
| 517,192 A | 3/1894 | Prior |
| 567,115 A | 9/1896 | Atkinson et al. |
| 783,317 A | 2/1905 | Salsman |
| 921,691 A | 5/1909 | Friday |
| 1,103,212 A | 7/1914 | Kraemer |
| 1,324,654 A | 12/1919 | Ferguson |
| 1,346,127 A | 7/1920 | Lewis |
| 1,531,698 A | 3/1925 | Janes |
| 1,708,112 A | 4/1929 | Henry |
| 1,748,810 A | 2/1930 | Wandel |
| 1,845,882 A | 2/1932 | Litshge |
| 1,873,304 A | 8/1932 | De Mooy |
| 1,973,351 A | 9/1934 | Meeker |
| 2,019,402 A | 10/1935 | Duffy |
| 2,114,565 A | 4/1938 | Kovach |
| 2,206,816 A | 7/1940 | Levitt |
| 2,409,650 A | 10/1946 | Wiggins |
| 2,412,597 A | 12/1946 | Brewer |
| 2,417,250 A | 3/1947 | Harvey |
| 2,642,258 A | 6/1953 | Stone et al. |
| 2,702,008 A | 2/1955 | Stockard |
| 2,728,550 A | 12/1955 | Sinkler |
| 2,776,104 A | 1/1957 | Sinkler |
| 2,876,985 A | 3/1959 | Birchall, Jr. et al. |
| 2,946,606 A | 7/1960 | Smith |
| 3,038,694 A | 6/1962 | Dunbeck et al. |
| 3,048,191 A | 8/1962 | Crang |
| 3,093,359 A | 6/1963 | De Woody |
| 3,142,474 A | 7/1964 | Nelson |
| 3,146,775 A | 9/1964 | Moore et al. |
| 3,181,895 A | 5/1965 | Cator |
| 3,185,179 A | 5/1965 | Harautuneian |
| 3,206,163 A | 9/1965 | Freed |
| 3,245,698 A | 4/1966 | Fromknecht |
| 3,268,203 A | 8/1966 | Gilmont et al. |
| 3,276,472 A | 10/1966 | Jinkens et al. |
| 3,277,922 A | 10/1966 | Eisel |
| 3,394,954 A | 7/1968 | Sarns |
| 3,395,925 A | 8/1968 | Dreiding |
| 3,434,691 A | 3/1969 | Hamilton |
| 3,447,468 A | 6/1969 | Kinne |
| 3,447,479 A | 6/1969 | Rosenberg |
| 3,464,359 A | 9/1969 | Lee et al. |
| 3,484,077 A | 12/1969 | Porter |
| 3,485,265 A | 12/1969 | Buono |
| 3,489,158 A | 1/1970 | Mackay et al. |
| 3,548,827 A | 12/1970 | Abel |
| 3,552,393 A | 1/1971 | Willgerodt |
| 3,554,488 A | 1/1971 | Alexander |
| 3,569,903 A | 3/1971 | Brishka |
| 3,582,040 A | 6/1971 | Gutierrez |
| 3,597,113 A | 8/1971 | Dumoulin et al. |
| 3,614,060 A | 10/1971 | Freed et al. |
| 3,638,973 A | 2/1972 | Poletti |
| 3,687,416 A | 8/1972 | Mueller |
| 3,718,409 A | 2/1973 | Brandenberg et al. |
| 3,731,679 A | 5/1973 | Wilhelmson et al. |
| 3,739,943 A | 6/1973 | Wilhelmson et al. |
| 3,768,476 A | 10/1973 | Raitto |
| 3,828,775 A | 8/1974 | Armel |
| 3,855,129 A | 12/1974 | Abrahams et al. |
| 3,866,957 A | 2/1975 | Norton |
| 3,916,943 A | 11/1975 | Hester et al. |
| 3,940,325 A | 2/1976 | Hirao |
| 3,949,746 A | 4/1976 | Wallach |
| 3,958,898 A | 5/1976 | Abrahams et al. |
| 3,976,311 A | 8/1976 | Spendlove |
| 3,981,620 A | 9/1976 | Abrahams et al. |
| 3,986,508 A | 10/1976 | Barrington |
| 3,990,727 A | 11/1976 | Gallagher |
| 3,991,975 A | 11/1976 | Sibrava |
| 3,993,061 A | 11/1976 | O'Leary |
| 3,994,294 A | 11/1976 | Knute |
| 3,997,195 A | 12/1976 | Bartholomew |
| 4,014,467 A | 3/1977 | Ferguson |
| 4,014,514 A | 3/1977 | Priese et al. |
| 4,026,581 A | 5/1977 | Pasbrig |
| 4,030,494 A | 6/1977 | Tenczar |
| 4,032,263 A | 6/1977 | Pareja |
| 4,044,757 A | 8/1977 | McWhorter et al. |
| 4,044,758 A | 8/1977 | Patel |
| 4,049,295 A | 9/1977 | Piers |
| 4,065,230 A | 12/1977 | Gezari |
| 4,072,056 A | 2/1978 | Lee |
| 4,123,091 A | 10/1978 | Cosentino et al. |
| 4,127,360 A | 11/1978 | Carpenter |
| 4,137,011 A | 1/1979 | Rock |
| 4,147,184 A | 4/1979 | Jess |
| 4,161,949 A | 7/1979 | Thanawalla |
| 4,181,223 A | 1/1980 | Millet |
| 4,198,080 A | 4/1980 | Carpenter |
| 4,207,923 A | 6/1980 | Giurtino |
| 4,215,847 A | 8/1980 | Hoos |
| 4,225,290 A | 9/1980 | Allington |
| 4,233,156 A | 11/1980 | Tsukada et al. |
| 4,236,880 A | 12/1980 | Archibald |
| 4,245,963 A | 1/1981 | Hutchins et al. |
| 4,252,126 A | 2/1981 | Mandl |
| 4,253,501 A | 3/1981 | Ogle |
| 4,260,180 A | 4/1981 | Halushka et al. |

(56) References Cited

U.S. PATENT DOCUMENTS

| | | |
|---|---|---|
| 4,262,880 A | 4/1981 | Danko et al. |
| 4,275,868 A | 6/1981 | Crone |
| 4,306,705 A | 12/1981 | Svensson |
| 4,310,420 A | 1/1982 | Konishi et al. |
| 4,311,586 A | 1/1982 | Baldwin et al. |
| 4,326,697 A | 4/1982 | Autage et al. |
| 4,328,833 A | 5/1982 | Aurther |
| 4,352,636 A | 10/1982 | Patterson et al. |
| 4,365,635 A | 12/1982 | Bowman |
| 4,372,336 A | 2/1983 | Cornell et al. |
| 4,392,847 A | 7/1983 | Whitney et al. |
| 4,398,757 A | 8/1983 | Floyd et al. |
| 4,405,829 A | 9/1983 | Riverst et al. |
| 4,410,003 A | 10/1983 | Sandling |
| 4,412,834 A | 11/1983 | Kulin et al. |
| 4,431,009 A | 2/1984 | Marino, Jr. et al. |
| 4,433,973 A | 2/1984 | Kurtz et al. |
| 4,453,927 A | 6/1984 | Sinko |
| 4,469,121 A | 9/1984 | Moen |
| 4,469,935 A | 9/1984 | Candela |
| 4,470,771 A | 9/1984 | Hall et al. |
| 4,475,666 A | 10/1984 | Bilbrey et al. |
| 4,478,388 A | 10/1984 | George |
| 4,494,730 A | 1/1985 | George |
| 4,503,333 A | 3/1985 | Kulin et al. |
| RE31,873 E | 4/1985 | Howes |
| 4,508,103 A | 4/1985 | Calisi |
| 4,508,367 A | 4/1985 | Oreopoulos et al. |
| 4,511,359 A | 4/1985 | Vaillancourt |
| 4,512,364 A | 4/1985 | Phillips |
| 4,512,764 A | 4/1985 | Wunsch |
| 4,525,165 A | 6/1985 | Fischell |
| 4,535,820 A | 8/1985 | Raines |
| 4,552,513 A | 11/1985 | Miller et al. |
| 4,559,036 A | 12/1985 | Wunsch |
| 4,563,175 A | 1/1986 | LaFond |
| 4,572,231 A | 2/1986 | Katayama |
| 4,595,495 A | 6/1986 | Yotam et al. |
| 4,595,595 A | 6/1986 | Gunnerson et al. |
| 4,604,093 A | 8/1986 | Brown et al. |
| 4,613,325 A | 9/1986 | Abrams |
| 4,655,762 A | 4/1987 | Rogers |
| 4,681,513 A | 7/1987 | Saito et al. |
| 4,695,276 A | 9/1987 | Shinno et al. |
| 4,734,011 A | 3/1988 | Hall, Jr. |
| 4,737,148 A | 4/1988 | Blake |
| 4,752,292 A | 6/1988 | Lopez et al. |
| 4,775,173 A | 10/1988 | Sauer |
| 4,778,447 A | 10/1988 | Velde et al. |
| 4,795,441 A | 1/1989 | Bhatt |
| 4,797,207 A | 1/1989 | Honganen et al. |
| 4,807,666 A | 2/1989 | Morse |
| 4,808,077 A | 2/1989 | Kan et al. |
| 4,810,168 A | 3/1989 | Nogami et al. |
| 4,810,241 A | 3/1989 | Rogers |
| 4,813,210 A | 3/1989 | Masuda et al. |
| 4,820,288 A | 4/1989 | Isono |
| 4,834,108 A | 5/1989 | Vaillancourt |
| 4,838,860 A | 6/1989 | Groshong et al. |
| 4,844,413 A | 7/1989 | Weber et al. |
| 4,846,797 A | 7/1989 | Howson et al. |
| 4,850,980 A | 7/1989 | Lentz et al. |
| 4,854,324 A | 8/1989 | Hirschman et al. |
| 4,874,378 A | 10/1989 | Hillstead |
| 4,875,718 A | 10/1989 | Marken |
| 4,883,409 A | 11/1989 | Strohmeier et al. |
| 4,890,817 A | 1/1990 | Uri |
| 4,898,579 A | 2/1990 | Groshong et al. |
| 4,913,624 A | 4/1990 | Seki et al. |
| 4,915,591 A | 4/1990 | Funke |
| 4,915,688 A | 4/1990 | Bischof et al. |
| 4,936,753 A | 6/1990 | Kozumplik, Jr. et al. |
| 4,941,308 A | 7/1990 | Grabenkort et al. |
| 4,946,047 A | 8/1990 | Kurokawa et al. |
| 4,947,856 A | 8/1990 | Beard |
| 4,954,239 A | 9/1990 | Mueller |
| 4,966,199 A | 10/1990 | Ruschke |
| 4,966,579 A | 10/1990 | Polaschegg |
| 4,969,879 A | 11/1990 | Lichte |
| 4,982,760 A | 1/1991 | Mustaklem |
| 4,994,035 A | 2/1991 | Mokros |
| 5,014,494 A | 5/1991 | George |
| 5,029,973 A | 7/1991 | Rink |
| 5,033,777 A | 7/1991 | Blenkush |
| 5,037,067 A | 8/1991 | Ray |
| 5,044,902 A | 9/1991 | Malbec |
| 5,047,021 A | 9/1991 | Utterberg |
| 5,057,076 A | 10/1991 | Polaschegg |
| 5,062,774 A | 11/1991 | Kramer et al. |
| 5,066,282 A | 11/1991 | Wijay et al. |
| 5,078,580 A | 1/1992 | Miller et al. |
| 5,078,683 A | 1/1992 | Sancoff et al. |
| 5,087,086 A | 2/1992 | Snedeker |
| 5,098,407 A | 3/1992 | Okamura |
| 5,100,103 A | 3/1992 | Conley et al. |
| 5,104,158 A | 4/1992 | Meyer et al. |
| 5,104,374 A | 4/1992 | Bishko et al. |
| 5,116,086 A | 5/1992 | Psajd |
| 5,117,870 A | 6/1992 | Goodale et al. |
| 5,135,026 A | 8/1992 | Manska |
| 5,143,257 A | 9/1992 | Austin et al. |
| 5,153,827 A | 10/1992 | Coutre et al. |
| 5,165,728 A | 11/1992 | Mayer |
| 5,176,415 A | 1/1993 | Choksi |
| 5,190,071 A | 3/1993 | Sule |
| 5,190,534 A | 3/1993 | Kendell |
| 5,192,269 A | 3/1993 | Poli et al. |
| 5,196,197 A | 3/1993 | Talwar et al. |
| 5,197,438 A | 3/1993 | Kumano et al. |
| 5,205,322 A | 4/1993 | Merick et al. |
| 5,207,641 A | 5/1993 | Allton |
| 5,207,642 A | 5/1993 | Orkin et al. |
| 5,213,376 A | 5/1993 | Szabo |
| 5,226,886 A | 7/1993 | Skakoon et al. |
| 5,234,193 A | 8/1993 | Neal et al. |
| 5,237,309 A | 8/1993 | Frantz et al. |
| 5,243,982 A | 9/1993 | Mostl et al. |
| 5,249,579 A | 10/1993 | Hobbs et al. |
| 5,254,101 A | 10/1993 | Trombley, III |
| 5,260,020 A | 11/1993 | Wilk et al. |
| 5,267,964 A | 12/1993 | Karg |
| 5,288,290 A | 2/1994 | Brody |
| 5,318,328 A | 6/1994 | Dawson |
| 5,328,463 A | 7/1994 | Barton et al. |
| 5,334,163 A | 8/1994 | Sinnett |
| 5,346,470 A | 9/1994 | Hobbs et al. |
| 5,362,291 A | 11/1994 | Williamson, IV |
| 5,376,070 A | 12/1994 | Purvis et al. |
| 5,377,718 A | 1/1995 | Sand |
| 5,378,231 A | 1/1995 | Johnson et al. |
| 5,411,485 A | 5/1995 | Tennican et al. |
| 5,411,490 A | 5/1995 | Tennican et al. |
| 5,417,667 A | 5/1995 | Tennican et al. |
| 5,419,354 A | 5/1995 | Krynicki |
| 5,423,323 A | 6/1995 | Orth |
| 5,429,485 A | 7/1995 | Dodge |
| 5,443,453 A | 8/1995 | Walker et al. |
| 5,445,621 A | 8/1995 | Poli et al. |
| 5,449,206 A | 9/1995 | Lockwood |
| 5,450,847 A | 9/1995 | Kampfe et al. |
| 5,452,748 A | 9/1995 | Simmons et al. |
| 5,454,792 A | 10/1995 | Tennican et al. |
| 5,454,972 A | 10/1995 | Williams et al. |
| 5,460,609 A | 10/1995 | O'Donnell |
| 5,462,251 A | 10/1995 | Kawabe |
| 5,466,228 A | 11/1995 | Evans |
| 5,474,099 A | 12/1995 | Boehmer et al. |
| 5,478,338 A | 12/1995 | Reynard |
| 5,480,386 A | 1/1996 | Brohy et al. |
| 5,492,535 A | 2/1996 | Reed et al. |
| 5,494,036 A | 2/1996 | Uber, III et al. |
| 5,496,273 A | 3/1996 | Pastrone et al. |
| 5,507,733 A | 4/1996 | Larkin et al. |
| 5,515,851 A | 5/1996 | Goldstein |

(56) References Cited

U.S. PATENT DOCUMENTS

| | | |
|---|---|---|
| 5,529,463 A | 6/1996 | Layer et al. |
| 5,531,697 A | 7/1996 | Olsen et al. |
| 5,531,698 A | 7/1996 | Olsen |
| 5,531,712 A | 7/1996 | Malcolm et al. |
| 5,558,669 A | 9/1996 | Reynard |
| 5,569,181 A | 10/1996 | Heilman et al. |
| 5,573,505 A | 11/1996 | Johnson et al. |
| 5,573,515 A | 11/1996 | Wilson et al. |
| 5,578,016 A | 11/1996 | Zinger |
| 5,580,530 A | 12/1996 | Kowatsch et al. |
| 5,583,902 A | 12/1996 | Bae |
| 5,588,816 A | 12/1996 | Abbott et al. |
| 5,592,940 A | 1/1997 | Kampfe et al. |
| 5,603,900 A | 2/1997 | Clark et al. |
| 5,609,572 A | 3/1997 | Lang |
| 5,632,606 A | 5/1997 | Jacobsen et al. |
| 5,645,538 A | 7/1997 | Richmond |
| 5,647,854 A | 7/1997 | Olsen et al. |
| 5,655,897 A | 8/1997 | Neftel et al. |
| 5,687,208 A | 11/1997 | Bae et al. |
| 5,697,899 A | 12/1997 | Hillman et al. |
| 5,704,914 A | 1/1998 | Stocking et al. |
| 5,714,060 A | 2/1998 | Kenley et al. |
| 5,718,568 A | 2/1998 | Neftel et al. |
| 5,718,569 A | 2/1998 | Holst |
| 5,739,508 A | 4/1998 | Uber, III |
| 5,741,125 A | 4/1998 | Neftel et al. |
| 5,741,710 A | 4/1998 | Ek |
| 5,755,683 A | 5/1998 | Houle et al. |
| 5,764,159 A | 6/1998 | Neftel |
| 5,772,585 A | 6/1998 | Lavin et al. |
| 5,782,611 A | 7/1998 | Neftel et al. |
| 5,788,669 A | 8/1998 | Peterson |
| 5,795,333 A | 8/1998 | Reilly et al. |
| 5,799,987 A | 9/1998 | Sampson |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,817,067 A | 10/1998 | Tsukada |
| 5,817,068 A | 10/1998 | Urrutia |
| 5,819,229 A | 10/1998 | Boppe |
| 5,822,544 A | 10/1998 | Chaco et al. |
| 5,827,262 A | 10/1998 | Neftel et al. |
| 5,830,195 A | 11/1998 | Peters et al. |
| 5,832,959 A | 11/1998 | Szymczakowski et al. |
| 5,840,026 A | 11/1998 | Uber, III et al. |
| 5,843,037 A | 12/1998 | Uber, III |
| 5,852,231 A | 12/1998 | Kaji |
| 5,865,797 A | 2/1999 | Zeeman |
| 5,873,861 A | 2/1999 | Hitchins et al. |
| 5,885,216 A | 3/1999 | Evans, III et al. |
| 5,901,745 A | 5/1999 | Buchtel |
| 5,901,944 A | 5/1999 | Ramakrishnan et al. |
| 5,911,687 A | 6/1999 | Sato et al. |
| 5,916,197 A | 6/1999 | Reilly et al. |
| 5,916,201 A | 6/1999 | Wilson, Jr. et al. |
| 5,920,054 A | 7/1999 | Uber, III |
| 5,924,074 A | 7/1999 | Evans |
| 5,927,885 A | 7/1999 | Duez et al. |
| 5,935,099 A | 8/1999 | Peterson et al. |
| 5,937,885 A | 8/1999 | Sampson |
| 5,947,935 A | 9/1999 | Rhinehart et al. |
| 5,947,958 A | 9/1999 | Woodard et al. |
| 5,953,453 A | 9/1999 | Fan et al. |
| 5,954,700 A | 9/1999 | Kovelman |
| 5,964,485 A | 10/1999 | Hame et al. |
| 5,968,014 A | 10/1999 | Neftel et al. |
| 5,980,501 A | 11/1999 | Gray |
| 5,984,378 A | 11/1999 | Ostrander et al. |
| 5,993,654 A | 11/1999 | Black |
| 6,022,053 A | 2/2000 | Hukuda |
| 6,036,458 A | 3/2000 | Cole et al. |
| RE36,648 E | 4/2000 | Uber, III et al. |
| 6,047,259 A | 4/2000 | Campbell et al. |
| 6,068,617 A | 5/2000 | Richmond |
| 6,077,055 A | 6/2000 | Vilks |
| 6,079,691 A | 6/2000 | Dragone |
| 6,083,205 A | 7/2000 | Bourne et al. |
| 6,085,574 A | 7/2000 | Neftel et al. |
| 6,092,722 A | 7/2000 | Heinrichs et al. |
| 6,096,011 A | 8/2000 | Trombley, III et al. |
| 6,099,511 A | 8/2000 | Devos et al. |
| 6,106,498 A | 8/2000 | Friedli et al. |
| 6,110,152 A | 8/2000 | Kovelman |
| 6,120,490 A | 9/2000 | Neftel |
| 6,123,686 A | 9/2000 | Olsen et al. |
| 6,149,627 A | 11/2000 | Uber, III |
| 6,155,307 A | 12/2000 | Vanneste |
| 6,155,607 A | 12/2000 | Hewitt et al. |
| 6,157,914 A | 12/2000 | Seto et al. |
| 6,158,467 A | 12/2000 | Loo |
| 6,164,044 A | 12/2000 | Porfano et al. |
| 6,189,704 B1 | 2/2001 | Dennehey et al. |
| 6,197,000 B1 | 3/2001 | Reilly et al. |
| 6,200,111 B1 | 3/2001 | Foss |
| 6,220,487 B1 | 4/2001 | Srivastava et al. |
| 6,250,052 B1 | 6/2001 | Porfano et al. |
| 6,260,021 B1 | 7/2001 | Wong et al. |
| 6,263,641 B1 | 7/2001 | Odell et al. |
| 6,269,704 B1 | 8/2001 | Ziv et al. |
| 6,270,478 B1 | 8/2001 | Mernøe |
| 6,272,469 B1 | 8/2001 | Koritzinsky et al. |
| 6,280,430 B1 | 8/2001 | Neftel et al. |
| 6,283,761 B1 | 9/2001 | Joao |
| 6,285,285 B1 | 9/2001 | Mongrenier |
| 6,293,756 B1 | 9/2001 | Andersson |
| 6,305,724 B1 | 10/2001 | Sampson |
| 6,306,117 B1 | 10/2001 | Uber, III |
| 6,317,623 B1 | 11/2001 | Griffiths et al. |
| 6,319,236 B1 | 11/2001 | Böck |
| 6,339,718 B1 | 1/2002 | Zatezalo et al. |
| RE37,602 E | 3/2002 | Uber, III et al. |
| 6,361,051 B1 | 3/2002 | Babin |
| 6,364,279 B1 | 4/2002 | Neftel et al. |
| 6,366,206 B1 | 4/2002 | Ishikawa et al. |
| 6,368,080 B1 | 4/2002 | Sipin |
| 6,371,444 B1 | 4/2002 | Hahn et al. |
| 6,385,483 B1 | 5/2002 | Uber, III et al. |
| 6,397,098 B1 | 5/2002 | Uber, III et al. |
| 6,398,513 B1 | 6/2002 | Amsler et al. |
| 6,402,717 B1 | 6/2002 | Reilly et al. |
| 6,418,966 B2 | 7/2002 | Loo |
| 6,436,072 B1 | 8/2002 | Kullas et al. |
| 6,440,107 B1 | 8/2002 | Trombley, III et al. |
| 6,442,418 B1 | 8/2002 | Evans, III et al. |
| 6,443,496 B2 | 9/2002 | Campau |
| 6,454,162 B1 | 9/2002 | Teller |
| 6,457,488 B2 | 10/2002 | Loo |
| 6,468,261 B1 | 10/2002 | Small et al. |
| 6,468,424 B1 | 10/2002 | Dönig et al. |
| 6,471,671 B1 | 10/2002 | Urick et al. |
| 6,471,674 B1 | 10/2002 | Emig et al. |
| 6,475,192 B1 | 11/2002 | Reilly et al. |
| 6,491,189 B2 | 12/2002 | Friedman |
| 6,501,068 B1 * | 12/2002 | Eisenhauer ........ B23K 26/0823 250/231.14 |
| 6,502,937 B2 | 1/2003 | Yang |
| 6,503,225 B1 | 1/2003 | Kirsch et al. |
| 6,511,459 B1 | 1/2003 | Fago |
| 6,519,569 B1 | 2/2003 | White et al. |
| 6,520,930 B2 | 2/2003 | Critchlow et al. |
| 6,530,907 B1 | 3/2003 | Sugahara et al. |
| 6,536,742 B2 | 3/2003 | Lotz et al. |
| 6,540,486 B2 | 4/2003 | Amsler et al. |
| 6,558,125 B1 | 5/2003 | Futterknecht |
| 6,558,343 B1 | 5/2003 | Neftel |
| 6,575,930 B1 | 6/2003 | Trombley, III et al. |
| 6,607,179 B2 | 8/2003 | Moretti et al. |
| 6,623,455 B2 | 9/2003 | Small et al. |
| 6,626,355 B2 | 9/2003 | Sasse et al. |
| 6,635,033 B1 | 10/2003 | Hill et al. |
| 6,638,258 B2 | 10/2003 | Schwartz et al. |
| 6,638,263 B1 | 10/2003 | Theeuwes et al. |
| 6,643,537 B1 | 11/2003 | Zatezalo et al. |

(56) References Cited

U.S. PATENT DOCUMENTS

| | | |
|---|---|---|
| 6,648,017 B2 | 11/2003 | Lamas et al. |
| 6,649,829 B2 | 11/2003 | Garber et al. |
| 6,652,489 B2 | 11/2003 | Trocki et al. |
| 6,673,033 B1 | 1/2004 | Sciulli et al. |
| 6,676,104 B2 | 1/2004 | Tillander |
| 6,682,044 B2 | 1/2004 | Miller |
| 6,685,831 B2 | 2/2004 | Dönig et al. |
| 6,699,219 B2 | 3/2004 | Emig et al. |
| 6,708,944 B2 | 3/2004 | Pfeil et al. |
| 6,708,948 B2 | 3/2004 | Nosel |
| 6,716,193 B1 | 4/2004 | Neftel |
| 6,722,705 B2 | 4/2004 | Korkor |
| 6,731,971 B2 | 5/2004 | Evans, III et al. |
| 6,733,477 B2 | 5/2004 | Cowan et al. |
| 6,733,478 B2 | 5/2004 | Reilly et al. |
| 6,742,680 B2 | 6/2004 | Friedman |
| 6,743,202 B2 | 6/2004 | Hirschman et al. |
| 6,749,090 B2 | 6/2004 | Bailey |
| 6,767,034 B2 | 7/2004 | Le Clinche |
| 6,796,965 B2 | 9/2004 | Dumaresq Lucas et al. |
| 6,857,617 B2 | 2/2005 | Forberg |
| 6,861,954 B2 | 3/2005 | Levin |
| 6,871,660 B2 | 3/2005 | Hampsch |
| 6,874,759 B2 | 4/2005 | Aoshima et al. |
| 6,880,808 B2 | 4/2005 | McPeak et al. |
| 6,884,255 B1 | 4/2005 | Newton |
| 6,889,074 B2 | 5/2005 | Uber, III et al. |
| 6,892,996 B2 | 5/2005 | Starchevich |
| 6,897,374 B2 | 5/2005 | Garber et al. |
| 6,901,283 B2 | 5/2005 | Evans, III et al. |
| 6,908,118 B2 | 6/2005 | Fumioka |
| 6,918,893 B2 | 7/2005 | Houde et al. |
| 6,929,235 B1 | 8/2005 | Height et al. |
| 6,929,236 B1 | 8/2005 | Height et al. |
| 6,937,150 B2 | 8/2005 | Medema et al. |
| 6,939,302 B2 | 9/2005 | Griffiths et al. |
| 6,953,450 B2 | 10/2005 | Baldwin et al. |
| 6,953,453 B2 | 10/2005 | Recinella et al. |
| 6,967,974 B1 | 11/2005 | Partyka |
| 6,972,001 B2 | 12/2005 | Emig et al. |
| 6,976,628 B2 | 12/2005 | Krupa |
| 6,985,870 B2 | 1/2006 | Martucci et al. |
| 7,005,078 B2 | 2/2006 | Van Lintel et al. |
| 7,014,624 B2 | 3/2006 | Meythaler et al. |
| 7,017,800 B2 | 3/2006 | Ulrich et al. |
| 7,017,948 B2 | 3/2006 | Sunohara et al. |
| 7,041,081 B2 | 5/2006 | Minezaki et al. |
| 7,041,941 B2 | 5/2006 | Faries, Jr. et al. |
| 7,047,058 B1 | 5/2006 | Dvorsky et al. |
| 7,047,984 B2 | 5/2006 | Blattner et al. |
| 7,047,994 B2 | 5/2006 | McPeak et al. |
| 7,048,193 B2 | 5/2006 | Tsukada et al. |
| 7,060,049 B2 | 6/2006 | Trombley, III et al. |
| 7,063,785 B2 | 6/2006 | Hiraku et al. |
| 7,079,886 B2 | 7/2006 | Zatezalo et al. |
| 7,091,864 B2 | 8/2006 | Veitch et al. |
| 7,094,216 B2 | 8/2006 | Trombley, III et al. |
| 7,097,690 B2 | 8/2006 | Usher et al. |
| 7,108,184 B2 | 9/2006 | Mase et al. |
| 7,115,113 B2 | 10/2006 | Evans et al. |
| 7,128,347 B2 | 10/2006 | Kerin |
| 7,137,974 B2 | 11/2006 | Almasian et al. |
| 7,160,020 B2 | 1/2007 | Sand |
| 7,169,135 B2 | 1/2007 | Duchon et al. |
| 7,172,572 B2 | 2/2007 | Diamond et al. |
| 7,174,923 B2 | 2/2007 | Schorn et al. |
| 7,178,515 B2 | 2/2007 | Carpenter et al. |
| 7,189,320 B2 | 3/2007 | Takao et al. |
| 7,193,519 B2 | 3/2007 | Root et al. |
| 7,195,624 B2 | 3/2007 | Lockwood et al. |
| 7,201,185 B2 | 4/2007 | Poppe et al. |
| 7,204,421 B2 | 4/2007 | Austin |
| 7,213,760 B2 | 5/2007 | Mase et al. |
| 7,213,767 B2 | 5/2007 | Tethrake et al. |
| 7,214,039 B2 | 5/2007 | Angove |
| 7,217,105 B2 | 5/2007 | Angove |
| 7,236,936 B2 | 6/2007 | White et al. |
| 7,278,778 B2 | 10/2007 | Sand |
| 7,309,014 B2 | 12/2007 | Truong |
| 7,311,503 B2 | 12/2007 | Van Lintel et al. |
| 7,326,188 B1 | 2/2008 | Russell et al. |
| 7,364,657 B2 | 4/2008 | Mandrusov et al. |
| 7,367,358 B2 | 5/2008 | Malcolm |
| 7,374,718 B2 | 5/2008 | Dhara et al. |
| 7,431,989 B2 | 10/2008 | Sakhrani et al. |
| 7,451,959 B2 | 11/2008 | Matzner |
| 7,497,840 B2 | 3/2009 | Neftel et al. |
| 7,531,098 B2 | 5/2009 | Robinson et al. |
| 7,553,304 B2 | 6/2009 | Neftel |
| 7,618,397 B2 | 11/2009 | Hicks |
| 7,695,445 B2 | 4/2010 | Yuki |
| 7,762,989 B2 | 7/2010 | Simpson |
| 7,766,883 B2 | 8/2010 | Rellly et al. |
| 7,771,383 B2 | 8/2010 | Truitt et al. |
| 7,782,467 B2 | 8/2010 | Chappel |
| 7,887,308 B2 | 2/2011 | Navarro |
| 7,887,509 B2 | 2/2011 | Thiebaud et al. |
| 7,901,386 B2 | 3/2011 | Hishikawa et al. |
| 7,901,727 B2 | 3/2011 | Hofmann et al. |
| 7,905,861 B2 | 3/2011 | Rhinehart et al. |
| 7,935,077 B2 | 5/2011 | Thor et al. |
| 7,951,112 B2 | 5/2011 | Patzer |
| 7,963,951 B2 | 6/2011 | Kitani et al. |
| 7,984,730 B2 | 7/2011 | Ziv et al. |
| 8,011,897 B2 | 9/2011 | Raleigh et al. |
| 8,061,687 B2 | 11/2011 | Anderson |
| 8,062,003 B2 | 11/2011 | Goertzen et al. |
| 8,062,009 B2 | 11/2011 | Cueni |
| 8,133,205 B2 | 3/2012 | Rhinehart et al. |
| 8,172,199 B2 | 5/2012 | Ushigusa et al. |
| 8,308,167 B2 | 11/2012 | Balsells et al. |
| 8,353,688 B2 | 1/2013 | Navarro |
| 8,382,712 B2 | 2/2013 | Kim |
| 8,944,780 B2 | 2/2015 | Reilly |
| 2002/0026148 A1 | 2/2002 | Uber |
| 2002/0061375 A1 | 5/2002 | Cartledge et al. |
| 2002/0084437 A1 | 7/2002 | Nitsche et al. |
| 2002/0099334 A1 | 7/2002 | Hanson et al. |
| 2002/0139088 A1 | 10/2002 | Woodworth et al. |
| 2002/0143294 A1 | 10/2002 | Duchon et al. |
| 2002/0147429 A1 | 10/2002 | Cowan et al. |
| 2002/0172615 A1 | 11/2002 | Woodworth et al. |
| 2002/0188259 A1 | 12/2002 | Hickle et al. |
| 2002/0191487 A1 | 12/2002 | Sand |
| 2003/0071233 A1 | 4/2003 | Stewart et al. |
| 2003/0140929 A1 | 7/2003 | Wilkes et al. |
| 2003/0155385 A1 | 8/2003 | Sohoel et al. |
| 2003/0171670 A1 | 9/2003 | Gumb et al. |
| 2003/0181850 A1 | 9/2003 | Diamond et al. |
| 2003/0216643 A1 | 11/2003 | Zatezalo et al. |
| 2004/0008123 A1 | 1/2004 | Carrender et al. |
| 2004/0064041 A1* | 4/2004 | Lazzaro ............ A61M 5/14546 600/432 |
| 2004/0074281 A1 | 4/2004 | Lobdell et al. |
| 2004/0092908 A1 | 5/2004 | Harper et al. |
| 2004/0104271 A1 | 6/2004 | Martucci et al. |
| 2004/0116862 A1 | 6/2004 | Ray |
| 2004/0130438 A1 | 7/2004 | Garber |
| 2004/0143225 A1 | 7/2004 | Callan et al. |
| 2004/0171982 A1 | 9/2004 | Danchin |
| 2004/0193328 A1 | 9/2004 | Zaitsu et al. |
| 2004/0193453 A1 | 9/2004 | Butterfield et al. |
| 2004/0199075 A1 | 10/2004 | Evans et al. |
| 2004/0221904 A1 | 11/2004 | Usher et al. |
| 2004/0222180 A1 | 11/2004 | Wicks et al. |
| 2004/0241023 A1 | 12/2004 | Pinkerton et al. |
| 2005/0010175 A1 | 1/2005 | Beedon et al. |
| 2005/0019187 A1 | 1/2005 | Whitworth et al. |
| 2005/0057042 A1 | 3/2005 | Wicks |
| 2005/0070978 A1 | 3/2005 | Bek et al. |
| 2005/0075611 A1 | 4/2005 | Hetzler et al. |
| 2005/0082828 A1 | 4/2005 | Wicks et al. |
| 2005/0084410 A1 | 4/2005 | Meyer et al. |
| 2005/0089994 A1 | 4/2005 | Neftel |

(56) References Cited

U.S. PATENT DOCUMENTS

| | | |
|---|---|---|
| 2005/0113763 A1 | 5/2005 | Reynolds |
| 2005/0118048 A1 | 6/2005 | Traxinger |
| 2005/0129569 A1 | 6/2005 | Zhao et al. |
| 2005/0194722 A1 | 9/2005 | Muratoglu et al. |
| 2005/0194723 A1 | 9/2005 | Muratoglu et al. |
| 2005/0211905 A1 | 9/2005 | Stark |
| 2005/0211934 A1 | 9/2005 | Garber et al. |
| 2005/0234394 A1 | 10/2005 | Ross |
| 2005/0245883 A1 | 11/2005 | Baldwin |
| 2005/0277873 A1 | 12/2005 | Stewart et al. |
| 2005/0277890 A1 | 12/2005 | Stewart et al. |
| 2006/0009699 A1 | 1/2006 | Roteliuk et al. |
| 2006/0013849 A1 | 1/2006 | Strickler et al. |
| 2006/0016897 A1 | 1/2006 | Yasuda et al. |
| 2006/0049629 A1 | 3/2006 | Naumann et al. |
| 2006/0065739 A1 | 3/2006 | Falls et al. |
| 2006/0069356 A1 | 3/2006 | Witowski |
| 2006/0076419 A1 | 4/2006 | Johnson |
| 2006/0086363 A1 | 4/2006 | Qin et al. |
| 2006/0091209 A1 | 5/2006 | He |
| 2006/0108008 A1 | 5/2006 | Guala |
| 2006/0116639 A1 | 6/2006 | Russell |
| 2006/0131423 A1 | 6/2006 | Truong |
| 2006/0153716 A1 | 7/2006 | Shoji et al. |
| 2006/0155248 A1 | 7/2006 | Hashimoto et al. |
| 2006/0167415 A1 | 7/2006 | Nemoto |
| 2006/0184008 A1 | 8/2006 | Zatezalo et al. |
| 2006/0224128 A1 | 10/2006 | Lurvey et al. |
| 2006/0235297 A1 | 10/2006 | Kawamoto |
| 2006/0243804 A1 | 11/2006 | Christoffersen et al. |
| 2007/0053788 A1 | 3/2007 | Zhao |
| 2007/0056871 A1 | 3/2007 | Griffiths et al. |
| 2007/0060874 A1 | 3/2007 | Nesbitt et al. |
| 2007/0073246 A1 | 3/2007 | Simon |
| 2007/0078203 A1 | 4/2007 | Gohill |
| 2007/0084524 A1 | 4/2007 | Py |
| 2007/0085049 A1 | 4/2007 | Houle et al. |
| 2007/0096906 A1 | 5/2007 | Lyons et al. |
| 2007/0100315 A1 | 5/2007 | Traxinger |
| 2007/0100316 A1 | 5/2007 | Traxinger |
| 2007/0106264 A1 | 5/2007 | Proulx et al. |
| 2007/0112265 A1 | 5/2007 | Zatezalo et al. |
| 2007/0115125 A1 | 5/2007 | Lyon et al. |
| 2007/0119929 A1 | 5/2007 | Swan et al. |
| 2007/0123620 A1 | 5/2007 | Nayak et al. |
| 2007/0125870 A1 | 6/2007 | Mase et al. |
| 2007/0129680 A1 | 6/2007 | Hagg et al. |
| 2007/0159337 A1 | 7/2007 | Tethrake et al. |
| 2007/0167910 A1 | 7/2007 | Tennican et al. |
| 2007/0167919 A1 | 7/2007 | Nemoto et al. |
| 2007/0187475 A1 | 8/2007 | MacLeod |
| 2007/0191760 A1 | 8/2007 | Iguchi et al. |
| 2007/0197974 A1 | 8/2007 | Gibson |
| 2007/0204612 A1 | 9/2007 | Klimowicz |
| 2007/0213662 A1 | 9/2007 | Kalafut et al. |
| 2007/0225601 A1 | 9/2007 | Uber et al. |
| 2007/0244437 A1 | 10/2007 | Castillo et al. |
| 2007/0287954 A1 | 12/2007 | Zhao et al. |
| 2008/0014105 A1 | 1/2008 | Neftel et al. |
| 2008/0024310 A1 | 1/2008 | Baker et al. |
| 2008/0034959 A1 | 2/2008 | Vu |
| 2008/0045919 A1 | 2/2008 | Jakob et al. |
| 2008/0058711 A1 | 3/2008 | Neftel et al. |
| 2008/0069970 A1 | 3/2008 | Wu |
| 2008/0071228 A1 | 3/2008 | Wu et al. |
| 2008/0131300 A1 | 6/2008 | Junod et al. |
| 2008/0172002 A1 | 7/2008 | Bell et al. |
| 2008/0213115 A1 | 9/2008 | Hilger et al. |
| 2008/0287887 A1 | 11/2008 | Mack et al. |
| 2008/0294029 A1 | 11/2008 | Piveteau et al. |
| 2008/0294040 A1 | 11/2008 | Mohiuddin et al. |
| 2008/0319401 A1 | 12/2008 | Funamura et al. |
| 2009/0012466 A1 | 1/2009 | Zhao et al. |
| 2009/0043253 A1 | 2/2009 | Podaima |
| 2009/0112164 A1 | 4/2009 | Reilly et al. |
| 2009/0118695 A1 | 5/2009 | Neftel |
| 2009/0152098 A1 | 6/2009 | Hooper et al. |
| 2009/0173903 A1 | 7/2009 | Kaneko et al. |
| 2009/0187139 A1 | 7/2009 | Mastalli et al. |
| 2009/0199917 A1 | 8/2009 | Vallet et al. |
| 2009/0240233 A1 | 9/2009 | Neftel |
| 2009/0277276 A1 | 11/2009 | Evering et al. |
| 2009/0324676 A1 | 12/2009 | Hofmann et al. |
| 2010/0012207 A1 | 1/2010 | Satoh et al. |
| 2010/0022968 A1 | 1/2010 | Kitani |
| 2010/0028170 A1 | 2/2010 | Schneeberger et al. |
| 2010/0030070 A1 | 2/2010 | Duffour et al. |
| 2010/0096302 A1 | 4/2010 | Astle et al. |
| 2010/0106012 A1 | 4/2010 | De Marco |
| 2010/0191106 A1 | 7/2010 | Koyama |
| 2010/0256569 A1 | 10/2010 | Cachemaille et al. |
| 2010/0280458 A1 | 11/2010 | Cachemaille et al. |
| 2010/0298699 A1 | 11/2010 | Reilly et al. |
| 2010/0324504 A1 | 12/2010 | Chappel et al. |
| 2011/0002802 A1 | 1/2011 | Capone et al. |
| 2011/0024657 A1 | 2/2011 | Tower |
| 2011/0054397 A1 | 3/2011 | Menot et al. |
| 2011/0132480 A1 | 6/2011 | Chappel |
| 2011/0142688 A1 | 6/2011 | Chappel et al. |
| 2011/0144585 A1 | 6/2011 | Bianchi et al. |
| 2011/0152681 A1 | 6/2011 | Reilly |
| 2011/0178493 A1 | 7/2011 | Okiyama |
| 2011/0200456 A1 | 8/2011 | Patzer |
| 2011/0308651 A1 | 12/2011 | Ziv et al. |
| 2012/0046610 A1 | 2/2012 | Rankin |
| 2012/0244018 A1 | 9/2012 | Reilly |
| 2013/0072880 A1 | 3/2013 | Finke |
| 2013/0116620 A1 | 5/2013 | Rotem et al. |

FOREIGN PATENT DOCUMENTS

| | | |
|---|---|---|
| EP | 0068555 A1 | 1/1983 |
| FR | 2715310 A1 | 7/1995 |
| GB | 0511715 A | 8/1939 |
| GB | 884234 A | 12/1961 |
| GB | 1511715 A | 5/1978 |
| GB | 2044888 | 10/1980 |
| JP | H06142200 A | 5/1944 |
| JP | H04241778 A | 8/1992 |
| JP | H05272685 A | 10/1993 |
| JP | H06142199 A | 5/1994 |
| JP | 2007014492 A | 1/2007 |
| JP | 2007113433 A | 5/2007 |
| NL | 9500612 | 11/1996 |
| WO | 9323740 A1 | 11/1993 |
| WO | 9531643 A1 | 11/1995 |
| WO | 9611025 A1 | 4/1996 |
| WO | 9621151 A1 | 7/1996 |
| WO | 9700093 A1 | 1/1997 |
| WO | 9702853 A1 | 1/1997 |
| WO | 9716217 A1 | 5/1997 |
| WO | 99/34846 | 5/1999 |
| WO | 99/38558 | 8/1999 |
| WO | 02/48589 | 6/2002 |
| WO | 3063929 A1 | 8/2003 |
| WO | 2005106251 A1 | 11/2005 |
| WO | 2006056828 | 5/2006 |
| WO | 2011033440 A1 | 3/2011 |

OTHER PUBLICATIONS

The Written Opinion, International Search Report and International Preliminary Report on Patentability from corresponding PCT Application No. PCT/US12/56355 filed Sep. 20, 2012.

The Written Opinion, International Search Report and International Preliminary Report on Patentability from corresponding PCT Application No. PCT/US12/56364 filed Sep. 20, 2012.

Debiotech Switzerland, Sales Brochure, Lausanne 9, Switzerland, distributed week of Dec. 1, 1996 at the Radiological Society of North American in Chicago, Illinois.

International Search Report from PCT Application No. PCT/US1998/02027.

(56) References Cited

OTHER PUBLICATIONS

The International Preliminary Report on Patentability from corresponding PCT Application No. PCT/US2012/056355 mailed Apr. 3, 2014.
The International Preliminary Report on Patentability from corresponding PCT Application No. PCT/US2012/056328 mailed Apr. 3, 2014.
The International Preliminary Report on Patentability from corresponding PCT Application No. PCT/US2012/056364 mailed Apr. 3, 2014.
The Extended/Supplementary European Search Report dated Jun. 3, 2015 from corresponding EP Application No. 12834408.2.
The Extended/Supplementary European Search Report dated Jun. 3, 2015 from corresponding EP Application No. 12832808.5.

\* cited by examiner

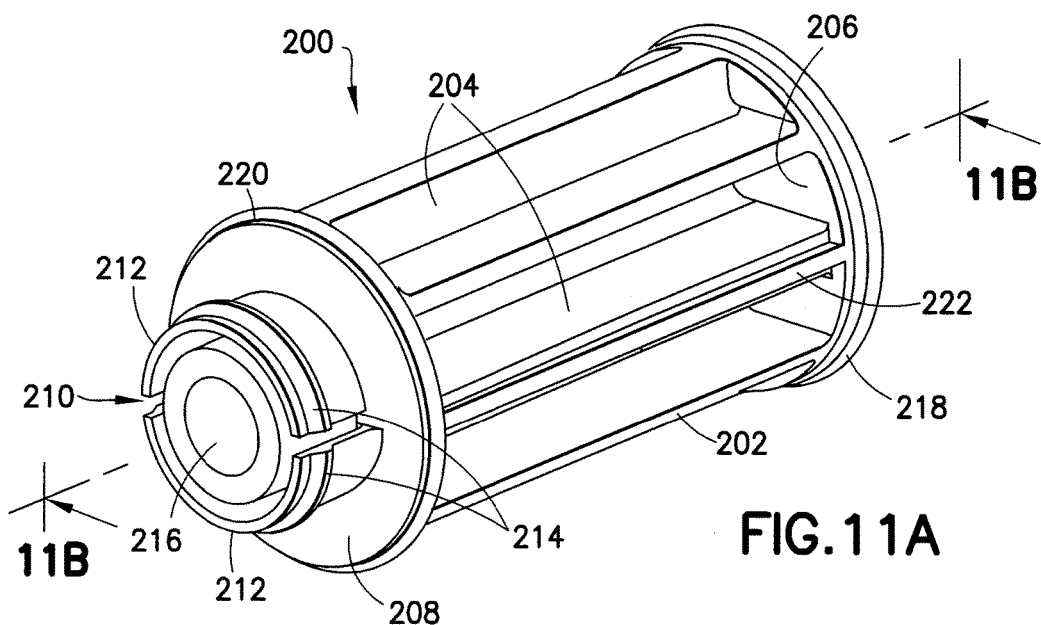
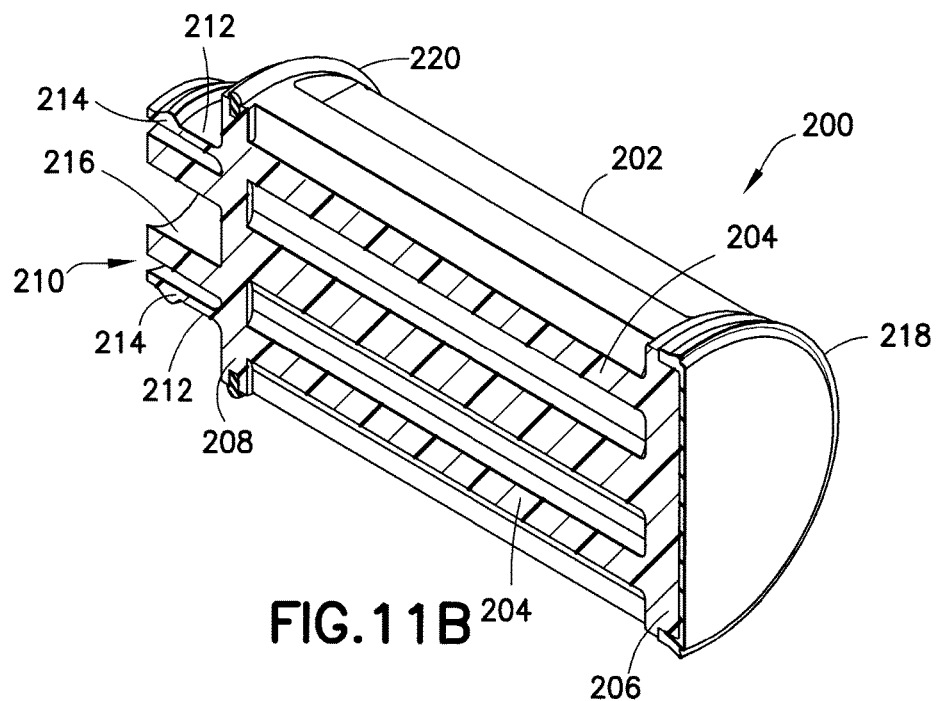

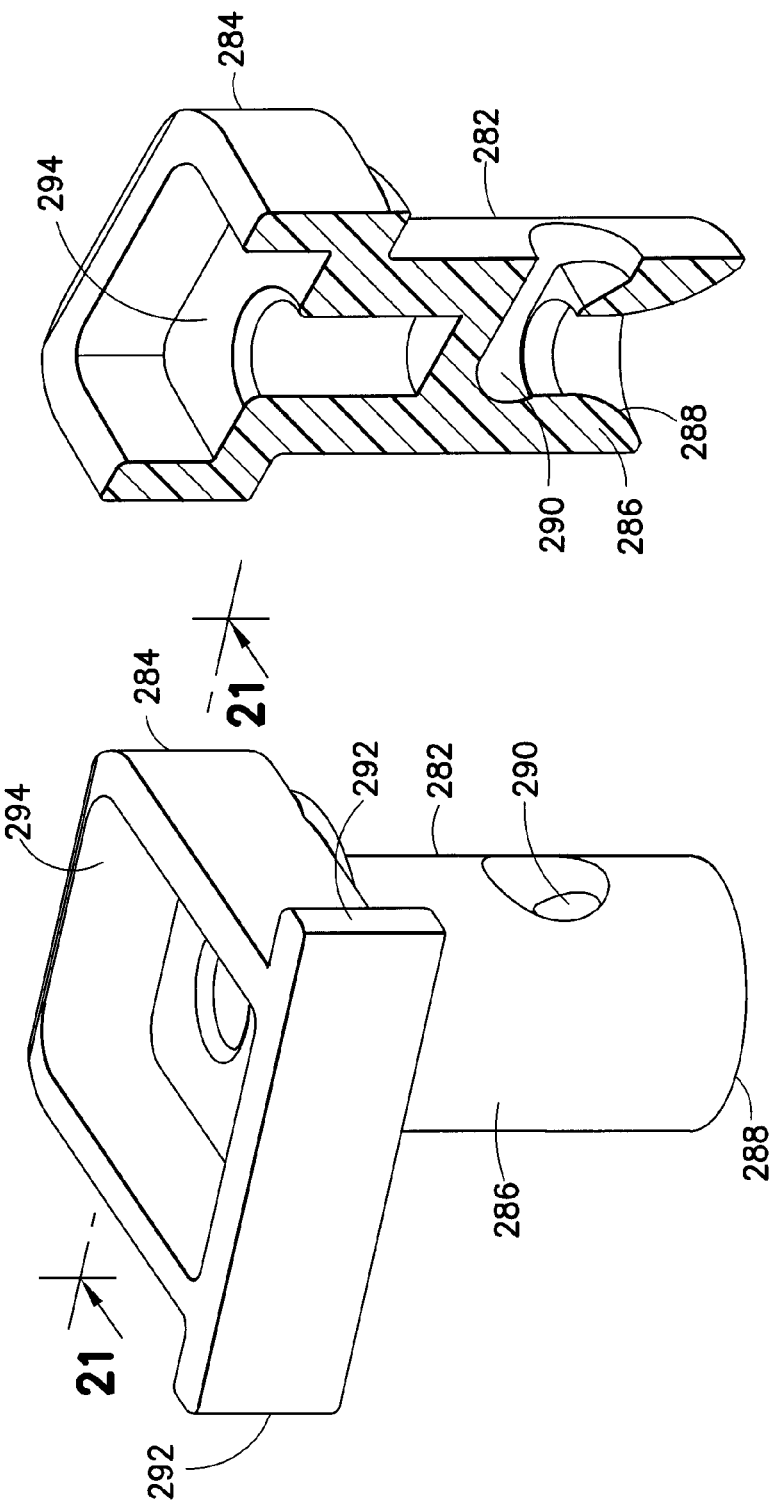

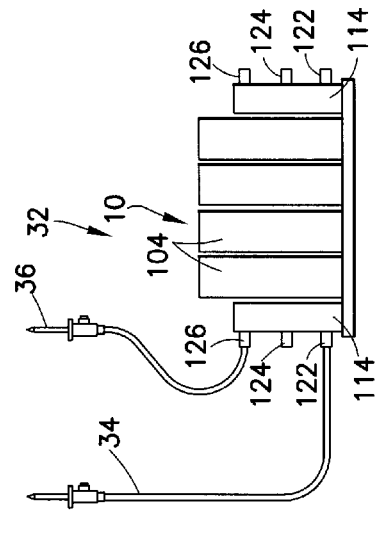
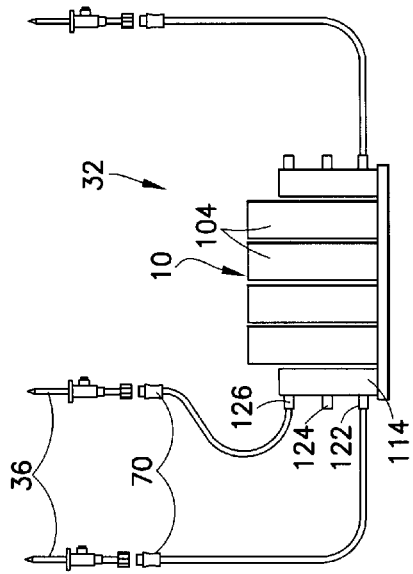
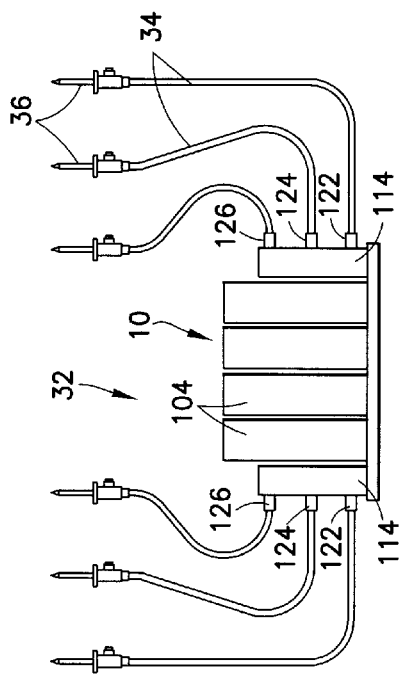
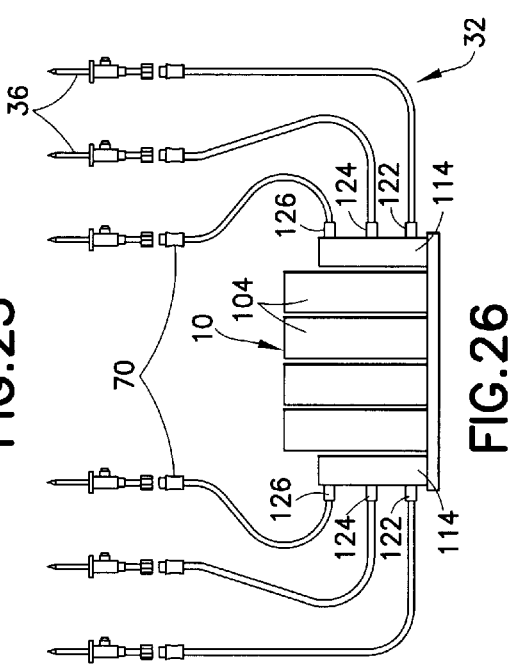

ASSEMBLY METHOD FOR A FLUID PUMP DEVICE FOR A CONTINUOUS MULTI-FLUID DELIVERY SYSTEM

CROSS REFERENCE TO RELATED APPLICATION

This Application is a 371 national phase application of PCT International Application No. PCT/US2012/056364, filed Sep. 20, 2012, and designating the United States of America, which claims the benefit from the earlier filed U.S. Provisional Application No. 61/537,371, filed Sep. 21, 2011, entitled "Continuous Multi-Fluid Delivery System and Method," and is hereby incorporated into this application by reference as if fully set forth herein.

BACKGROUND OF THE INVENTION

Field of the Invention

The field of the invention is related to a system and assembly method for a fluid pump device for use in a continuous multi-fluid delivery system having applications in medical diagnostic and therapeutic procedures wherein one or more fluids are infused/injected into a patient.

Description of Related Art

In the medical field, fluid delivery devices used to provide fluids to patients are generally well-known and exist in many different forms. A system commonly used for this purpose is a gravity-feed system wherein a fluid containing bag is supported above the level of the patient's body and wherein the flow rate to the patient is controlled by the gross pressure of a clamp upon the flexible tube extending between the bag and the patient. It will be readily understood that the flow rate of fluid through the tube is a function of the amount of constriction of the tube. Manually operated devices are known in the medical field for delivery of fluid under pressure to a patient. Examples of such manually-operated pumping devices are known from U.S. Pat. No. 3,464,359 to King et al.; U.S. Pat. No. 2,062,285 to Bergman; and U.S. Pat. No. 1,748,810 to Wandel, as examples.

Syringe-based infusion pumps and peristaltic pumps have also been used in the medical field for delivering fluids to patients under pressure and provide more precise control over the flow rate and volumetric delivery of fluids to patients. An example of a syringe pump adapted to deliver fluid to a patient is described in U.S. Pat. No. 5,529,463 to Layer et al., which discloses a multi-syringe pump for this purpose. A peristaltic pump system suitable for delivering a constant flow of fluid under pressure to a patient is described in U.S. Pat. Nos. 6,558,125 and 6,488,660, both to Futterknecht.

There are a number of medical procedures which require the delivery of fluids to a patient in a precisely controlled manner. One such application involves the delivery of contrast media fluid to a patient during a diagnostic computed tomography (CT) scan to provide enhanced x-ray images. Traditionally, such contrast media fluid has been delivered to the patient using a syringe-based injection system. Such injection systems require the contrast media fluid to be transferred from its original container to a disposable syringe. The injection system then pressurizes the fluid within the syringe to deliver the fluid to the patient at a controlled flow rate, precisely when needed. Some syringe-based injection systems are capable of accommodating two separate syringes to facilitate sequential or simultaneous delivery of two different types of fluid.

One limitation of a syringe-based fluid injection system is the need to refill and replace the disposable syringes prior to each patient procedure. U.S. Pat. No. 5,806,519 to Evans, III et al. describes a fluid delivery system which could be used to deliver fluid to multiple patients in succession without the need to refill and replace syringes for each patient. Another fluid delivery system that purports to overcome this limitation is disclosed in U.S. Pat. Nos. 6,558,125 and 6,488,660 (Futterknecht). These latter patents disclose a fluid delivery system that utilizes a peristaltic pump to deliver fluid directly from contrast media bottles to the patient. While this system eliminates the need to replace disposable syringes after each patient, the use of a roller-type peristaltic pump inherently limits the pressure capability of the system to approximately 200 psi. Unfortunately, many CT procedures and virtually all angiographic procedures require fluid to be delivered at higher pressures.

In order to provide more precise control of flow rates and volumetric delivery of fluids to patients, positive displacement pump platforms have been developed in the medical field. These devices eliminate the use of syringes and provide increased pressure ranges over peristaltic pumps. One such positive displacement pump device is disclosed in U.S. Pat. Nos. 5,196,197 and 6,197,000 to Reilly et al., which describe a system for the continuous delivery of contrast media fluid to a patient that uses a cam-driven multi-piston pump. Such a pump is capable of delivering fluids at relatively high pressures in a controlled manner. Another example of a positive displacement pump platform intended for use in delivering fluid to a patient undergoing a medical procedure is disclosed in International Publication No. WO 2006/056828, which discloses a volumetric pump with reciprocating and rotating pistons that are adapted to deliver a controlled and continuous flow rate of fluid during a medical procedure. Japanese Publication Nos. JP 61-42199 and JP 61-4220, both assigned to Nemoto Kiyourindou KK, disclose another multi-piston cylinder pump which enables the controlled and continuous delivery of fluids during a medical procedure.

There are several disadvantages present in positive displacement pump platforms known in the medical field for fluid delivery to a patient. One disadvantage is that these pump platforms are, typically, limited to pumping a single fluid type. Many medical procedures, such as CT procedures, often involve the use of a combination of contrast media fluid and saline delivered precisely to the region of interest within a patient's body. For example, after an initial injection of contrast media fluid is performed, a bolus of saline fluid may be administered to move the contrast fluid into the region of interest. In order to have the capability of delivering two or more different types of fluids, an external selection valve (such as a stopcock) must be added upstream of the pump inlet to allow the fluid delivery system to select from one of two (2) or more available fluid sources or possibly both if a mixing device is also provided. If two (2) interconnected pumps are present in the fluid delivery system, a downstream mixing device is required in such a two-pump system.

SUMMARY OF THE INVENTION

This disclosure presents exemplary embodiments of a fluid pump device for association with a drive and actuating system, exemplary embodiments of the drive and actuating system, and exemplary embodiments of a fluid delivery system comprising the drive and actuating system and fluid pump device. In one embodiment, the fluid pump device comprises a pump manifold, a plurality of pump cylinders extending proximally from the pump manifold and in selective fluid communication with the pump manifold, a plunger reciprocally operable within each of the pump cylinders, and an inlet selector valve to establish selective fluid communication between a fluid source container and the pump manifold to control fluid flow into the pump manifold. Each plunger is independently operable by the drive and actuating system.

A system and method of assembling a disposable fluid pump device is provided and includes providing initial settings for components of the fluid pump device, and encoding and labeling certain identifying information regarding the fluid pump device on the body of the fluid pump device. In one embodiment, a method of assembling a disposable fluid pump device, including a pump body having a plurality of pump cylinders and at least one inlet selector valve for controlling fluid input to the pump cylinders, includes the steps of identifying at least one initial inlet selector valve position; generating, with at least one processor, encoded data representing at least the at least one inlet selector valve position; and setting the at least one selector valve to the at least one initial inlet selector valve position.

The initial position may be an angular orientation of a valve stem associated with the at least one inlet selector valve. The method may also include identifying at least one pump input parameter, and the at least one pump input parameter may include at least one of a pump configuration/type number, a manufacturing batch number, a pump type identifier, a pump sequential identification number, or any combination thereof. Additionally, the pump sequential identification number may be determined by adding a starting pump sequential identification number with a count of previously assembled fluid pump devices.

The method may further include generating, with at least one processor, identifying indicia partially representing the encoded data, wherein the identifying indicia includes human-readable barcode, machine-readable barcode, matrix barcode, RFID tag, machine-readable label, human-readable label, programmable electronic memory, optical markings, or any combination thereof. The method may further involve placing the identifying indicia on an external surface of the pump body. Further, the at least one initial inlet selector valve position may differ from an inlet selector valve position corresponding with a used state of the fluid pump device. The at least one inlet selector valve may be automatically set by an automated insertion device. The method may also include inserting a valve stem of the at least one inlet selector valve in the at least one initial inlet selector valve position.

In another embodiment, a system for encoding data relating to a fluid pump device including a pump body having a plurality of pump cylinders and at least one inlet selector valve for controlling fluid input to the pump cylinders is disclosed. The system includes a manufacturing process computer configured to: determine at least one inlet selector valve position for the fluid pump device; and generate encoded data based at least partially on an encoding algorithm and the at least one inlet selector valve position, such that at least the at least one inlet selector valve position number may be determined by decoding the encoded data.

The encoded data may be generated based at least partially on at least one of a pump configuration/type number, a manufacturing batch number, a pump type identifier, a pump sequential identification number, or any combination thereof. The manufacturing process computer may be further configured to generate identifying indicia representing the encoded data. Additionally, the identifying indicia may include a human-readable barcode, machine-readable barcode, matrix barcode, RFID tag, machine-readable label, human-readable label, programmable electronic memory, optical markings, or any combination thereof. Further, the pump sequential identification number may be determined by adding a starting pump sequential identification number with a count of previously assembled fluid pump devices.

The encoding algorithm of the system may further comprise an asymmetrical encryption algorithm. The encoding algorithm may be based at least partially on a first key, and a decoding algorithm for decoding the encoded data may be based at least in part on a second key, where the second key is different than the first key.

In a further embodiment, a method for identifying a fluid pump device including at least one inlet selector valve for controlling fluid movement includes the steps of determining an initial position of the at least one inlet selector valve; generating encoded data with at least one processor based at least in part on the initial position of the at least one selector valve; and providing the fluid pump device with the encoded data.

At least a portion of the encoded data may be generated with at least one encryption algorithm. The encryption algorithm may generate the encoded data based at least partially on a first encryption key. The encoded data may be configured to be decrypted with at least one decryption algorithm. The at least one decryption algorithm may use a second encryption key, which may be different than the first encryption key. The initial position of the at least one inlet selector valve may comprise an angular orientation of a valve stem of the at least one inlet selector valve. The method may further include the steps of generating identifying indicia based at least partially on the encoded data; and marking the fluid pump device with the identifying indicia. The identifying indicia may comprise a human-readable barcode, machine-readable barcode, matrix barcode, RFID transponder, machine-readable label, human-readable label, programmable electronic memory, optical markings, or any combination thereof. The encoded data may represent at least one of a pump configuration/type number, a manufacturing batch number, a pump type identifier, a pump sequential identification number, or any combination thereof.

In yet a further embodiment, a method for preparing a fluid pump device for use with a fluid delivery system, the fluid pump device including at least one into selector valve comprising a valve stem and an inlet selector valve cylinder, the at least one inlet selector valve controlling fluid movement into the fluid pump device, includes the steps of determining an initial angular orientation of the valve stem of the at least one inlet selector valve; and inserting the valve stem into the inlet selector valve cylinder such that the valve stem is in the initial angular orientation in the inlet selector valve cylinder.

The fluid pump device may be marked with identifying indicia comprising a human-readable barcode, machine-readable barcode, matrix barcode, RFID transponder, machine-readable label, human-readable label, programmable electronic memory, optical markings, or any combination thereof. The identifying indicia may include encoded data, and the at least one inlet selector valve position may be determined based at least partially by decoding the encoded data. The encoded data may be generated based at least partially on a first key value, and the encoded data may be decoded based at least partially on a second key value. The method may further include determining at least one pump input parameter based at least partially on the identifying indicia, wherein the at least one pump input parameter comprises at least one of a pump configuration/type number, a manufacturing batch number, a pump type identifier, a pump sequential identification number, or any combination thereof.

In another embodiment, a method of assembling a fluid pump device includes the steps of providing a pump body including a plurality of pump cylinders; and at least one inlet selector valve cylinder laterally outboard of the pump cylinders; inserting an inlet selector valve stem into the inlet selector valve cylinder such that the valve stem is in a predetermined angular orientation in the inlet selector valve cylinder; and inserting respective plungers into the pump cylinders.

The pump body may further include a saline manifold extending across the pump cylinders and defining at least one saline channel, and the method may further include installing a saline manifold cap onto the pump body to enclose the at least one saline channel. The pump body may also include a front plate and the pump cylinders may extend proximally from the front plate, and the method may further include installing a manifold plate onto the front plate to form a pump manifold. The method may further include capturing at least one check valve between the manifold plate and the front plate during the step of installing the manifold plate onto the front plate to form the pump manifold.

The front plate may include at least one inlet manifold channel defined by at least one channel member, and the method may further include installing an inlet manifold cap on the at least one channel member to enclose the at least one inlet manifold channel. Additionally, the manifold plate may comprise an outlet selector valve cylinder, and the method may further include inserting an outlet selector valve stem into the outlet selector valve cylinder. The outlet selector valve cylinder may include a patient outlet port and a waste outlet port and the valve stem of the outlet selector valve body may define a flow passage, and the step of inserting the outlet selector valve stem into the outlet selector valve cylinder may include aligning the flow passage to be in fluid communication with the waste outlet port.

Further, the step of inserting the outlet selector valve stem into the outlet selector valve cylinder may be preceded by spraying lubricant onto the interior wall surface of the outlet selector valve cylinder. The method may further include spraying lubricant onto the interior wall surface of the pump cylinders and onto the interior surface of the at least one inlet selector valve cylinders prior to the steps of inserting the inlet selector valve stem into the inlet selector valve cylinder and inserting the respective plungers into the pump cylinders. The steps of inserting the inlet selector valve stem into the inlet selector valve cylinder and inserting the respective plungers into the pump cylinders may occur concurrently. Additionally, the predetermined angular orientation of the valve stem of the inlet selector valve body may be encoded in identifying indicia provided on the pump body. The identifying indicia may include a bar code.

The method may further include generating an inlet selector valve position number and encoding the inlet selector valve position number as identifying indicia provided on the pump body. The inlet selector valve position number may correspond to the predetermined angular orientation of the inlet selector valve stem in the inlet selector valve cylinder. The method may further include etching the identifying indicia on one of the pump cylinders.

Further details and advantages of the various embodiments described in detail herein will become clear upon reviewing the following detailed description of the various embodiments in conjunction with the accompanying drawing figures.

BRIEF DESCRIPTION OF THE DRAWINGS

FIG. 11A is a rear perspective view of a plunger for the fluid pump device shown in FIG. 2.

FIG. 11B is a cross-sectional view taken along line 12-12 in FIG. 11A.

FIG. 20 is an isolation perspective view of an outlet selector valve stem used in the fluid pump device shown in FIG. 2.

FIG. 21 is a cross-sectional perspective view taken along line 21-21 in FIG. 20.

FIG. 25 is a schematic view showing the fluid pump device of FIG. 2 with a first or basic embodiment of a fluid supply set associated with the fluid pump device.

FIG. 26 is a schematic view showing the fluid pump device of FIG. 2 with a second or high-use embodiment of the fluid supply set associated with the fluid pump device.

FIG. 27 is a schematic view showing the fluid pump device of FIG. 2 with a third or limited-use embodiment of the fluid supply set associated with the fluid pump device.

FIG. 28 is a schematic view showing the fluid pump device of FIG. 2 with a fourth and additional limited-use embodiment of the fluid supply set associated with the fluid pump device that may be used with single-patient fluid source containers.

DESCRIPTION OF THE PREFERRED EMBODIMENTS

Figure 1:
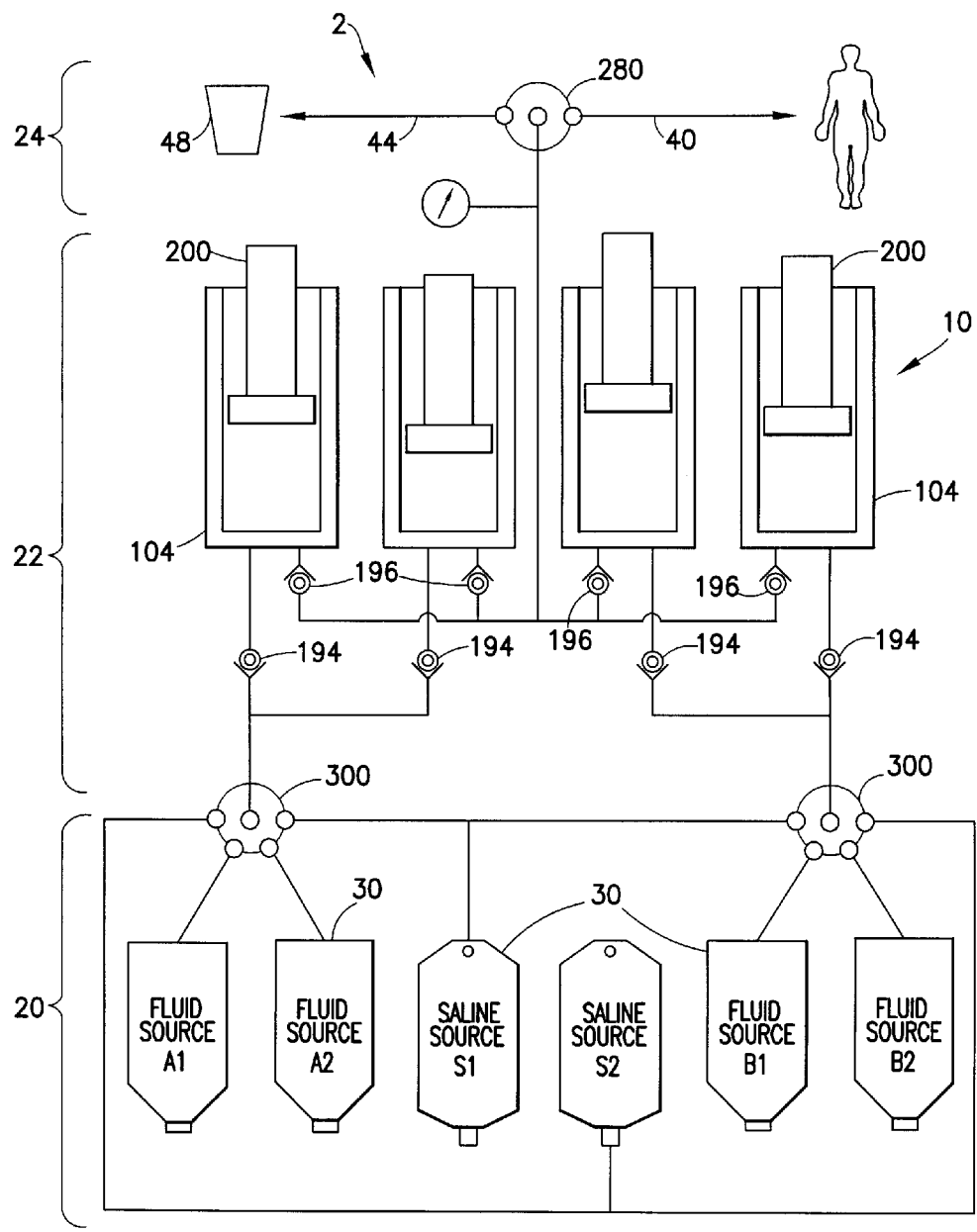
FIG. 1 is a schematic view of a fluid delivery system for continuous multi-fluid delivery applications.

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific components, devices, features, and operational sequences illustrated in the accompanying drawing figures and described herein are simply exemplary and should not be considered as limiting.

Referring initially to FIGS. 1-6, a fluid pump device 10, generally provided in the form of a disposable pump cassette, is shown. While fluid pump device or pump cassette 10 (hereinafter referred to as "pump 10") is intended as a disposable component, the pump 10 is intended for multiple uses prior to disposal. Such multiple uses may be for multiple patients or for a multiple and discrete number of uses in medical diagnostic and therapeutic procedures which may involve a single or multiple patients. The pump 10 is adapted to interface with a drive and actuating system (not shown) that accepts, drives, and actuates various components on the pump 10, and a control system (not shown) is also provided to control operation of the various components of the drive and actuating system.

The pump 10 may be considered to have a front or distal side 12, a rear or proximal side 14, a right side 16 as viewed looking from the front or distal side 12 toward the rear or proximal side 14, and a left side 18 as viewed looking from the front or distal side 12 toward the rear or proximal side 14. Generally, as shown schematically in FIG. 1, the pump 10 may be part of a fluid delivery system 2 which includes the drive and actuating system. The pump 10 generally comprises a fluid supply section 20, a pump metering and pressurizing section 22, and a pump outlet section 24. The fluid supply section 20 includes one or more fluid source containers 30 containing various fluids to be supplied to the pump 10, and a fluid supply set that conducts the one or more fluids to the pump 10 and may be configured to meet different patient and/or procedural needs. The pump outlet section 24 includes a disposable single-use or single-patient disposable supply set 40 ("SPDS") used to make a fluid connection, such as to a catheter inserted into a patient to convey a desired fluid or mixture of fluids to a desired location within a patient's body. Additionally, the pump outlet section 24 comprises a waste collection system 44 that is associated with the pump 10 to collect and store waste fluids. The waste collection system 44 generally comprises a waste collection tube set 46 connected to a waste collection container 48, also shown in FIG. 29.

The pump 10 forms a part of the pump metering and pressurizing section 22. The pump 10 generally comprises a pump manifold 80, a pump body 100, a plurality of independently operable plungers 200 operatively associated with the pump body 100, a pump manifold plate 230 which is joined to the pump body 100 to form the pump manifold 80, an outlet selector valve 280 associated with the pump body 100 for controlling fluid delivery or output from the pump 10, and a plurality of inlet selector valves 300 associated with the pump body 100 for controlling fluid flow to the pump body 100. In operation, the pump 10 is typically interfaced with multiple and different fluids contained in the fluid source containers 30, and is actuated or operated by the drive and actuating system to select a fluid type from the several fluid source containers 30 and continuously deliver fluids, either individually or as a fluid mixture, to the patient. The pump 10 draws in fluid directly from the fluid source containers 30 and accurately meters the appropriate volumes and specified fluid flow rates and infusion time to the patient via the patient supply set 40.

Referring additionally to FIGS. 7-10, the pump body 100 is typically formed as an integral or singular body formed from polycarbonate and like polymeric materials via an injection molding process. The pump body 100 comprises a front or distal plate 102 and a plurality of pump cylinders 104 extending proximally from the front plate 102. In the illustrated embodiment, a total of four (4) pump cylinders 104 are provided in the pump 10, with the two (2) right side pump cylinders 104 providing one fluid circuit and the two (2) left side pump cylinders 104 providing a second fluid circuit. While of four (4) pump cylinders 104 are provided in the pump 10, the pump 10 may be "scalable" to include additional pairs of pump cylinders 104 or may be provided with just two (2) tandem pump cylinders 104. While the pump cylinders 104 are preferred to have a cylindrical shape, they may also have other symmetrical or non-symmetrical cross-sectional shapes (such as D-shaped) in vertical or transverse cross-section. Each pump cylinder 104 defines a pump chamber 106 and accepts a plunger 200 which is reciprocally operable within the pump cylinder 104. The plungers 200 are independently operable by the drive and actuating system. The respective pump cylinders 104 each have an interior wall or surface 108 that defines the pump chamber 106. The pump cylinders 104 each have a generally enclosed front or distal end wall 110 formed by the front plate 102 and an open rear or proximal end 112.

Additionally, the pump body 100 comprises a plurality of inlet selector valve cylinders 114 that extend proximally from the front plate 102 laterally outboard of the two (2) outer pump cylinders 104. Each inlet selector valve cylinder 114 defines a cylindrical chamber 116 that accepts an inlet selector valve 300 which is rotationally operable within the inlet selector valve cylinder 114. The drive and actuating system also independently operates the respective inlet selector valves 300 disposed within the inlet selector valve cylinders 114. In the illustrated embodiment, two (2) inlet selector valve cylinders 114 are provided in pump 10 to respectively control inflow to the two (2) "right side" pump cylinders 104 providing one fluid circuit and the two (2) "left side" pump cylinders 104 providing the second fluid circuit in pump 10. The respective inlet selector valve cylinders 114 have a front or distal end opening 118 formed in the front plate 102 and a rear or proximal end opening 120 to accept the inlet selector valve 300.

Each inlet selector valve cylinder 114 comprises, in the illustrated embodiment, a pair of inlet ports 122, 124 for use in connecting the pump 10 to two (2) fluid sources of diagnostic or therapeutic (e.g., pharmaceutical) fluids, such as imaging contrast media, to be received in the pump chambers 106 of the pump cylinders 104. Further, each inlet selector valve cylinder 114 comprises, in the illustrated embodiment, an additional rear or proximal inlet port 126 for use in connecting the pump 10 to, typically, a source of flushing or diluting fluid such as saline. As such, the rearmost inlet port 126 is referred to hereinafter as a "saline port 126", while inlet ports 122, 124 are referred to hereinafter as "first and second inlet ports 122, 124", respectively. The inlet ports 122, 124, 126 are axially spaced along the inlet selector valve cylinder 114, with the first inlet port 122 located near the front plate 102 and the saline port 126 located near the rear or proximal end opening 120 of the inlet selector valve cylinder 114. The saline port 126 is located at a lower level than the first and second inlet ports 122, 124, and connects to a saline manifold located on the underside of the pump body 100. Accordingly, the saline port 126 is located at a lower level and opens into the inlet selector valve cylinder 114 and the saline manifold 130 to access one of two (2) saline channels in the saline manifold 130, rather than intersecting or directly opposing the valve body of the inlet selector valve 300 as in the case of the first and second inlet ports 122, 124. The first and second inlet ports 122, 124 and the saline ports 126 on the inlet selector valve cylinders 114 may be formed with luer-type connector tips or barbed connection tips, and like fluid connections arrangements, for making either removable or permanent fluid connections to the fluid supply tubes 34 used to connect the pump 10 to the one or more fluid source containers 30 that provide therapeutic or diagnostic (e.g., pharmaceutical) fluids or saline to the pump 10.

The illustrated embodiment of the pump 10 is shown for exemplary purposes with six (6) supply ports, three (3) on each of the right and left sides 16, 18 of the pump 10. These supply ports include the two (2) right side inlet ports 122, 124 and the right side saline port 126 on the pump body 100 and the two (2) left side inlet ports 122, 124 and the left side saline port 126 on the pump body 100. However, this specific configuration is illustrated for expediency in explaining the various components, features, and desirable operational characteristics of the pump 10 and should be considered as non-limiting. Accordingly, the pump 10 may comprise a fewer or a greater number of ports 122, 124, 126 on each side 16, 18, as desired.

The saline port 126 on the respective inlet selector valve cylinders 114 is in fluid communication with a saline manifold 130 that extends across the underside of the pump body 100 and across the pump cylinders 104. The saline manifold 130 is oriented generally parallel to the front plate 102. The saline manifold 130 is typically adapted to be placed in fluid communication via the two (2) saline ports 126 to two (2) sources of saline S1, S2 contained in two (2) respective fluid source containers 30. The saline manifold 130 is bifurcated into two (2) saline channels 132, 134. The respective inlet selector valves 300 are configured so that saline may be drawn from either of the sources of S1, S2 in the saline fluid source containers 30 via the saline channels 132, 134, even though the saline fluid source container 30 may be physically on the opposite side of the pump 10 from the inlet selector valve 300, as described further herein. In the illustrated embodiment of the pump 10, the forward or distal or "first" saline channel 132 of the saline manifold 130 is supplied by the saline source S2 in the fluid source container 30 connected to the saline port 126 located on the right side inlet selector valve cylinder 114, and the rear or proximal or "second" saline channel 134 of the saline manifold 130 is supplied by the saline source S1 in the fluid source container 30 connected to the saline port 126 located on the left side inlet selector valve cylinder 114. The shape of the saline channels 132, 134 may be formed with smooth interior surfaces and curvatures to minimize the potential for trapped air and pressure drop (e.g., flow restriction) through each saline channel 132, 134. A saline manifold cap 136 encloses the saline channels 132, 134 and may be secured in place on the saline manifold 130 formed on the underside of the pump body 100 via medical grade adhesive, solvent bonding, laser and ultrasonic welding, and like joining techniques.

As the forward saline channel 132 is connected to the right saline source S2 and the rear saline channel 134 is connected to the left saline source S1, it is desirable to purge air using saline from the left saline source S1 as this is the rearmost saline channel. By using the rearmost saline channel 134 connected to the left saline source S1 for fluid priming operations, the fluid passages in the pump 10 may be primed from rear to front with saline, and air is purged forward from the rear of each of the inlet selector valves 300. This result occurs because there are no other ports "behind" the rearmost saline channel 134. For example, it would not be possible to purge all of the air from the inlet selector valves 300 if one of the inlet ports 122, 124 was used to supply a priming fluid. This is because there would be a "dead space" in the inlet selector valve 300 behind the two (2) front inlet ports 122, 124 through which no fluid would flow. Any air in this portion of the inlet selector valve 300 would remain after priming.

Figure 9:
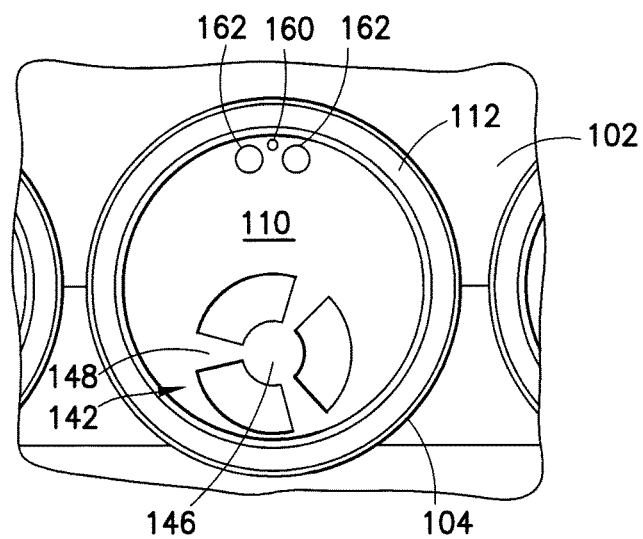
FIG. 9 is a rear view of a pump cylinder of the pump body shown in FIG. 7.
Figure 10:
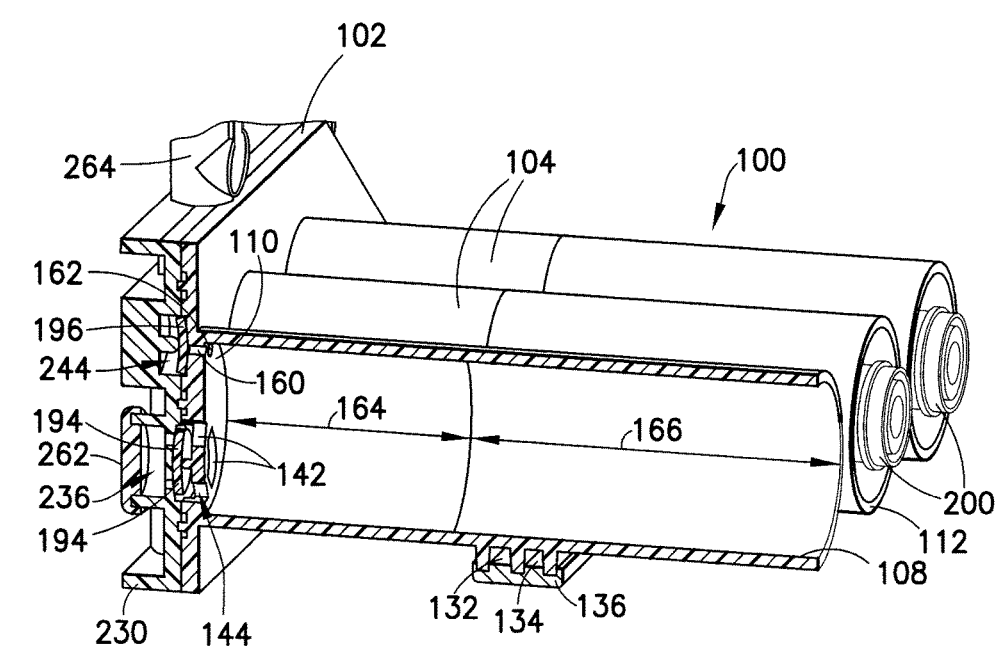
FIG. 10 is a cross-sectional view of the fluid pump device taken along line 10-10 in FIG. 2 and with a plunger of the fluid pump device removed for clarity.
Figure 12A:
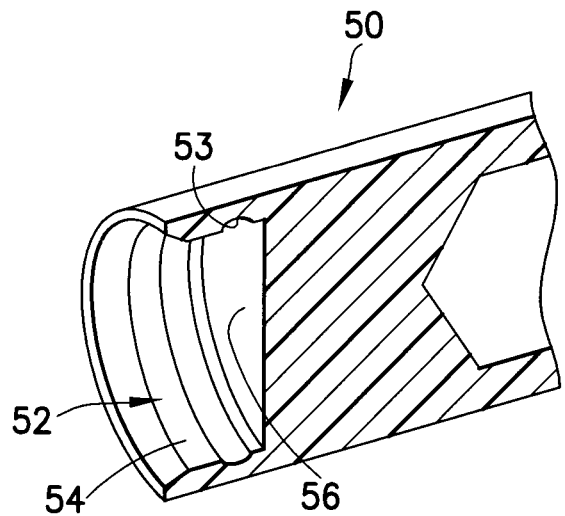
FIG. 12A is a longitudinal cross-sectional perspective view of a terminal end of a drive piston adapted to engage the plunger shown in FIGS. 11A-11B.
Figure 12B:
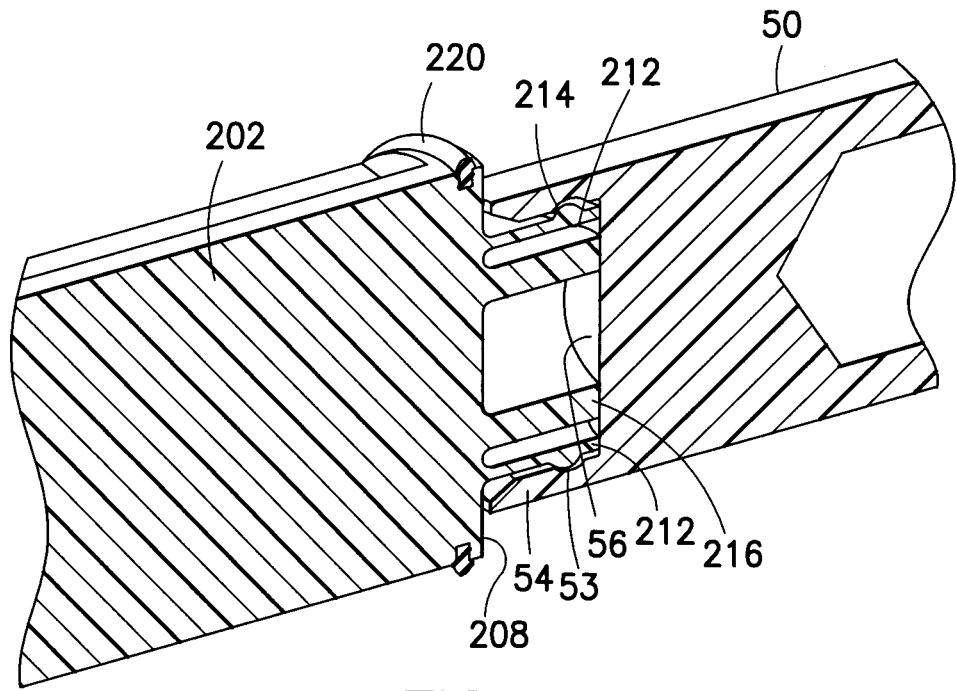
FIG. 12B is a cross-sectional perspective view of the terminal end of the drive piston shown in FIG. 12A interfaced with the proximal end of the plunger shown in FIGS. 11A-11B.
Figure 13:
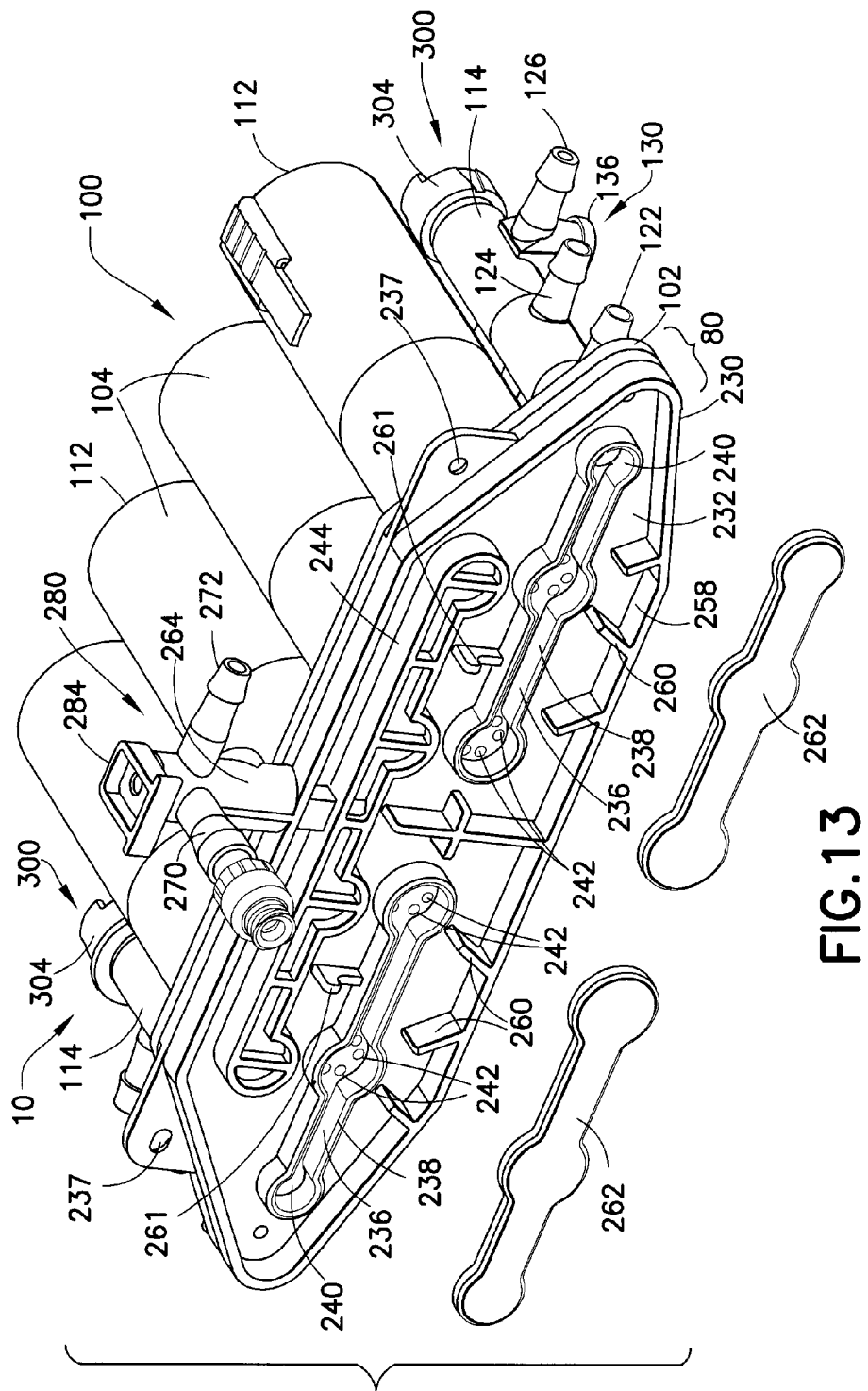
FIG. 13 is a perspective view of the fluid pump device showing inlet manifold caps exploded from the fluid pump device.
Figure 14:
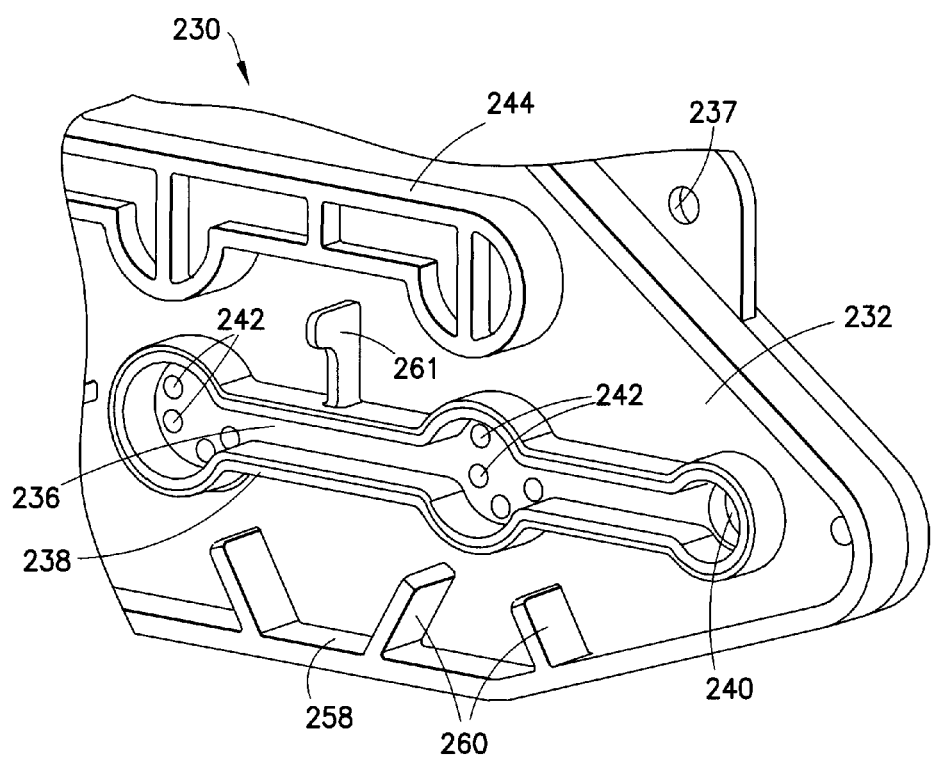
FIG. 14 is a perspective view of a right front portion of a pump manifold plate adapted for association with the pump body shown in FIG. 7.
Figure 15:
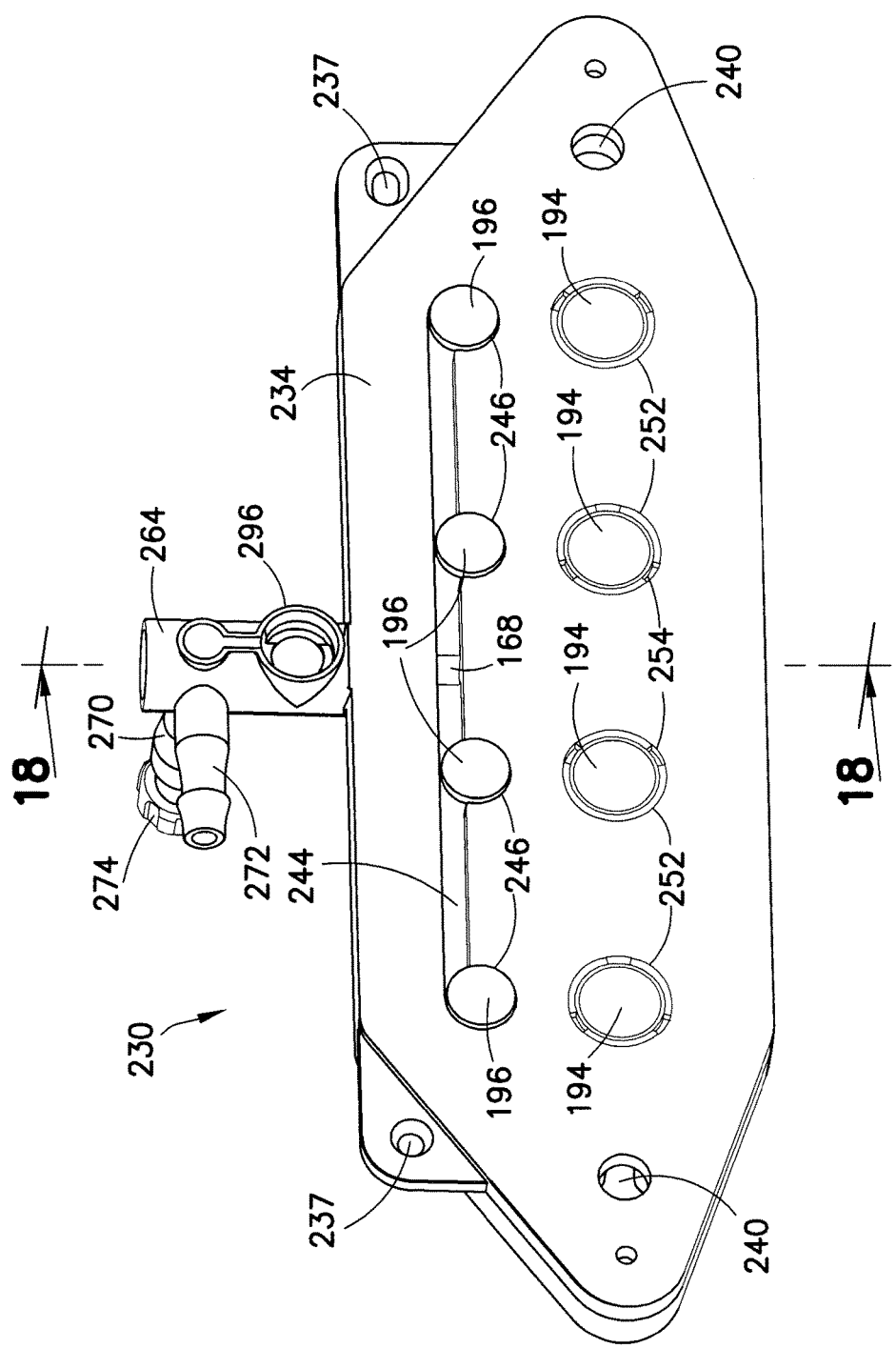
FIG. 15 is a rear perspective view of the pump manifold plate supporting inlet and outlet check valves of the fluid pump device.
Figure 16:
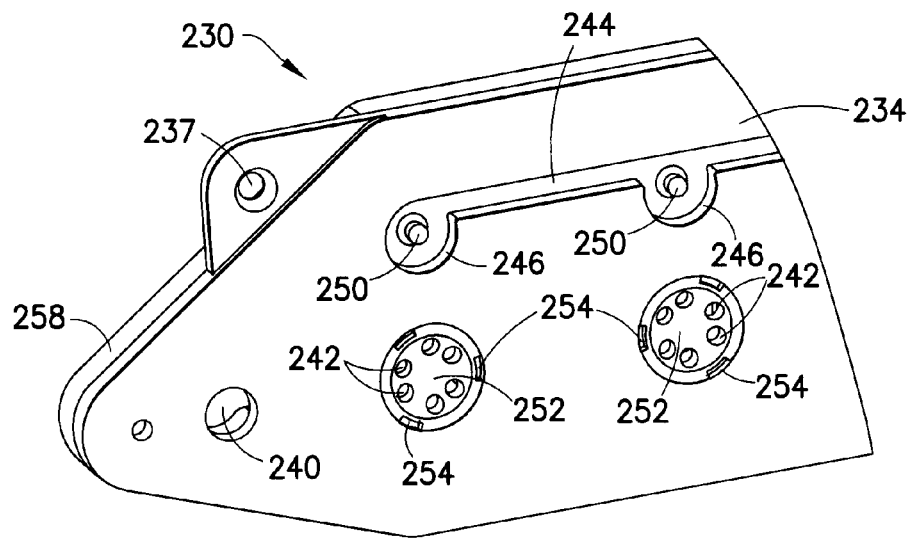
FIG. 16 is a rear perspective view of a right portion of a pump manifold plate adapted for association with the pump body shown in FIG. 7.
Figure 17:
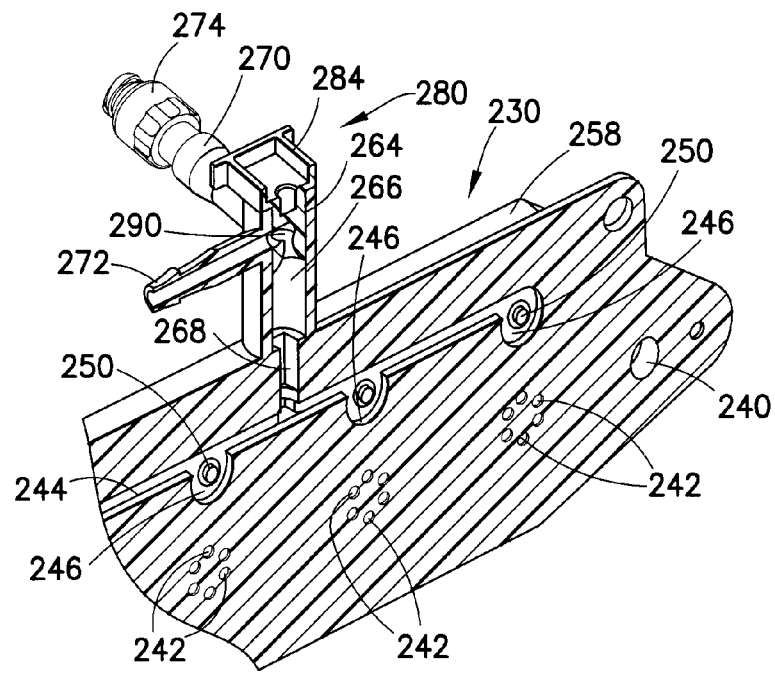
FIG. 17 is a longitudinal cross-sectional and perspective view of a portion of the pump manifold plate adapted for association with the pump body shown in FIG. 7.
Figure 18:
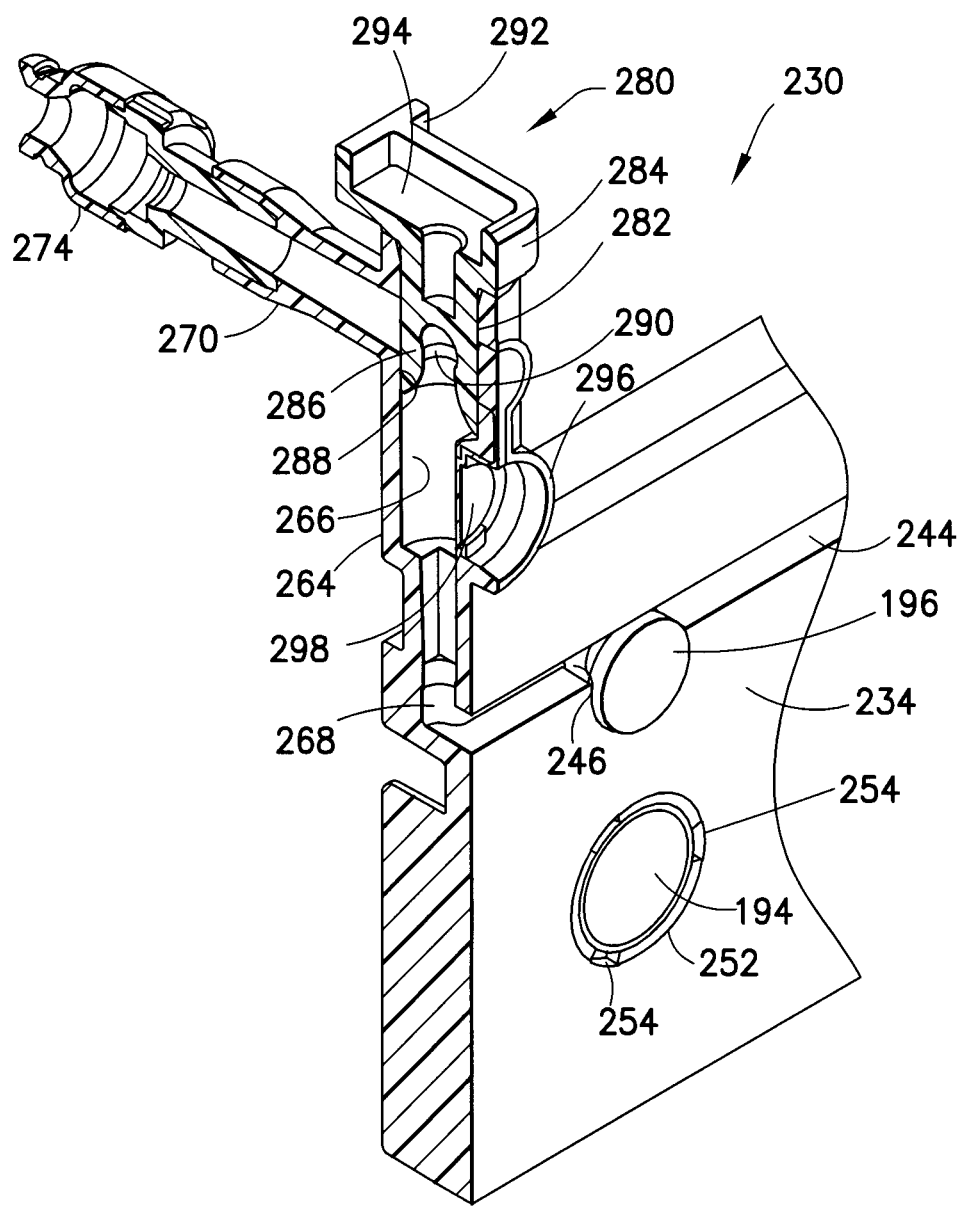
FIG. 18 is a cross-sectional perspective view taken along line 18-18 in FIG. 15.
Figure 19:
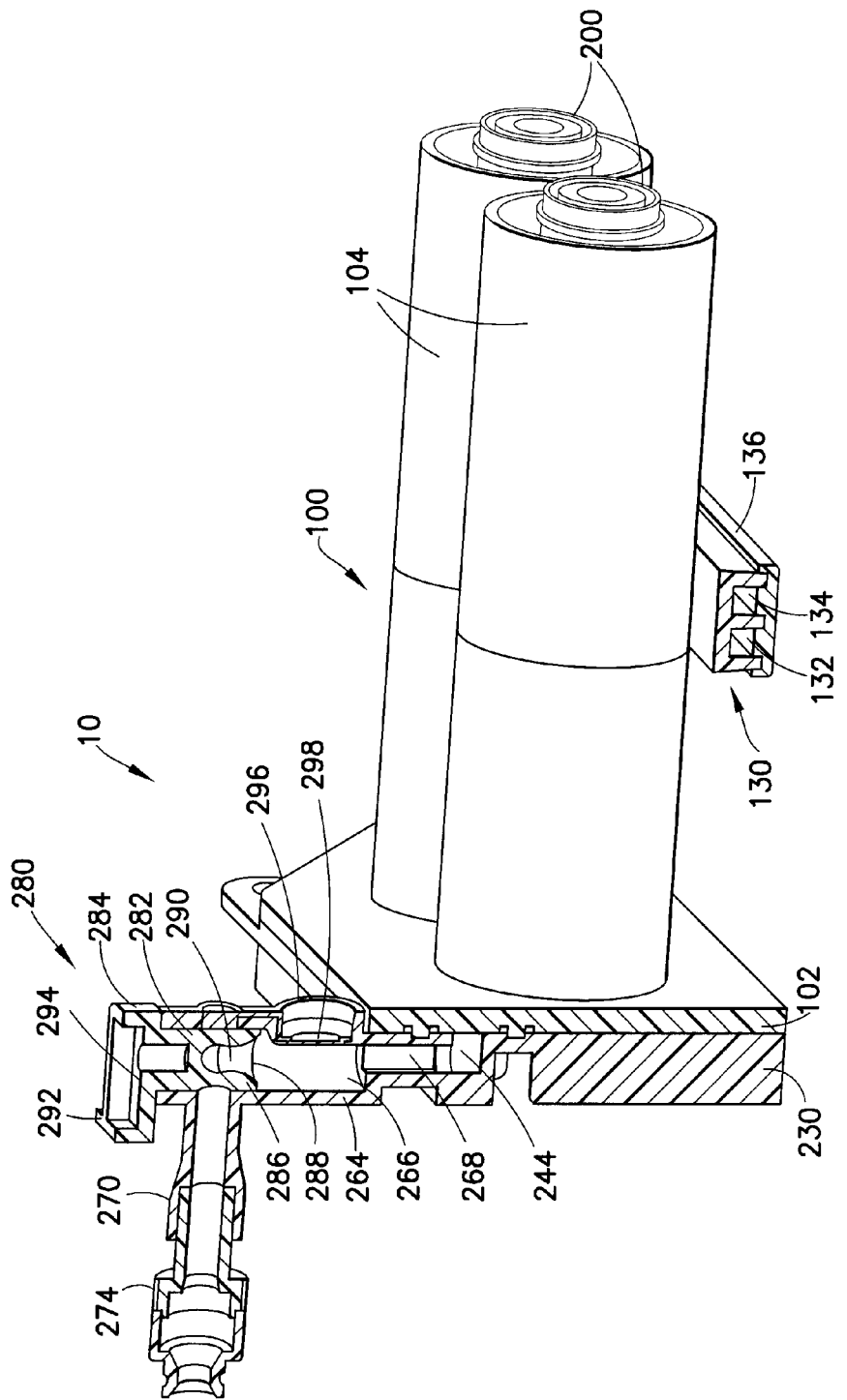
FIG. 19 is a cross-sectional perspective view taken along line 19-19 in FIG. 3.
Figure 22:
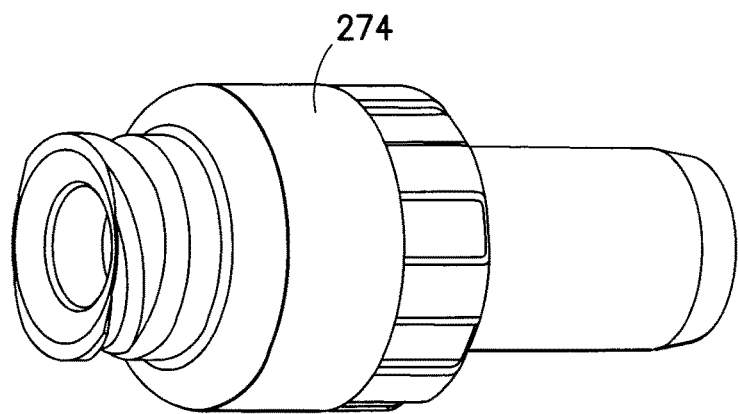
FIG. 22 is an isometric perspective view of a swabable valve for use in association with the outlet selector valve shown in FIG. 19.

A front or distal side 140 of the front plate 102 defines a plurality of inlet openings 142, one for each of the pump cylinders 104. The inlet openings 142 are provided in the distal end wall 110 of each of the pump cylinders 104. The inlet openings 142 permit fluid to enter the pump chamber 106 of the respective pump cylinders 104. The inlet openings 142 are spaced apart on the front plate 102 to respectively coincide with the pump chambers 106 of the respective pump cylinders 104. Accordingly, four (4) spaced inlet openings 142 are provided in the illustrated embodiment, one for each pump cylinder 104, and are positioned to be near the bottom center of each of the pump cylinders 104, as shown in FIG. 9. An inlet check valve support structure 144 is provided in each of the inlet openings 142 and is desirably recessed within each of the inlet openings 142 for supporting an inlet check valve 194. The inlet check valves 194 are flexible polymeric, typically polyurethane, disks that regulate the fluid flow into each pump cylinder 104. The inlet check valve support structure 144 comprises a central hub 146 and one or more prongs 148 extending radially outward from the central hub 146. A total of three (3) prongs 148 is present in the inlet check valve support structure 144 in the illustrated embodiment. The central hub 146 desirably includes a centrally-located preload pin 150 that allows a preload force to be applied to the inlet check valve 194 to ensure that the inlet check valve 194 closes when there is no pressure gradient present across the inlet check valve 194. The preload force is not set too high so as to overly increase the "cracking" or opening pressure of the inlet check valve 194 as this would undesirably cause a higher pressure drop across the check valve 194. The preload pins 150 also help to counteract the effects of long-term storage, which could cause the inlet check valves 194 to develop a compression set over time. The front or distal end openings 118 in the front plate 102 leading to the inlet selector valve cylinders 114 are circumferentially bordered by one or more concentric ribs or rims 152 formed on the front side 140 of the front plate 102 and which extend around the front or distal end openings 118.

The front side 140 of the front plate 102 further defines an elongated recess 154 extending across the front side 140 above the elevational location of the inlet openings 142, but still coinciding with the pump chambers 106 of the respective pump cylinders 104. The elongated recess 154 is bordered by a perimetrical recess 156 so that a sealing element, such as an elongated O-ring or gasket or like sealing element, may be placed in the perimetrical recess 156 and form a fluid sealing border about the elongated recess 154. A plurality of recessed areas 158 is defined in the elongated recess 154 and is spaced apart in the elongated recess 154 to coincide, respectively, with the pump chamber 106 defined by the pump cylinders 104. Accordingly, a total of four (4) recessed areas 158 is provided in the illustrated embodiment. Each recessed area 158 typically defines at least one top or air egress opening 160 in the distal end wall 110 of each of the pump cylinders 104, and is desirably positioned to be near the top center of each of the pump cylinders 104, as shown in FIG. 9, for providing an egress opening for air bubbles in the pump chambers 106 of the respective pump cylinders 104. Each of the recessed areas 158 further defines one or more outlet openings 162 in the front plate 102, typically on either side of the top air egress opening 160, and in the distal end wall 110 of each of the pump cylinders 104 to permit fluid to exit the respective pump cylinders 104. It is also noted that the upper surface or leg of the elongated recess 154 is substantially flat and horizontal and its centerline is raised slightly above the recessed areas 158 which allows any air that is present in the elongated recess 154 to be ejected upward through the outlet selector valve 280.

A plate support structure or groove 168 may be provided on at least one of the pump cylinders 104, such as provided on a top or upper facing side of one of the outboard pump cylinders 104. The plate support structure 168 supports a pump indicator plate 170 which is encoded with identifying information regarding the pump 10 to enable the control system which controls operation of the drive and actuating system to determine, for example, the configuration of the pump 10. The configuration of the pump 10 is dependent, typically, on the type or configuration of the fluid supply set as manufactured or associated with the pump 10 and used to meet different patient and/or procedural needs.

Figure 2:
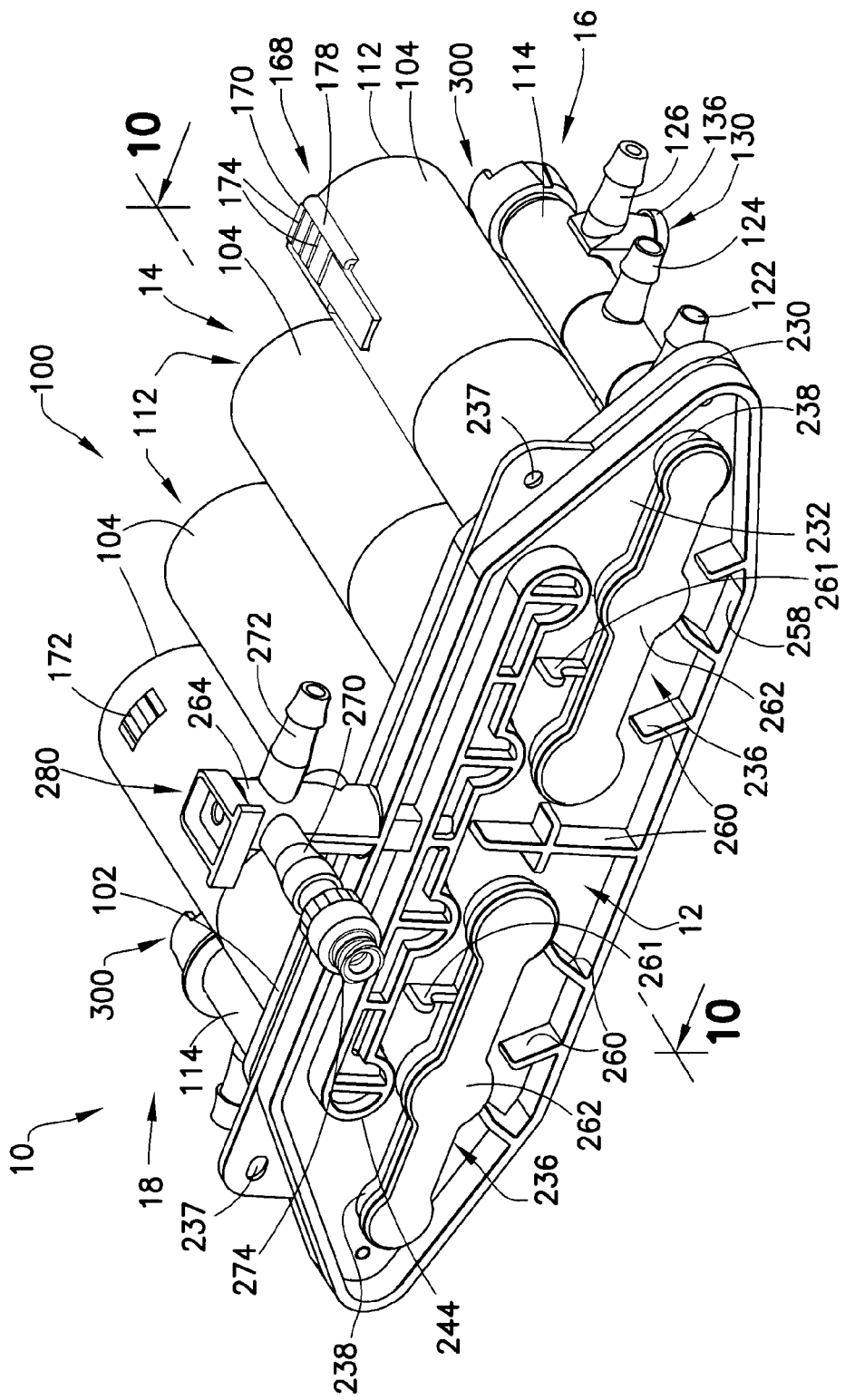
FIG. 2 is a front perspective view of a fluid pump device for use in the fluid delivery system shown in FIG. 1.
Figure 3:
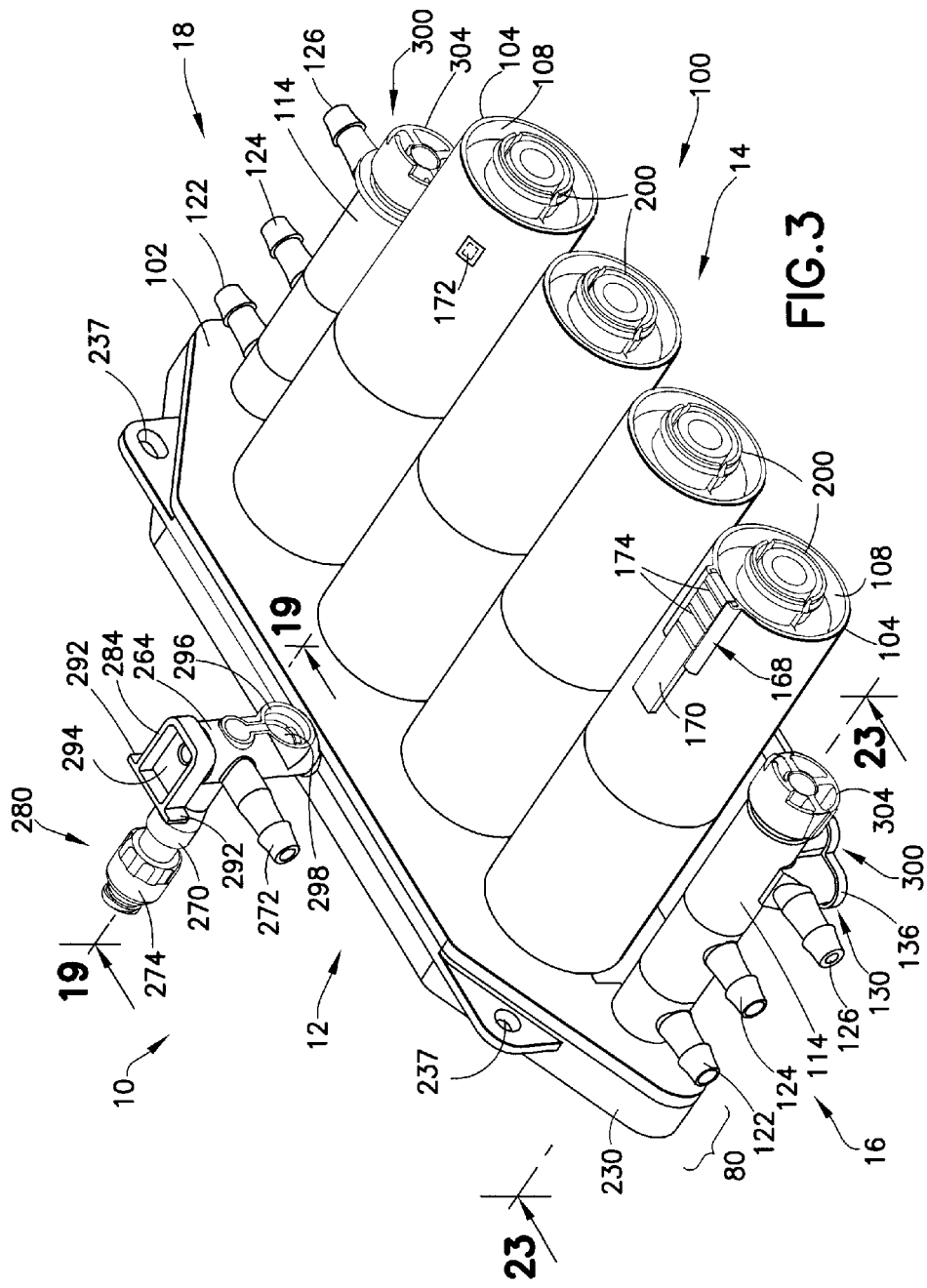
FIG. 3 is a rear perspective view of the fluid pump device shown in FIG. 2.
Figure 4:
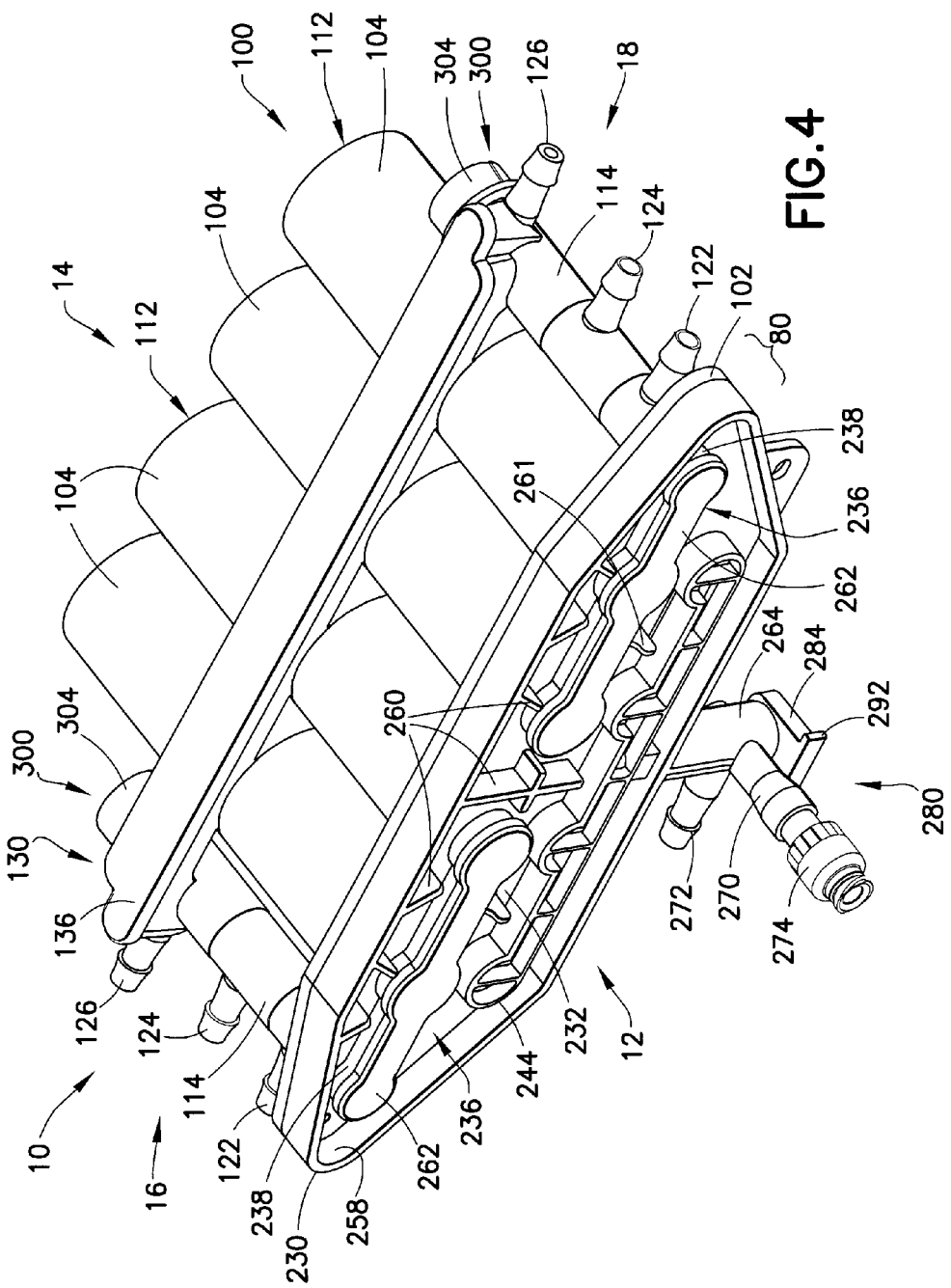
FIG. 4 is a bottom perspective view of the fluid pump device shown in FIG. 2.

The configuration of the pump 10 may also, or alternatively, be encoded into identifying indicia 172, such as bar code indicia as shown in FIG. 2, that is affixed on or etched into a top or upper facing side of one of the pump cylinders 104, such as affixed on or etched into the opposite outboard pump cylinder 104 from the pump cylinder 104 carrying the pump indicator plate 170. It will be understood that the pump indicator plate 170 and identifying indicia 172 may be located on any suitable surface or location on the pump body 100 or on the pump manifold plate 230. The identifying indicia 172 may also be a suitable RFID (radio frequency identification) tag, as shown in FIG. 3, as a suitable arrangement for storing pertinent information about the pump 10. The identifying indicia 172 is scanned prior to installation of the pump 10 in association with the drive and actuating system to determine the configuration of the pump 10, and other identifying information. The pump indicator plate 170 and/or the identifying indicia 172 may contain additional pertinent information, such as pump serial number, manufacturing identification number, use-by date, manufacturing lot code/batch number, initial angular orientation of the inlet selector valves 300 in their respective inlet selector valve cylinders 114 on the pump body 100, cryptographic hash code to confirm validity of information, and like information. More limited information may be carried by the pump indicator plate 170 than the identifying indicia 172, with the identifying indicia 172 typically including all of the foregoing information. Thus, the pump indicator plate 170 may alternatively be encoded with only limited information, such as pump type information to identify the specific configuration of the pump 10. Moreover, if the identifying indicia 172 is an RFID (radio frequency identification device) tag, the RFID tag or device can store the same information listed above, such as: pump type/configuration, pump serial number, manufacturing identification number, use-by date, manufacturing lot code/batch number, and initial angular orientation of the inlet selector valves 300 in their respective inlet selector valve cylinders 114 on the pump body 100. Because RFID tags can have read/write capability, the RFID tag could also store information on how many times the "tagged" pump 10 has been used, the volume of pumped fluid, peak pressure, and like operational information. The RFID tag may be located on any suitable surface of the pump 10 and can be read and written to by an antenna in close proximity to the pump 10, such as associated with the drive and actuating system.

The pump indicator plate 170 is typically provided as an optically encoded transparent polymeric member that fits within and is secured by the plate support structure 168. The indicator plate 170 provides a length of material disposed along at least a portion of the wall. The length of material propogates electromagnetic energy therethrough. The length of material may include at least two indicators or grooves 174, each of the grooves being located at a different predetermined longitudinal position along the length of material and each of the grooves being positioned to longitudinally align with a sensor when a barrel, such as one of the pump cylinders 104, is engaged with a drive and actuating system (not shown) used to operate the pump 10 and thereby attached to the fluid injector portion of the fluid delivery system 2. The pump indicator plate 170 comprises a series of grooves 174 that permits at least the configuration of the pump 10 to be optically read or verified after installation in association with a drive and actuating system used to operate the pump 10. Thus, the drive and actuating system may include an optical detector and like technology and the pump indicator plate 170 may be provided and encoded with information in accordance with the disclosures of U.S. Pat. Nos. 7,018,363 and 7,462,166, both to Cowan et al., which disclose optical technology for determining configuration, including size of a fluid pumping component mounted to a power fluid injector and are incorporated herein by reference in their entirety for these and any other pertinent applications. The foregoing Cowan patents are generally directed to syringes and like pump devices such that the optical technology therein may be applied to the pump cylinders 104 of the pump 10. The pump cylinders 104 are analogous and operable generally in the same manner as cylindrical syringe bodies and like pump devices as disclosed in the foregoing Cowan patents. Thus, the optical technology described in the foregoing Cowan patents may be applied to the pump cylinders 104 whereby the pump indicator plate 170 is provided with the optical technology detailed in these patents or the pump cylinders 104 are marked or otherwise identified in the various manners and embodiments disclosed in these patents. The pump indicator plate 170 is provided as an exemplary element for applying the indentifying indicia 172 to the pump 10 and should not be deemed limiting as this application expressly includes application of the optical technology found in the foregoing Cowan patents to the pump 10 generally and the pump body 100 in particular. The pump body 100 may be opaque to absorb laser light during a laser welding process during assembly of the pump 10, but the opaque pump body 100 also helps with optical sensor performance in the optical reading of the information contained in the grooves 174 in the pump indicator plate 170. Additionally, the plate support structure 168 may be adapted for a snap-lock fit with the pump indicator plate 170. The plate support structure 168 may comprise a recessed groove 176 in the pump cylinder 104 for accepting the pump indicator plate 170, and a pair of flanges 178 for restraining the pump indicator plate 170 in the groove 176. Further, the snap-lock fit may be provided by a snap-lock tab 180 formed within the groove 176 in the pump cylinder 104 and a corresponding mating recess (not shown) defined in the underside of the pump indicator plate 170.

Referring further to FIGS. 11A-12B, as noted previously, a plunger 200 is reciprocally operable within each of the pump cylinders 104 and is independently controlled by the drive and actuating system. Each plunger 200 comprises a rigid plunger body 202 that is injection molded from polycarbonate and like polymeric materials. The plunger body 202 may be a unitary, solid body formed to include a series of wall segments 204 that extend between a front or distal end disc 206 and a rear or proximal end disc 208. The rear or proximal end disc 208 is formed with a piston interface member or device 210 which is adapted to interface with an independent drive piston associated with the drive and actuating system for the pump 10. The piston interface member 210 is split into at least two (2) parts or halves to form opposing halves or legs 212 that may compress towards one another, or radially inward toward a central longitudinal axis of the plunger 200, to be received in a distal end recess or socket 52 in the drive piston 50. Additionally, the piston interface member 210 comprises a circumferential radial lip or rim 214, which is provided on each of the interface halves or legs 212, to engage a corresponding groove or recess 53 defined proximally inward from radial lip or rim 54 provided in the distal end socket 52 in the drive piston 50. The engaging lips or rims 54, 214 secure the engagement between the plunger 200 and drive piston 50. Thus, the rear or proximal end disc 208 of each plunger body 202 includes several features that allow the plunger 200 to "snap" into the distal end socket 52 in the actuating drive piston 50. A desirable result of the foregoing "snap-fit" connection is that it is non-orientation specific and the drive piston 50 may engage the plunger 200 in any radial orientation of the plunger 200. Moreover, it will be understood that the piston interface member 210 may be split into a plurality of portions or parts 212 that may compress inwardly toward a central longitudinal axis of the plunger 200. Additionally, the piston interface member 210 may be generally cylindrical shaped and, as such, the plurality of portions or parts may be formed as arcuate sections or segments.

Once the plunger 200 is "snapped" into place in association with the drive piston 50, the drive piston 50 can move the plunger 200 in a reciprocal manner in the associated pump cylinder 104. When the plunger 200 is pressurizing fluid in the pump chamber 106 of the pump cylinder 104 by moving forward or distally in the pump cylinder 104, a central ring or cylinder support member 216 extending proximally from the rear or proximal end disc 208 seats against a flat interior end or bottom 56 of the distal end socket 52 in the actuating drive piston 50, thereby transferring the compressive axial load to the drive piston 50. The support member 216 coaxially disposed in the piston interface member 212. When the pump 10 is to be removed from the drive and actuating system, the drive piston 50 is retracted rearward or proximally until the rear or proximal end disc 208 of the plunger body 202 contacts a stationary projection. Further retraction of the drive piston 50 disengages the snap-fit interface between the piston interface member 210 and the drive piston 50.

Each plunger 200 comprises two (2) over-molded seals, a front or distal end lip seal 218 provided circumferentially about and on the front side of the front or distal end disc 206, and a rear or proximal bead seal 220 provided circumferentially about the rear or proximal end disc 208. The front end disc 206 with over-molded lip seal 218 is used to seal liquid within the pumping zone 164 of the pump cylinder 104, and the rear end disc 208 with over-molded bead seal 220 is used to prevent wetted portions of the interior wall 108 of the pump cylinder 104 from being exposed to the ambient environment. The seals 218, 220 may be made of polyurethane and like polymeric materials. The front lip seal 218 is desirably adapted to withstand fluid pressure of at least 400 psi and, desirably, at least 500 psi and is desirably hydraulically energized by fluid pressure. Accordingly, higher pressures result in greater sealing force. The rear bead seal 220 typically seals against dust and particulates that may be pulled into the open rear or proximal end 112 of the pump cylinder 104, and is actuated by compression within the isolation zone 166 of the pump cylinder 104. Seal runners 222 may extend from the front lip seal 218 to the rear bead seal 220 along two (2) or more or all of the wall segments 204. In the illustrated embodiment, seal runners 222 extend along two (2) of the wall segments 204 located on opposite lateral sides of the plunger body 202. The seal runners 222 are typically formed during the over-molding process used to form the front lip seal 218 and the rear bead seal 220 on the front and rear end discs 206, 208, respectively. The "flat" front of the front end disc 206 is desirable for minimizing residual fluid volume in the pump chamber 106 of the pump cylinder 104, helps to eject air bubbles from the pump chamber 106 during fluid priming of the pump 10 and, further, helps clean the pump chamber 106 during flushing procedures.

Referring additionally to FIGS. 13-17, the pump 10, as noted previously, comprises a pump manifold 80 that is formed by the connection or joining of the pump manifold plate 230 with the pump body 100. The pump manifold 80 is generally formed by assembling the pump manifold plate 230 to front plate 102 of the pump body 100. The pump manifold plate 230 (hereinafter "manifold plate 230") comprises a front or distal side 232 and a rear or proximal side 234. The manifold plate 230 is generally shaped to correspond to the shape of the front plate 102 of the pump body 100 and is joined with the front plate 102 so that the rear side 234 of the manifold plate 230 is in engagement with the front side 140 of the front plate 102. The front side 232 of the manifold plate 230 includes right and left inlet manifold channels 236 provided on lateral right and left halves of the manifold plate 230. The inlet manifold channels 236 generally extend longitudinally along the front side 232 of the manifold plate 230. The two inlet manifold channels 236 correspond, respectively, to the two (2) right side pump cylinders 104 and the two (2) left side pump cylinders 104 of the pump body 100. As noted previously, in the illustrated embodiment, a total of four (4) pump cylinders 104 is provided in pump 10, with the two (2) "right" side pump cylinders 104 providing one fluid circuit and the two (2) "left" side pump cylinders 104 providing a second fluid circuit. The "right" inlet manifold channel 236 corresponds to the two (2) "right" side pump cylinders 104, and the "left" inlet manifold channel 236 corresponds to the two (2) "left" side pump cylinders 104. Alignment slots or holes 237 may be provided in the manifold plate 230 to facilitate loading of the pump 10 in association with the drive and actuating system.

Each of the right and left inlet manifold channels 236 is defined by a raised channel member or flange wall 238 provided on the front side 232 of the manifold plate 230. The manifold plate 230 defines a lateral opening 240 in each of the inlet manifold channels 236 that coincides with the distal or front end opening 118 in the front plate 102 of the pump body 100 which leads to the inlet selector valve cylinder 114. Accordingly, each lateral opening 240 registers with a corresponding front end opening 118 to place the "right" and "left" inlet selector valves 300 in fluid communication with the corresponding "right" and "left" inlet manifold channels 236, respectively. Additionally, the manifold plate 230 defines two (2) sets of inlet openings 242 in each of the right and left inlet manifold channels 236 that correspond to the inlet openings 142 in the front plate 102 of the pump body 100. As noted previously, the inlet openings 142 are spaced apart on the front plate 102 to respectively coincide with the pump chambers 106 of the respective pump cylinders 104, and the inlet openings 142 are positioned to be near the bottom center of each of the pump cylinders 104, as shown in FIG. 9. The respective sets of inlet openings 242 are, desirably, a plurality of openings 242 arranged in a predetermined pattern, such as a circular pattern, and enable fluid communication with the inlet openings 142 in the front plate 102 of the pump body 100. However, the two (2) sets of inlet openings 242 in each inlet manifold channel 236 may alternatively be provided as two (2) singular large openings in the respective inlet manifold channels 236. The illustrated circular arrangement of the inlet openings 242 desirably includes at least one inlet opening 242 located at a "high" point, such as near to the top part of the channel member 238 defining the inlet manifold channel 236. This "high point" inlet opening 242 minimizes the potential for air bubbles to become trapped within the inlet manifold channels 236 because any air present in the inlet manifold channels 236 is pulled into the pump cylinders 104 during the initial fluid priming process for the pump 10. The number and size of inlet openings 242 may be selected to minimize pressure drop across the underlying inlet check valves 194 during filling of the pump cylinders 104, while minimizing the potential for high pressures in the pump cylinders 104 which could cause the polymeric material of the inlet check valves 194 to "extrude" into the inlet openings 242 under high pressure.

The rear or proximal side 234 of the manifold plate 230 also defines an elongated outlet manifold channel or recess 244 extending across the rear side 234 above the elevational location of the sets of inlet openings 242 in the manifold plate 230, but still coinciding with or corresponding to the pump chambers 106 of the respective pump cylinders 104. The outlet manifold channel 244 generally corresponds to the elongated recess 154 defined in the front side 140 of the front plate 102 of the pump body 100. The elongated recess 154 is sized larger than the outlet manifold channel 244 and is bordered by the perimetrical recess 156, as described previously, so that an elongated O-ring or gasket and the like, may be placed in the perimetrical recess 156 and form a fluid sealing border around the outlet manifold channel 244 when the manifold plate 230 is joined to the front plate 102 of the pump body 100 to form the pump manifold 80. In a variation of the foregoing sealing arrangement, a weld joint, typically a laser weld, occupies the location of the perimetrical recess 156 and the sealing O-ring or gasket is not required, and this embodiment or variation is illustrated in the accompanying figures. The elongated recess 154 also forms the back wall of the outlet manifold channel 244 when the manifold plate 230 is joined to the front plate 102 of the pump body 100.

The outlet manifold channel 244 is used to place the respective pump cylinders 104 in fluid communication with the outlet selector valve 280 on the manifold plate 230. A plurality of outlet check valve receiving recesses 246 is defined as part of the outlet manifold channel 244. The outlet check valve receiving recesses 246 are spaced apart in the outlet manifold channel 244. Each of the receiving recesses 246 accommodates an outlet check valve 196. Thus, an outlet check valve receiving recess 246 is provided for each of the pump cylinders 104 of the pump body 100 so that an outlet check valve 196 opposes each of the respective sets of air egress openings 160 and outlet openings 162 in the front plate 102 of the pump body 100. The outlet check valve receiving recesses 246 are located directly above the sets of inlet openings 242 defined in the manifold plate 230, respectively. Each of the outlet check valve receiving recesses 246 further includes a centrally located preload pin 250 that allows a preload force to be applied to the outlet check valve 196 to ensure that the outlet check valve 196 closes when there is no pressure gradient present across the outlet check valve 196. The outlet check valves 196 are flexible polymeric discs, typically polyurethane discs, which regulate the fluid flow from each pump cylinder 104. Thus, the outlet check valves 196 are located within the respective outlet check valve receiving recesses 246 in the outlet manifold channel 244, with each of the outlet check valves 196 associated, respectively, with a corresponding set of outlet openings 162 and top openings 160 in the front plate 102 leading to the pump chambers 106 of the pump cylinders 104.

The rear or proximal side 234 of the manifold plate 230 further comprises dish-shaped areas or recesses 252 opposite the inlet openings 142 in the front plate 102 leading to the pump chambers 106 of the pump cylinders 104. The dish-shaped areas or recesses 252 form valve seats for the respective inlet check valves 194. As shown, for example, in FIG. 7, the perimetrical recess 156, which extends around the elongated recess 154 defined in the front side 140 of the front plate 102 of the pump body 100, also extends around or borders each of the inlet openings 142. Thus, the inlet openings 142 may be sealed by the same sealing element, such as an O-ring, gasket, or weld, disposed about the elongated recess 154, to form a fluid sealing border around the respective dish-shaped recessed areas 252. The sealing element (e.g., O-ring, gasket, or weld) forms a fluid sealing border around the outlet manifold channel 244 and the respective dish-shaped recessed areas 252 when the manifold plate 230 is joined to the front plate 102 of the pump body 100 to form the pump manifold 80. As noted previously, a welded joint, a laser or ultrasonic weld, is preferred in the location of the perimetrical recess 156 in the accompanying figures.

As described previously, the inlet check valves 194 are held in place in the opposing inlet openings 142 by the respective inlet check valve support structure 144 provided on the front plate 102 of the pump body 100. One or more receiving slots 254 may further be provided in the rear side 234 of the manifold plate 230 and located at spaced circumferential locations around the dish-shaped recesses 252. The one or more receiving slots 254 are adapted to receive corresponding tabs 256 extending from the radial prongs 148 of the inlet check valve support structures 144 provided on the opposing front plate 102 of the pump body 100, thereby securing the inlet check valves 194 opposite the dish-shaped recesses 252 formed in the rear or proximal side 234 of the manifold plate 230. A further purpose of the tabs 256 is to maintain the inlet check valves 194 centered relative to the inlet openings 142. Generally, it is desirable to provide some clearance between the disc edge of the inlet check valves 194 and the wall of the inlet openings 142 to permit fluid to flow past the inlet check valves 194 when opened. The three small tabs 256 keep the inlet check valves 194 centered during operation while leaving most of their circumference free from contact with the wall of the inlet openings 142.

The front side 232 of the manifold plate 230 comprises an outer circumferential flange or channel 258 which forms a border around the front side 232 of the manifold plate 230, and a series of stiffening ribs 260. The outer flange 258 and stiffening ribs 260 stiffen or provide rigidity to the pump manifold 80 without increasing the thickness of the molded polymeric material forming the pump body 100 and the manifold plate 230. Additionally, the outer flange 258 and the stiffening ribs 260 transfer the clamping force that is applied by the drive and actuating system to the welded joints that are subjected to high stress. Moreover, the outer flange 258 and stiffening ribs 260 may also be used for orienting and positioning the pump 10 in association with the drive and actuating system used to operate the pump 10. The stiffening ribs 260 may be located on the face of the front side 232 of the manifold plate 230, or be formed as part of the outer flange 258 on the front side 232 of the manifold plate 230. A pair of positioning or stiffening tabs 261 may be provided on each of the respective channel members 238 defining the inlet manifold channels 236, and disposed generally between the two (2) circular sets of inlet openings 242 in inlet manifold channels 236. The stiffening tabs 261 help to prevent deflection of the ends of the pump cylinders 104 when they are subjected to internal fluid pressure, for example, on the order of at least 400 psi and, often, at least 500 psi and greater. Manifold caps 262 are provided for each of the right and left inlet manifold channels 236 and are secured to the respective channel members 238 defining the inlet manifold channels 236 via an ultrasonic or laser welding process and like joining techniques.

The manifold plate 230 is joined to the front side 140 of the front plate 102 of the pump body 100 via a laser welding process and like joining process. This laser welding process secures the manifold plate 230 to the front plate 102 of the pump body 100 and forms a hermetic seal around the fluid paths defined between the manifold plate 230 and the front plate 102. As a result of this laser welding process, the respective sets of inlet openings 242 in the manifold plate 230 are placed in correspondence with the respective inlet openings 142 in the front plate 102 of the pump body 100 to provide fluid communication (across the separating inlet check valves 194) between the right and left inlet manifold channels 236 and the two (2) right and the two (2) left pump cylinders 104, respectively. Further, the laser welding process secures the inlet check valves 194 in association with the respective dish-shaped recesses 252 which form the valve seats for the inlet check valves 194. The inlet check valves 194 are held in place in the inlet openings 142 by the respective inlet check valve support structures 144, as mentioned previously. Additionally, the laser welding process secures the engaging tabs 256 associated with the radial prongs 148 of the inlet check valve support structures 144 in their corresponding receiving slots 254 in the rear proximal side 234 of the manifold plate 230, thereby further securing and aligning the inlet check valves 194 in the dish-shaped recesses 252 forming the valve seats for the inlet check valves 194. Moreover, the laser welding process places the outlet manifold channel 244 in fluid communication (across the separating outlet check valves 196) with the respective sets of outlet openings 162 and top openings 160 in the front plate 102 to permit fluid to exit the pump chambers 106 of the respective pump cylinders 104 and enter the outlet manifold channel 244. The outlet check valves 196 are similarly secured and aligned in the outlet check valve receiving recesses 246 in the outlet manifold channel 244 and opposite the plurality of recessed areas 158 defined in the elongated recess 154 on the front side 140 of the front plate 100 during the laser welding process. The plurality of recessed areas 158 forms the valve seats for the respective outlet check valves 196 in a similar manner to the way the dish-shaped recesses 252 form valve seats for the inlet check valves 194. Furthermore, the laser welding process provides a weld joint in the perimetrical recess 156, described previously, which forms a fluid sealing border around the outlet manifold channel 244 and the respective dish-shaped recessed areas 252 when the manifold plate 230 is joined to the front plate 102 of the pump body 100.

Referring additionally to FIGS. 18-22, the manifold plate 230 further comprises an outlet selector valve cylinder 264 extending upward from a top portion of the manifold plate 230 and, in particular, upward from the outer flange 258 which forms a border around the front side 232 of the manifold plate 230. The outlet selector valve cylinder 264 defines a valve bore 266 to accept the body of the outlet selector valve 280 therein. The valve bore 266 and a connecting passage 268 thereto are desirably located above the outlet manifold channel 244, permitting any air that is initially trapped in the outlet manifold channel 244 to rise up into the connecting passage 268 and valve bore 266 during the fluid priming process.

The outlet selector valve 280 controls fluid delivery or output from the pump 10. The valve bore 266 is in fluid communication with the outlet manifold channel 244 via the connecting passage 268. The outlet selector valve cylinder 264 further defines a pair of outlet ports 270, 272, including a patient outlet port 270 that accepts a swabable valve 274 and a waste outlet port 272. The swabable valve 274 may be secured within the patient outlet port 270 via medical grade adhesive, solvent bonding, laser and ultrasonic welding, and like joining techniques. As an alternative, the patient port 270 may be overmolded around the stem of the swabable valve 274, which eliminates the need for adhesive, solvents, or welding. The swabable valve 274 is generally used to connect the patient supply set 40 to the patient outlet port 270. Because the valve is swabable, multiple connections may be made without compromising the connection. A self-sealing silicone stem (not shown) in the swabable valve 274 also prevents fluid drips when the patient supply set 40 is removed.

The outlet selector valve 280 comprises a unitary outlet selector valve body 282 with an actuator interface head 284 and a depending valve stem 286 that terminates in a rounded or tapered bottom edge or end 288. Suitable material choices for the outlet selector valve body 282 include, but are not limited to: polyethylene (plain and fiber reinforced), polypropylene, nylon (including fiber reinforced), Ultem® PEI (polyetherimide), polycarbonate (plain and with silicone or siloxane), and like materials. The valve stem 286 defines a 90° flow passage 290 which tapers smoothly to the bottom edge or end 288 of the valve stem 286. The "bell" shape of the flow passage 290 which tapers to the rounded bottom end 288 of the valve stem 286 minimizes the potential for air bubbles to become trapped below the valve stem 286. The actuator interface head 284 of the outlet selector valve body 282 is adapted to interface with a valve actuator associated with the drive and actuating system which operates the pump 10. The valve actuator controls operation of the outlet selector valve 280 to place the valve stem 286 in orientations at least to: (1) place the flow passage 290 in fluid communication with the patient outlet port 270 and, thus, in fluid communication with the connecting passage 268 leading to the outlet manifold channel 244; (2) place the flow passage 290 in fluid communication with the waste outlet port 272 and, thus, in fluid communication with the connecting passage 268 leading to the outlet manifold channel 244; and (3) place the flow passage 290 in a shut-off position where the flow passage 290 is not aligned with either the patient outlet port 270 or the waste outlet port 272, thereby preventing fluid flow from the outlet manifold channel 244 to either outlet port 270, 272.

The actuator interface head 284 is generally T-shaped and comprises, for example, two (2) outwardly extending tabs 292 and a recessed area 294 for engagement with the valve actuator associated with the drive and actuating system. The T-shape of the actuator interface head 284 allows the outlet selector valve body 282 to slide into engagement with the valve actuator and also "keys" the outlet selector valve body 282 so that it may be engaged by the valve actuator in only one particular orientation. This interface between the actuator interface head 284 and the valve actuator of the drive and actuating system also prevents the outlet selector valve body 282 from being ejected upward from the outlet selector valve cylinder 264 on the manifold plate 230 under high operating pressure.

Additionally, the outlet selector valve 280 comprises a rear or proximal pressure sensing port 296 defined in the outlet selector valve cylinder 264 supporting the outlet selector valve body 282 that supports a pressure sensing diaphragm 298, which interfaces with the drive and actuating system so that fluid pressure in the valve bore 266 may be measured. The pressure sensing diaphragm 298 is a thin polyurethane (and like polymeric materials) diaphragm that is used to measure the fluid pressure in the outlet manifold channel 244. The pressure sensing diaphragm 298 is desirably overmolded into the pressure sensing port 296 and seals the port 296 while transferring the fluid pressure within the pressure sensing port 296 to its exterior surface. The pressure sensing diaphragm 298 allows the pressure in the outlet manifold channel 244, which is connected to the valve bore 266 via the connecting passage 268, to be measured at any time, not just when injecting fluid into a patient. The waste outlet port 272 on the outlet selector valve cylinder 264 on the manifold plate 230 is used to conduct waste fluids to the waste collection container 48 when the outlet selector valve 280 is actuated to place the flow passage 290 in fluid communication with the waste outlet port 272.

Figure 23:
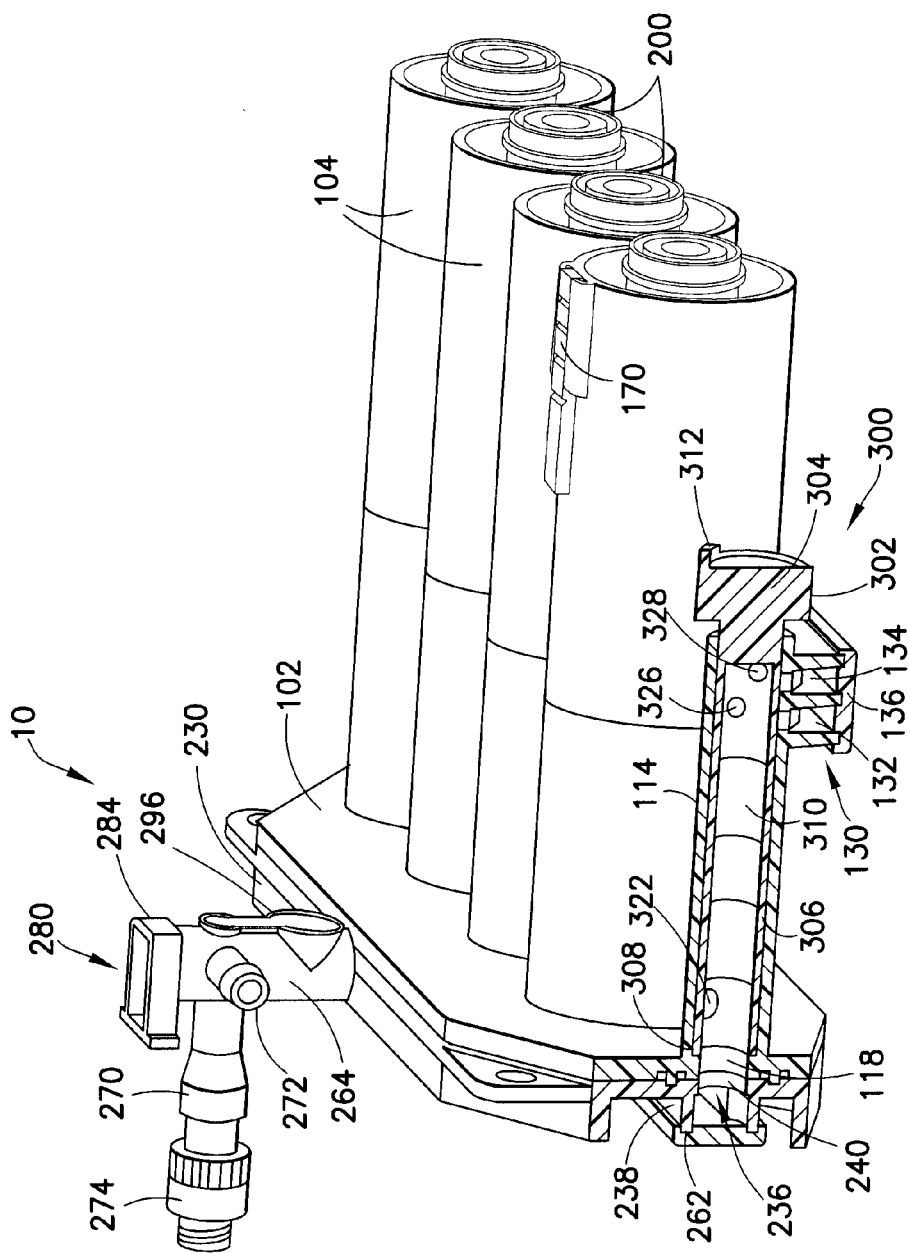
FIG. 23 is a cross-sectional perspective view taken along line 23-23 in FIG. 3.
Figure 24A:
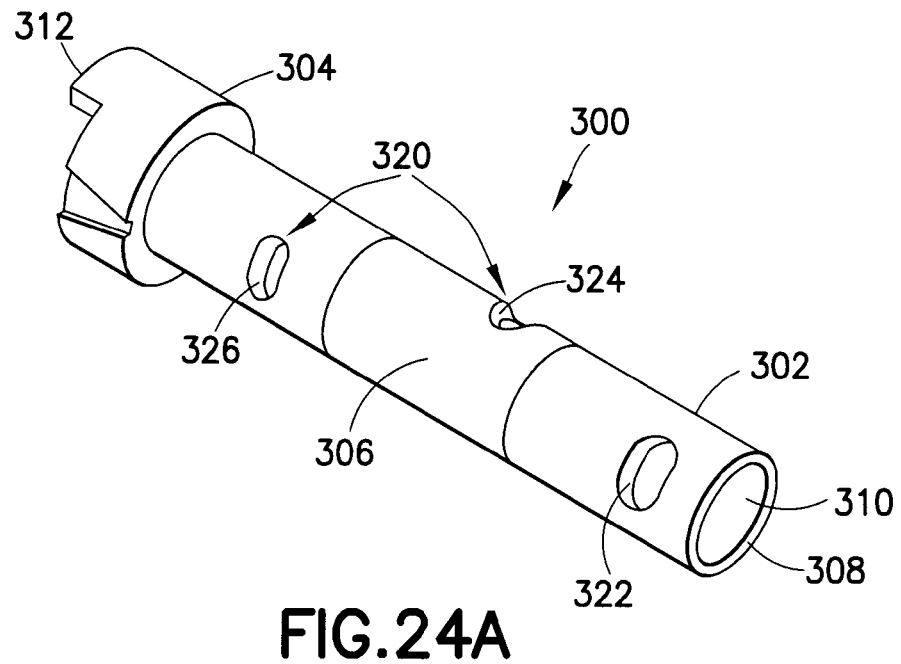
FIG. 24A is a front isometric perspective view of an inlet selector valve stem used in the fluid pump device shown in FIG. 2.
Figure 24B:
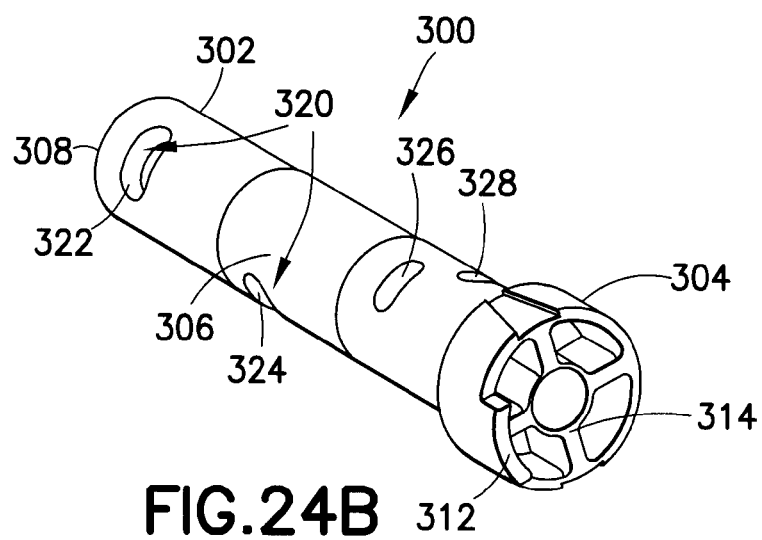
FIG. 24B is a rear isometric perspective view of the inlet selector valve stem used in the fluid pump device shown in FIG. 2.

Referring further to FIGS. 23-24, as noted in the foregoing, an inlet selector valve 300 is provided in each of the inlet selector valve cylinders 114. Each inlet selector valve cylinder 114 defines a cylindrical chamber 116 that accepts the inlet selector valve 300 which is rotationally operable within the inlet selector valve cylinder 114. The drive and actuating system which operates the pump 10 also desirably includes separate valve actuators that operate the respective inlet selector valves 300. The respective inlet selector valves 300 each comprise an inlet selector valve body 302 with an actuator interface head 304 and an elongated and hollow valve stem 306 that terminates in a distal edge or end 308 which abuts (or is disposed in proximity to) the front plate 102 and extends about the front or distal end opening 118 formed in the front plate 102. The valve stem 306 defines an axial bore or passage 310. The actuator interface head 304 of the inlet selector valve body 302 is adapted to interface with an inlet selector valve actuator associated with the drive and actuating system. The actuator interface head 304 may be generally round or circular in shape and comprises a proximally extending tab 312, or a plurality of such tabs 312, and an interface engagement member 314 formed internally within the actuator interface head 304. The proximally extending tab 312 and internal engagement member 314 form interfacing features for engagement with the inlet selector valve actuator associated with the drive and actuating system. For safety purposes, it is desirable for the valve stem 306 to be engaged to the drive and actuating system in one particular angular orientation. If the valve stem 306 can be installed in more than one angular orientation, it could be possible to deliver the wrong type of fluid. In one example, if the proximally extending tab 312 does not angularly align with the corresponding valve actuator in the fluid delivery system 2, it may not be possible to install the pump 10 in the fluid delivery system 2.

The valve stem 306 defines a series of radial inlet openings or ports 320 that connect to the central or axial passage 310. The radial inlet openings or ports 320 are located at different angular locations around the valve stem 306 and at different axial locations along the valve stem 306. The radial inlet openings or ports 320 include a first inlet port 322 for placing the first inlet port 122 on the receiving inlet selector valve cylinder 114 in fluid communication with the axial passage 310 in the valve stem 306, a second inlet port 324 for placing the second inlet port 124 on the receiving inlet selector valve cylinder 114 in fluid communication with the axial passage 310 in the valve stem 306, and third and fourth inlet ports 326, 328 positioned to allow fluid communication between either of the saline channels 132, 134 of the saline manifold 130 and the axial passage 310 in the valve stem 306. The respective inlet ports 322, 324, 326, 328 are defined at different angular locations around the valve stem 306 and are positioned at spaced axial locations along the valve stem 306 so that, at most, only one of these inlet ports 322-328 permits fluid communication with the axial passage 310 in the valve stem 306 at any given time, and thereby permit fluid flow into the valve stem 306 from the first inlet port 122, second inlet ports 124, or one of the saline channels 132, 134. In particular, the respective inlet ports 322-328 are defined at different angular locations around the valve stem 306 and spaced axial locations along the valve stem 306 so that only one of the first and second inlet ports 122, 124 and the saline channels 132, 134 of the saline manifold 130 is in fluid communication with the axial bore or passage 310 in the valve stem 306 at any given time. Accordingly, if the first inlet port 322 is in fluid communication with the first inlet port 122, the second inlet port 124 is blocked by the valve stem 306 to fluid flow, as are both of the saline channels 132, 134 of the saline manifold 130. Similarly, if the second inlet port 324 is in fluid communication with the second inlet port 124, the first inlet port 122 is blocked by the valve stem 306 to fluid flow, as are both of the saline channels 132, 134 of the saline manifold 130. If the third inlet port 326 is aligned with the first or forward saline channel 132, the first and second inlet ports 122, 124 are blocked to fluid flow by the valve stem 306, as is the second or rearmost saline channel 134. Further, if the fourth inlet port 328 is aligned with the second or rearmost saline channel 134, the first and second inlet ports 122, 124 are blocked to fluid flow by the valve stem 306, as is the first or forward saline channel 132.

In the depicted arrangement, the inlet ports 322-328 are axially spaced along the valve stem 306, with the first inlet port 322 located near the distal end 308 of the valve stem 306 and the last or fourth inlet port 328 located near the actuator interface head 304. As explained previously, the foregoing axial order of the ports 122-126 and corresponding ports 322-328 is desirable for air management issues. In particular, in the pump 10 in the accompanying figures, the "left" saline source Si is connected to the left saline port 126 so that the rearmost saline channel 134 is filled first with saline for priming purposes. The rearmost or fourth inlet port 334 in the valve stem 306 is located in the rearmost position to establish fluid communication with the rearmost saline channel 134 to allow the entire inlet selector valve 300 to be primed with saline from the far rear or proximal end. If this "saline" port was located in any other "forward" position, it would not be possible to remove all of the air from the length of the inlet selector valve 300 as air would be trapped behind this position. It is noted that the distance from the saline inlet port 328 and the proximal or rear end of axial passage 310 adjacent the actuator interface head 304 is minimized as much as possible to limit the potential for air bubbles to be trapped behind this inlet port 328 and the end of the axial passage 310.

With the foregoing radial and axial locations for the inlet ports 322-328, the inlet selector valve actuators of the drive and actuating system control operation of the right and left inlet selector valves 300 to place the valve stem 306 in an orientation to: (1) connect the first inlet port 322 with the first inlet port 122 to provide fluid communication between a first source of therapeutic or diagnostic (e.g., pharmaceutical) fluid A1, B1 contained in a connected fluid source container 30 and the corresponding inlet manifold channel 236, while the second inlet port 124 and both of the saline channels 132, 134 of the saline manifold 130 are blocked to fluid flow by the valve stem 306; (2) connect the second inlet port 324 with the second inlet port 124 to provide fluid communication between a second source of therapeutic or diagnostic (e.g., pharmaceutical) fluid A2, B2 contained in a connected fluid source container 30 and the corresponding inlet manifold channel 236, while the first inlet port 122 and both of the saline channels 132, 134 of the saline manifold 130 are blocked to fluid flow by the valve stem 306; (3) connect the third inlet port 326 with the first or forward saline channel 132 of the saline manifold 130 via saline port 332 (FIG. 5B) to provide fluid communication between a second source of saline S2 contained in a connected fluid source container 30 and the corresponding inlet manifold channel 236, while the first and second inlet ports 122, 124 and the second or rear saline channel 134 of the saline manifold 130 are blocked to fluid flow by the valve stem 306; (4) connect the fourth inlet port 328 with the second or rearmost saline channel 134 of the saline manifold 130 via saline port 334 (FIG. 5B) to provide fluid communication between a first source of saline S1 contained in a connected fluid source container 30 and the corresponding inlet manifold channel 236, while the first and second inlet ports 122, 124 and the first or forward saline channel 132 of the saline manifold 130 are blocked to fluid flow by the valve stem 306; and (5) an "OFF" position wherein the valve stem 306 is in a position to block each of the first and second inlet ports 122, 124 and the first and second saline channels 132, 134, thereby preventing fluid flow from the various external fluid sources contained in the fluid source containers 30 to the corresponding inlet manifold channel 236. Thus, at least a total of five (5) different operational states are present for each of these inlet selector valves 300 in the embodiment of the pump 10 found in the accompanying figures. However, this embodiment should not be considered limiting as additional inlet ports (not shown) may be provided on the respective inlet selector valve cylinders 114, with corresponding inlet ports (not shown) being provided in the valve stem 306 of the respective inlet selector valves 300 to accommodate additional connected fluid sources as desired.

Figure 5A:
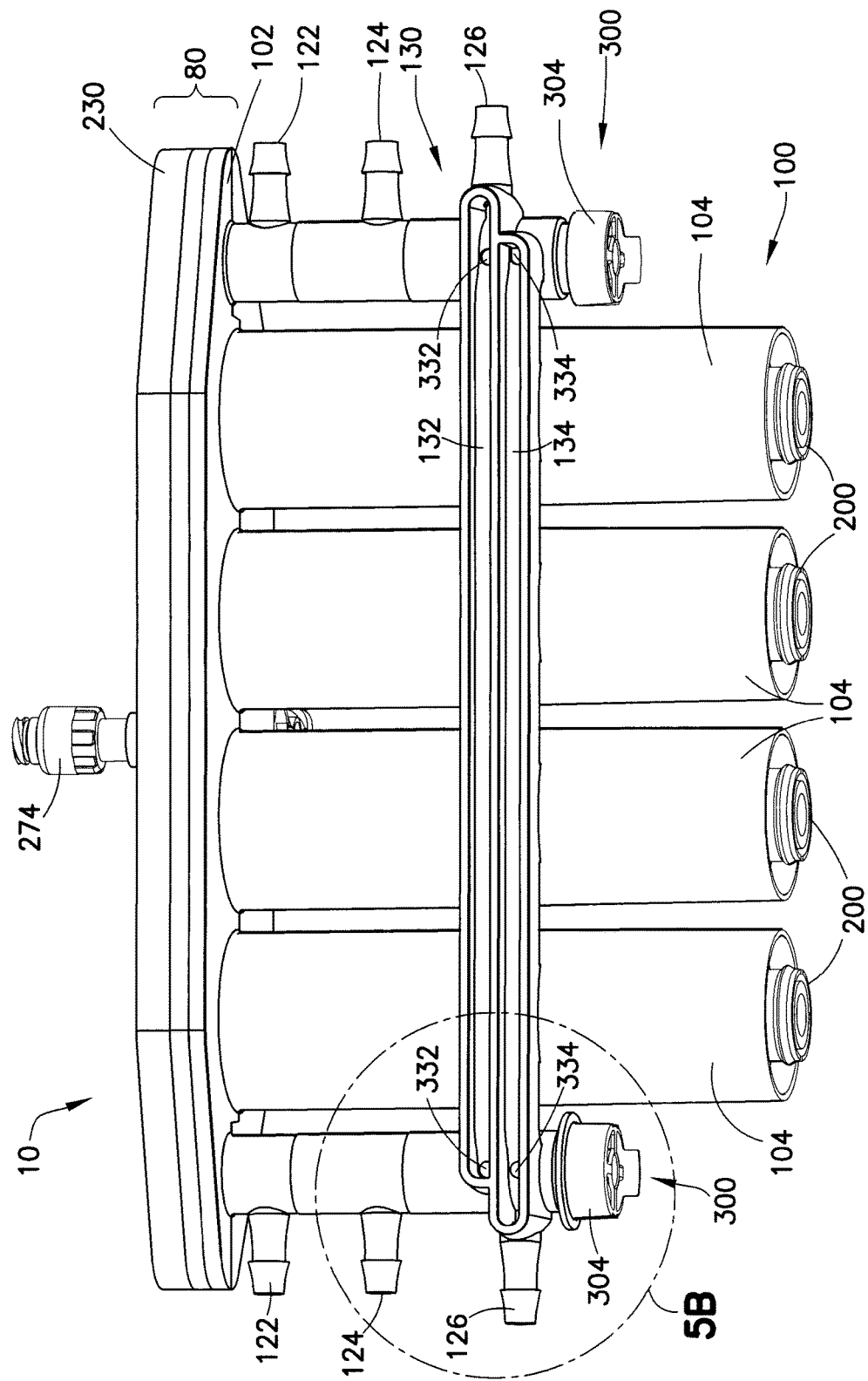
FIG. 5A is a bottom view of the fluid pump device shown in FIG. 2.
Figure 5B:
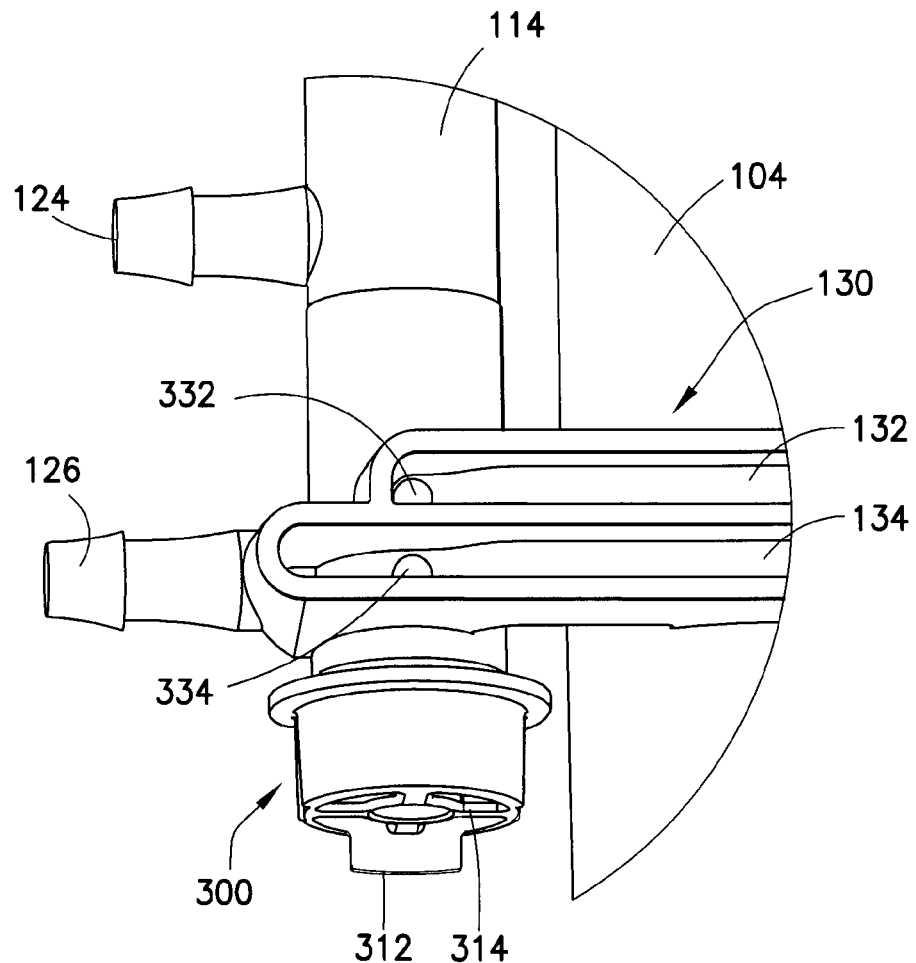
FIG. 5B is a detail view of detail 5B in FIG. 5A.
Figure 6:
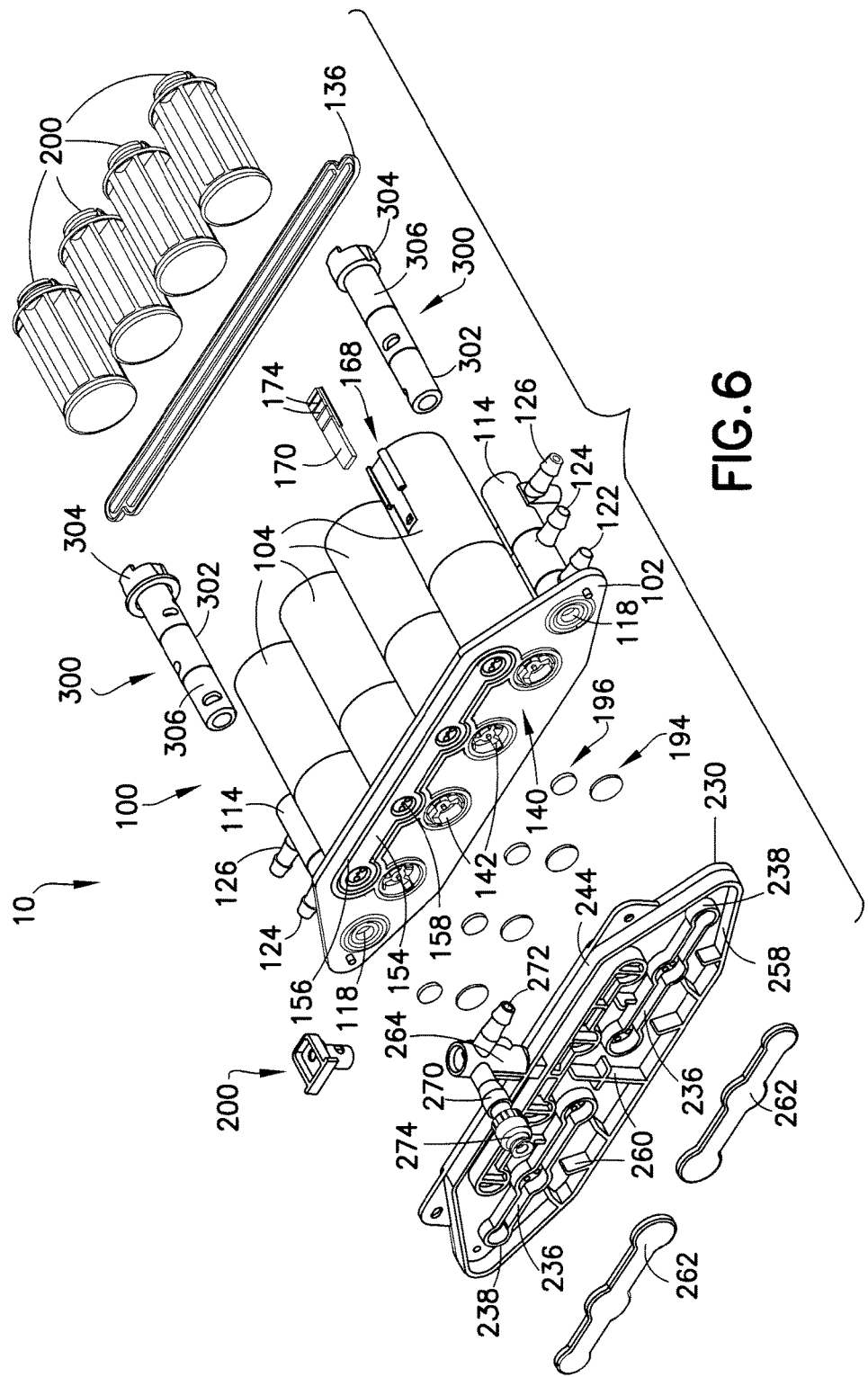
FIG. 6 is an exploded perspective view of the fluid pump device shown in FIG. 2.
Figure 7:
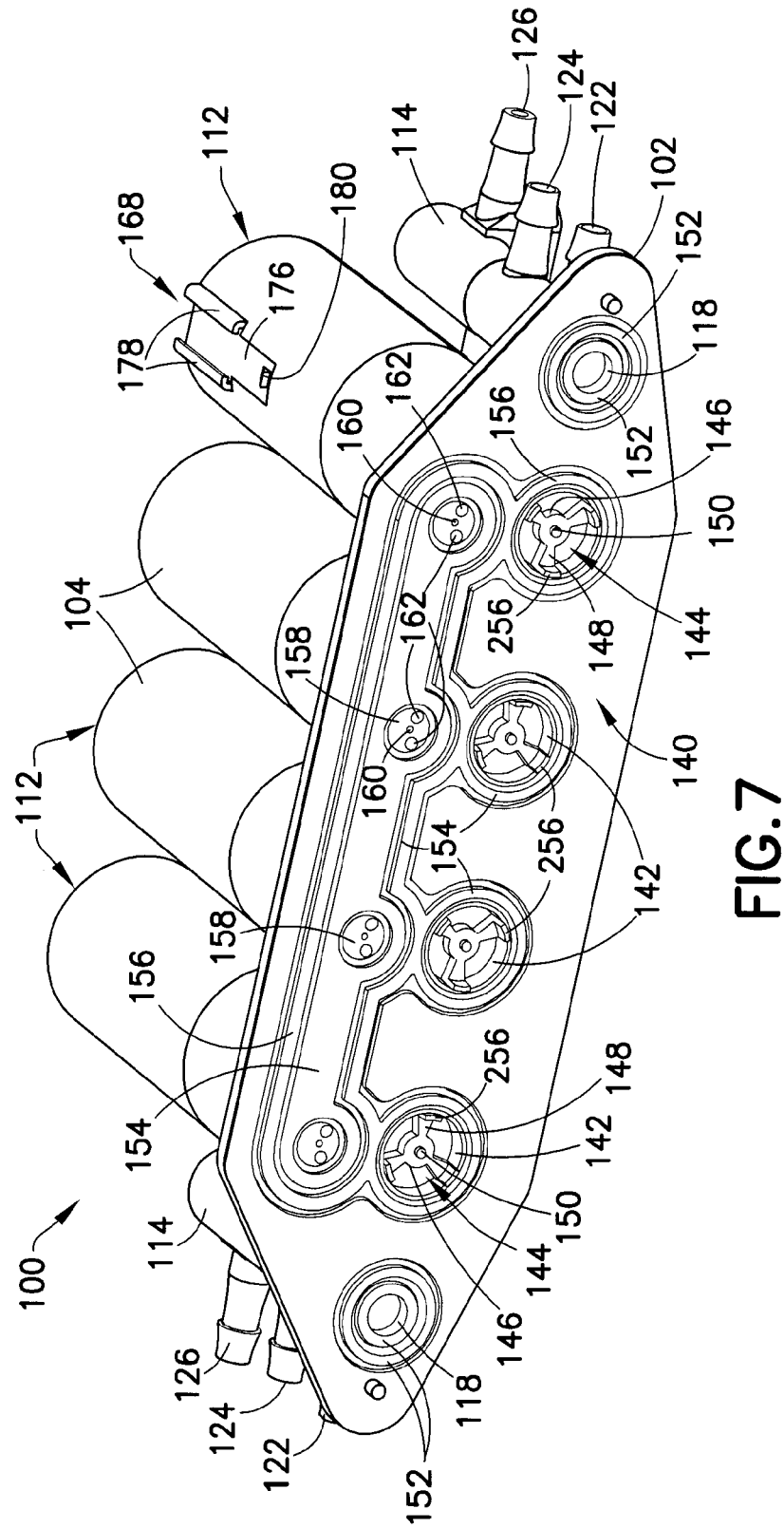
FIG. 7 is a front perspective view of a pump body of the fluid pump device shown in FIG. 2.
Figure 8:
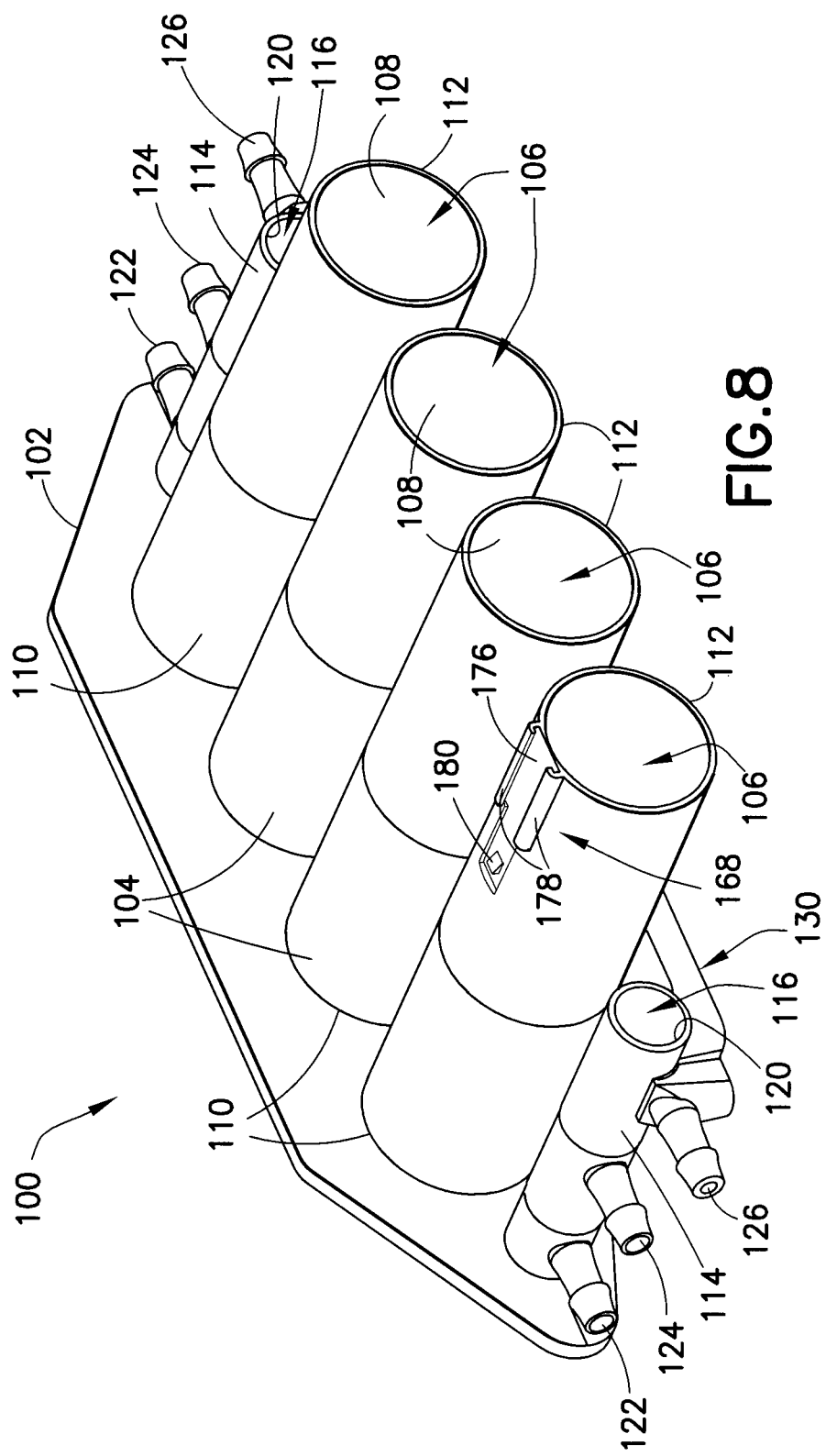
FIG. 8 is a rear perspective view of the pump body shown in FIG. 7.

Referring specifically to FIGS. 5A and 5B, it will be understood that the saline manifold 130 is formed to extend across the pump cylinders 104 and has opposing ends that connect to the respective inlet selector valve cylinders 114. With this construction, the saline channels 132, 134 extend the length between the two (2) outboard inlet selector valve cylinders 114. Saline ports 332, 334 are defined in the bottom of each of the inlet selector valve cylinders 114 to connect the inlet selector valve cylinders 114 to the saline channels 132, 134. The first or forward saline ports 332 connect the inlet selector valve cylinders 114 to the first or forward saline channel 132 and the second or rear saline ports 334 connect the inlet selector valve cylinders 114 to the second or rear saline channel 134. Accordingly, when the valve stem 306 of the actuated inlet selector valve 300 is rotated to connect the third inlet or "saline" port 326 with the first or forward saline channel 132 of the saline manifold 130, the third inlet "saline" port 326 is actually aligned with the first or forward saline port 332 in the inlet selector valve cylinder 114. Additionally, when the valve stem 306 of the actuated inlet selector valve 300 is rotated to connect the fourth inlet "saline" port 328 with the second or rear saline channel 134 of the saline manifold 130, the fourth inlet or "saline" port 328 is actually aligned with the second or rear saline port 334 in the inlet selector valve cylinder 114.

In the exemplary configuration of the pump 10 depicted in the accompanying figures, the left side inlet ports 122, 124 may be connected, respectively, to two (2) different sources of therapeutic or diagnostic (e.g., pharmaceutical) fluids, A1, A2, to be received in the two (2) left pump cylinders 104, and the left side saline port 126 may be connected to a first source of saline, designated as "S1". Fluid "A1" provided in one of the fluid source containers 30 may be connected to first inlet port 122 and fluid "A2" provided in one of the fluid source containers 30 may be connected to the second inlet port 124, or vice versa, on the left side 18 of the pump 10. Likewise, the right side inlet ports 122, 124 may be connected, respectively, to two (2) different sources of therapeutic or diagnostic (e.g., pharmaceutical) fluid, B1, B2 to be received in the two (2) right pump cylinders 104, and the right side saline port 126 may be connected to the second source of saline, designated as "S2". The two (2)-channel saline manifold 130 permits saline from either saline source S1, S2 to be pulled into either of the inlet selector valves 300 during operation of the pump 10. Fluid "B1" provided in one of the fluid source containers 30 may be connected to first inlet port 122 and fluid "B2" provided in one of the fluid source containers 30 may be connected to the second inlet port 124, or vice versa, on the right side 16 of the pump 10. Further, fluids A1, A2 may be connected to the right side inlet ports 122, 124 in any desired pairing and the fluids B1, B2 may be connected to the left side inlet ports 122, 124 in any desired pairing as an alternative configuration for the pump 10. Accordingly, for exemplary purposes only in this disclosure, fluid flow of the fluids A1, A2 contained in the fluid source containers 30 is controlled by the left side inlet selector valve 300 and fluid flow of the fluids B1, B2 contained in the fluid source containers 30 is controlled by the right side inlet selector valve 300. As noted previously, the respective inlet selector valves 300 may draw saline from either of the saline channels 132, 134 of the saline manifold 130. Hence, the respective inlet selector valves 300 may draw from either saline source S1, S2. Accordingly, each "half" of the pump 10 has a single inlet selector valve 300 that allows selection from several fluid sources that are to be fed into the two (2) associated pump cylinders 104. Thus, control of fluids to the two (2) left side pump cylinders 104 is provided by the left side inlet selector valve 300 and control of fluids to the two (2) right side pump cylinders 104 is provided by the right side inlet selector valve 300.

The initial angular orientation of the valve stem 306 of the inlet selector valves 300 may be preset by the manufacturer and this orientation may be encoded into the pump indicator plate 170 and/or into identifying indicia 172 on the pump body 100. The control system can thereby determine the initial or preset angular orientation of the valve stem 306 and operate the drive and actuating system accordingly.

Referring to FIGS. 25-28, various versions and embodiments of a fluid supply set 32 may be associated with the pump 10 to meet different patient and/or procedural needs. The combination of the pump 10 and a specific configuration of the fluid supply set 32 forms the multi-use or multi-patient disposable set for the fluid delivery system or unit 2. Each of the various versions and embodiments of the fluid supply set 32 comprises one or more fluid supply tubes 34 each having one end connected to the pump 10 and the opposing end connected to a spike 36 used to access a fluid source container 30. A "basic" embodiment of the fluid supply set 32 is shown in FIG. 25. The basic fluid supply set 32 comprises six (6) fluid supply tubes 34 which connect six (6) fluid source containers 30 to the six (6) inlet ports 122, 124, 126 on the inlet selector valve cylinders 114 on the pump body 100. The basic configuration is for a typical end user performing, for example, 8-12 procedures per day and be may be used, for example, on up to about 15 patients. In this configuration, two (2) contrast fluid source containers 30 containing contrast fluids A1, A2, for example, the same type or brand of contrast fluid, may be connected to the first and second inlet ports 122, 124 on the left side inlet selector valve cylinder 114, and two (2) contrast fluid source containers 30 containing contrast fluids B1, B2, for example, the same type or brand of contrast fluid but different from contrast fluids A1, A2, may be connected to the first and second inlet ports 122, 124 on the right side inlet selector valve cylinder 114. However, if desired, the same type of fluid may be present in all four (4) of the foregoing installed fluid source containers 30. Fluid source containers 30 containing saline S1, S2 are connected to the saline ports 126 on each of the inlet selector valve cylinders 114 in the manner discussed previously. The basic fluid supply set 32 typically has permanently attached spikes 36 on the free end of each of the fluid supply tubes 34, and the other end of each of the fluid supply tubes 34 is permanently connected to the respective inlet ports 122, 124, 126. However, one or more of the spikes 36 may be replaceable spikes if so desired. For example, replaceable spikes 36 may be provided for accessing the saline fluid source containers 30 containing saline S1, S2. Once the fluid source container 30 attached to each spike 36 is empty, that particular fluid supply tube 34 and the associated inlet port 122, 124, 126 should no longer be used because of the contamination risk involved in changing out a fluid source container 30.

In FIG. 26, a "high-use" fluid supply set 32 is shown and differs only from the basic configuration in that all the spikes 36 are replaceable. A swabable valve 70 may be provided on the free end of the fluid supply tubes 32 for connection to the spikes 36. In this variation, one fluid source container 30 may be attached to each spike 36 and, once empty, the empty container 30 and used spike 36 may be removed and discarded. The permanently attached swabable valve 70 may then be cleaned and a new spike 36 attached to the valve 70. Multiple fluid source containers 30 may be installed on a given fluid supply set 32 as long as the spike 36 is replaced with each new container 30 and the corresponding swabable valves 70 are cleaned appropriately.

In FIG. 27, another variation of the fluid supply set 32 is shown and intended for limited use with only a few patients, such as may occur on a weekend. This variation of the fluid supply set 32 may be used, for example, on up to about five (5) patients and has a single fluid source container 30 containing a desired therapeutic or diagnostic (e.g., pharmaceutical) fluid connected to one of the first inlet ports 122 on the left or right side inlet selector valve cylinders 114. A saline fluid source container 30 containing saline is connected to the saline port 126 on the same inlet selector valve cylinder 114. The spikes 36 are shown permanently attached to fluid supply tubes 34 so once a fluid source container 30 is empty, that particular fluid supply tube 34 and inlet port 122, 126 should no longer be used. However, swabable valves 70 may also be used in the manner shown in FIG. 26.

In FIG. 28, a further variation of the fluid supply set 32 is shown and is intended for use with small, single-patient fluid source containers 30. This variation is intended to be used, for example, for up to about 15 patients. In this variation, a first type of therapeutic or diagnostic (e.g., pharmaceutical) fluid A1 in a fluid source container 30 is connected to the first inlet port 122 on one of the inlet selector valve cylinders 114, and a second type of therapeutic or diagnostic (e.g., pharmaceutical) fluid B1 is connected to the first inlet port 122 on the other inlet selector valve cylinder 114. Saline S1 in a fluid source container 30 is connected to the saline port 126 on one of the inlet selector valve cylinders 114. In this variation, swabable valves 70 are provided on the free ends of the fluid supply tubes 32 for connection to replaceable spikes 36. Accordingly, once the fluid source container 30 attached to the respective spikes 36 is empty, the empty container 30 and used spike 36 may be removed and discarded. The permanently attached swabable valve 70 may then be cleaned and a new spike 36 may be attached to the valve 70, along with a new fluid source container 30.

Figure 29:
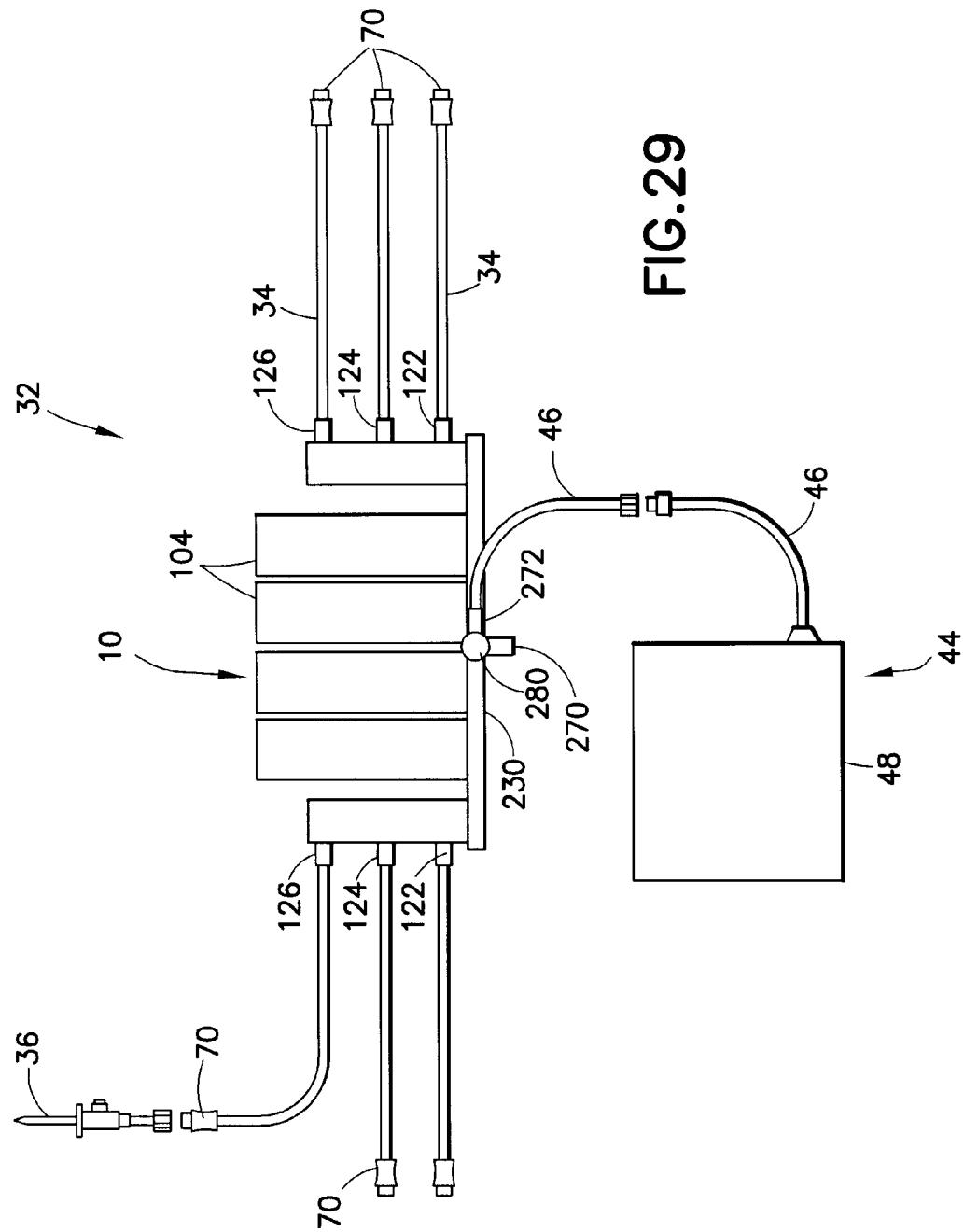
FIG. 29 is a schematic view showing the fluid pump device with the second or high-use embodiment of the fluid supply set as shown in FIG. 26, and further showing a waste collection system associated with the fluid pump device.
Figure 30:
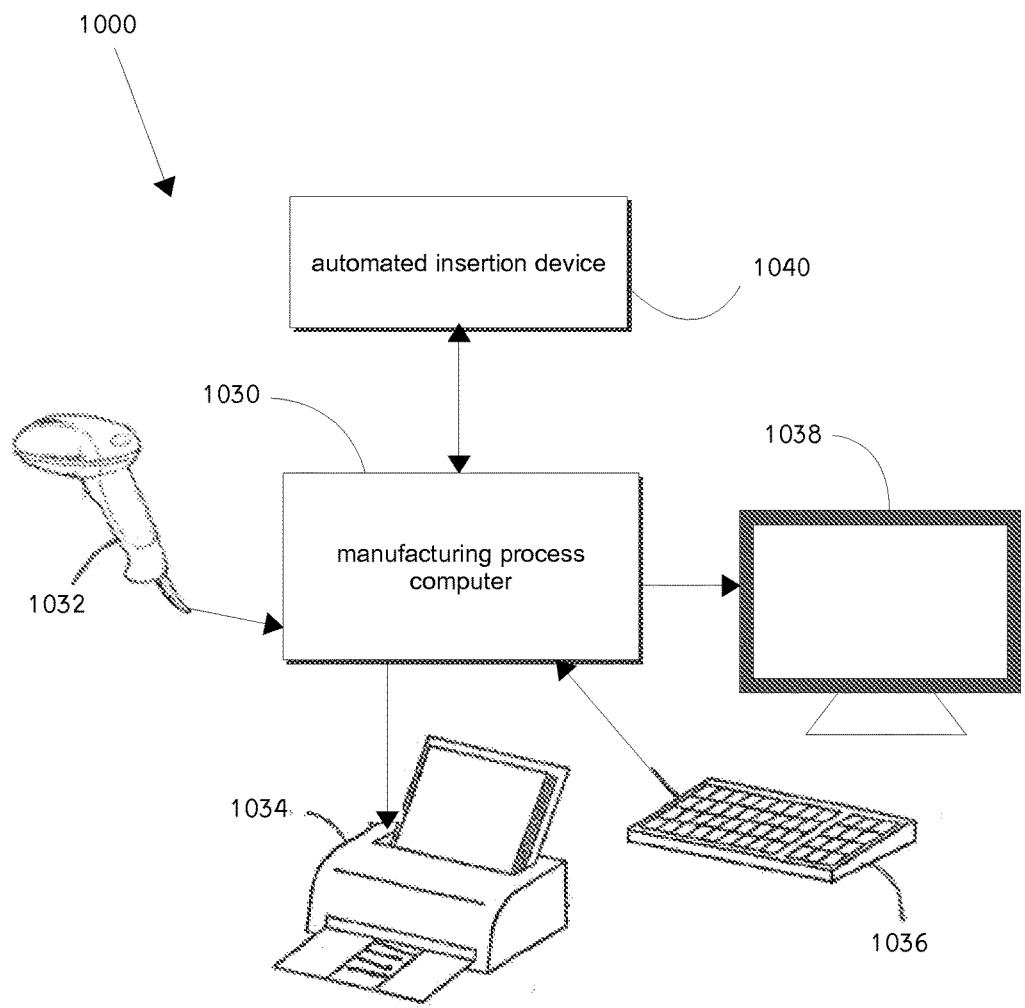
FIG. 30 is a schematic representation of a manufacturing control system used in the assembly of the fluid pump device shown in FIG. 2.
Figure 31:
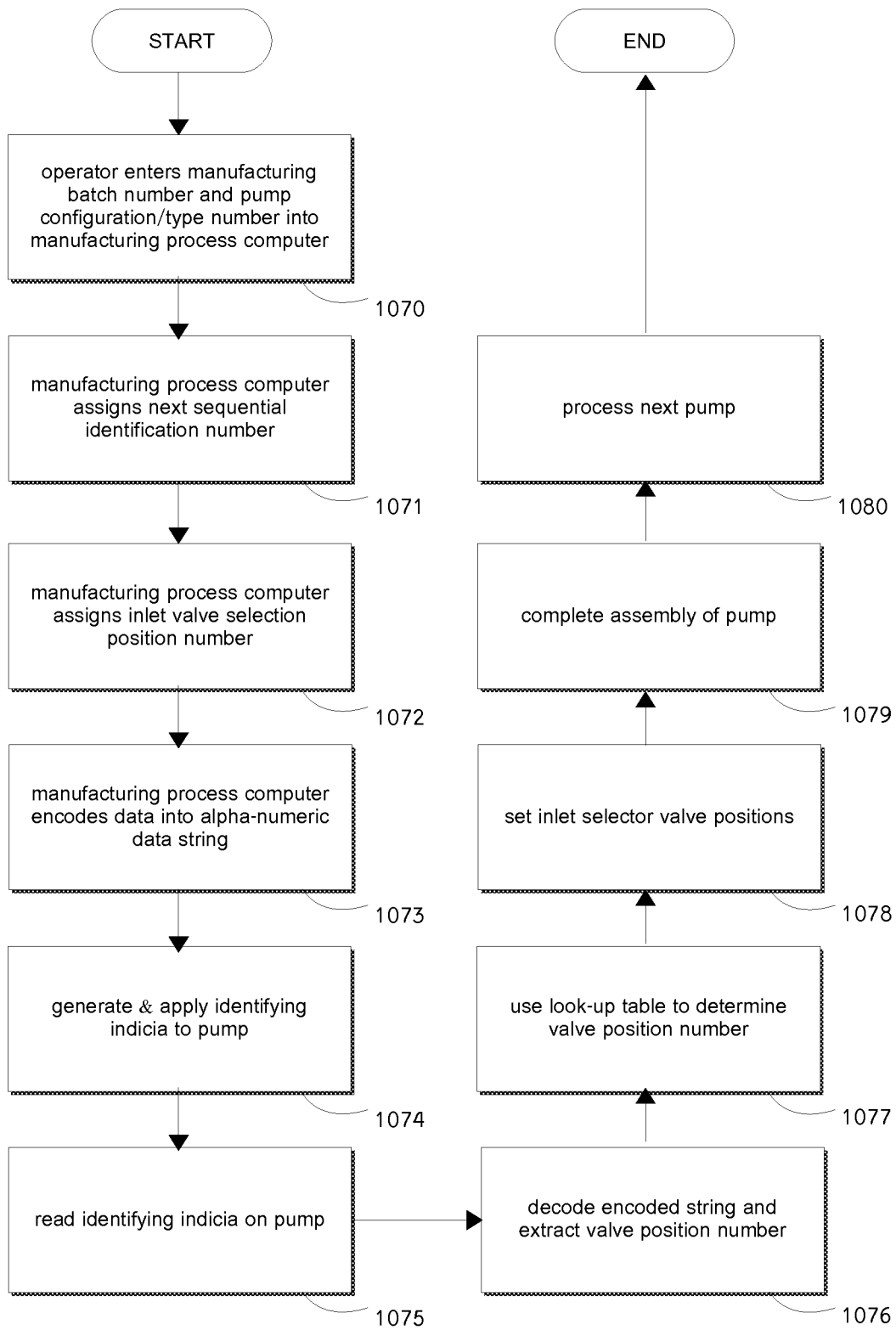
FIG. 31 is a flowchart of an exemplary assembly process for the fluid pump device shown in FIG. 2.

Referring to FIG. 29, the waste collection system 44 is shown associated with a pump 10 having a "high-use" fluid supply set 32. The waste collection system 44 generally comprises a waste collection tube set 46 connected to a waste collection container 48 used to collect and store waste fluids. The waste collection system 44 is adapted for connection to the waste outlet port 272 on the outlet selector valve cylinder 264 on the manifold plate 230, and the waste collection tube set 46 conducts waste fluids to the waste collection container 48 when the outlet selector valve 280 is actuated to place the flow passage 290 in fluid communication with the waste outlet port 272.

There are several assembly steps for assembling the pump 10 for use in the fluid delivery system 2. The following discussion is intended as exemplary and non-limiting as to an assembly process for constructing the disposable pump 10. Before beginning assembly of a "batch" or "run" of pumps 10, an operator enters a manufacturing batch number and pump type number into a manufacturing process control computer in a production facility. If the pump sequential identification numbering does not begin with 00001, the starting number is also to be specified. The manufacturing process control computer assigns a unique, sequential identification to each pump 10. This number typically begins with 00001 for the first pump 10 of the batch and is incremented by 1 for each subsequent pump 10. Next, the saline manifold cap 136 is installed over the saline manifold channels 132, 134 and is welded, typically laser or ultrasonically welded, to the pump body 100. The inlet and outlet check valves 194, 196 are placed in their respective recesses, described previously. The front manifold plate 230 may then be installed onto the pump body 100, capturing the check valves 194, 196 between these two components. The front manifold plate 230 is then welded, typically laser welded, to the pump body 100. An inlet manifold cap 262 is installed onto each of the two channel members 238 forming the respective inlet manifold channels 236.

The manufacturing process control computer next selects an inlet selector valve position number for each pump 10 and this number may be assigned sequentially starting with 01 for the first pump 10 in the batch and incrementing by one (1) for each subsequent pump 10. Once a maximum permitted value has been reached, for example 36, the counter is reset back to a value of 01 for the next or 37th pump 10. Alternatively, the manufacturing process control computer may randomly select a number between 01 and a maximum permitted value, for example 36, for the initial angular position of the valve stem 306 of the inlet selector valves 300, instead of sequentially assigning values. The designated inlet selector valve position number is combined with the uniquely-assigned serial number along with other information as desired, such as the manufacturing lot code and pump type/configuration identifier. This combined data is then encoded into a string of a predetermined number of characters. The data string is used, for example, to create the identifying indicia 172, such as a barcode label, that can be laser-etched directly onto the pump 10 or otherwise applied to the pump 10. The encoded data string is used to generate a corresponding identifying indicia 172, such as a machine-readable barcode, that may be laser-etched directly on the pump body 100, printed on a label and applied to the pump body 100, or otherwise affixed to the pump body 100. The label desirably also contains the same information in human-readable alphanumeric characters. A mist of silicone lubricant may be sprayed onto the interior wall surface of the pump cylinders 104, onto the interior surface of the inlet selector valve cylinders 114, and onto the interior surface of the outlet selector valve cylinder 264 on the manifold plate 230. Next, at a valve insertion assembly station of the manufacturing facility, the manufacturing process equipment reads the identifying indicia 172, such as a barcode label, on the pump body 100, the encoded information is decoded using a decoding algorithm, and the inlet selector valve position number is extracted. The extracted inlet selector valve position number is used in conjunction with a look-up table to determine the assembled positions of the left and right inlet selector valves 300. For example, using an extracted inlet selector valve position number, the valve stem 306 of the left inlet selector valve 300 may be placed in one predetermined position, such as angular position "4" which corresponds to a specific angular orientation of the valve stem 306 in the left inlet selector valve cylinder 114, and the valve stem 306 of the right inlet selector valve 300 may be placed in another predetermined position, such as angular position "1" which corresponds to a specific angular orientation of the valve stem 306 in the right inlet selector valve cylinder 114. Next, the two (2) valve stems 306 and four (4) plungers 200 are loaded into an automated insertion device, which uses servomotors to adjust the angular orientation of the left and right valve stems 306 to match the angular positions indicated by the extracted inlet selector valve position number. The automated insertion device concurrently inserts both valve stems 306 and all four (4) plungers 200 into the respective inlet selector valve cylinders 114 and pump cylinders 104 on the pump body 100. It will be appreciated that the valve stems 306 and the plungers 200 may be inserted into the respective inlet selector valve cylinders 114 and pump cylinders 104 on the pump body 100 in a two or more step process, for example, one at a time. In another example, the valve stems 306 may be inserted into the respective inlet selector valve cylinders 114 first, and then rotated to the correct angular positions.

Additionally, for the outlet selector valve 280, the valve stem 286 of the outlet selector valve body 282 is inserted into the outlet selector valve cylinder 264 on the manifold plate 230. Prior to insertion, the angular orientation of the valve stem 286 is adjusted to ensure that the flow passage 290 is aligned or in fluid communication with the waste outlet port 272 on the outlet selector valve cylinder 264. The swabable valve 274 may be preassembled to the patient outlet port 270. Next, the fluid supply tubes 34 of the designated fluid supply set 32 are attached to the inlet ports 122, 124, 126 on the inlet selector valve cylinders 114 via, for example, integral barbs on the inlet ports 122, 124, 126. Next, the pump indicator plate 170 is installed into the recessed groove 176 on the outside of one of the pump cylinders 104. The indicator plate 170, as described previously, contains grooves 174 which indicate at least the specific pump configuration of the pump 10 based on the associated fluid supply set 32 for the pump 10. The groove pattern 174 in the pump indicator plate 170 matches the configuration of the pump 10 and its associated fluid supply set 32 (see FIGS. 25-28). The waste collection tube set 46 with attached waste collection container 48 is attached to the waste outlet port 272 on the outlet selector valve cylinder 264 on the manifold plate 230. In a further example, instead of using the indicator plate 170 with grooves 174, a blank plate may be provided and inserted into each pump and, using a laser marking system or other like method, the grooves 174 could be burned into each blank plate during the manufacturing process.

Referring next to FIGS. 30-38, FIG. 30 generally depicts a manufacturing process system 1000 for the pump 10, comprising manufacturing process computer 1030 that is provided with connections to an indicia reader 1032, for example a barcode scanner, an indicia printing/creating device 1034, such as barcode printer, RFID writer, etc., an input device 1036, such as a keyboard or mouse, a display 1038, and an automated insertion device 1040. The manufacturing process computer 1030 may include various types of memory, data storage devices, processors, video cards, input and output ports and/or devices, and other features known in the art.

Figure 32:
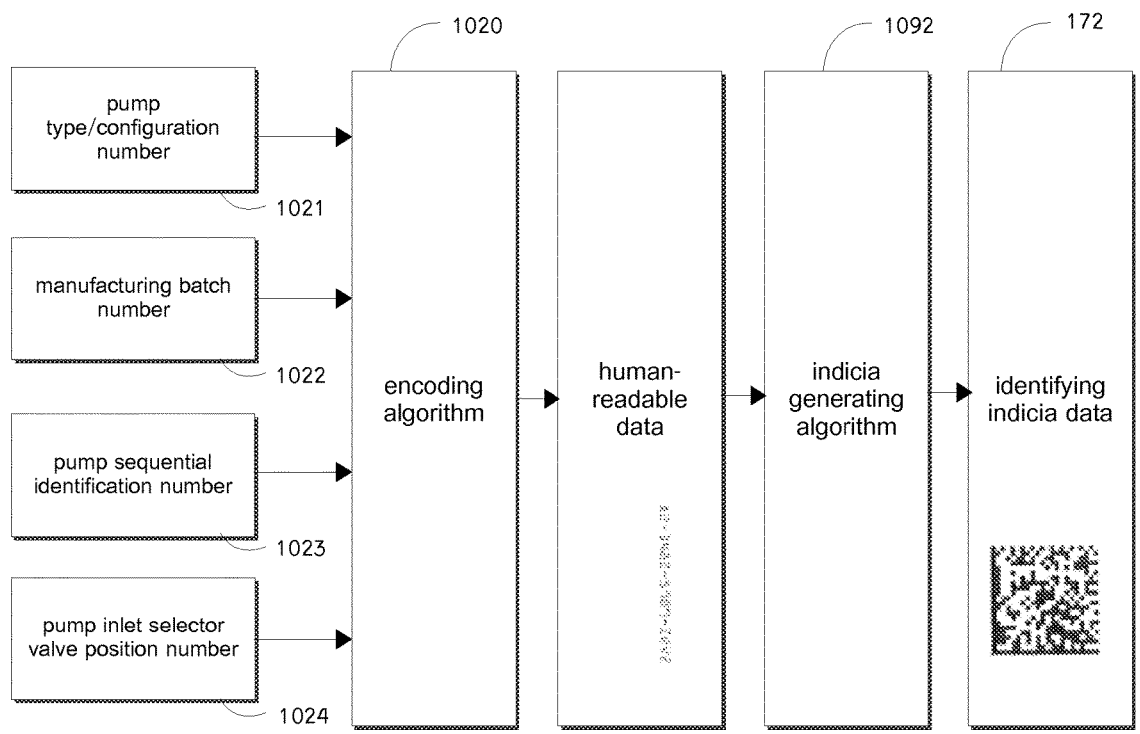
FIG. 32 is a flowchart of an exemplary process for generating identifying indicia based on specific features or input parameters associated with the fluid pump device shown in FIG. 2.
Figure 33:
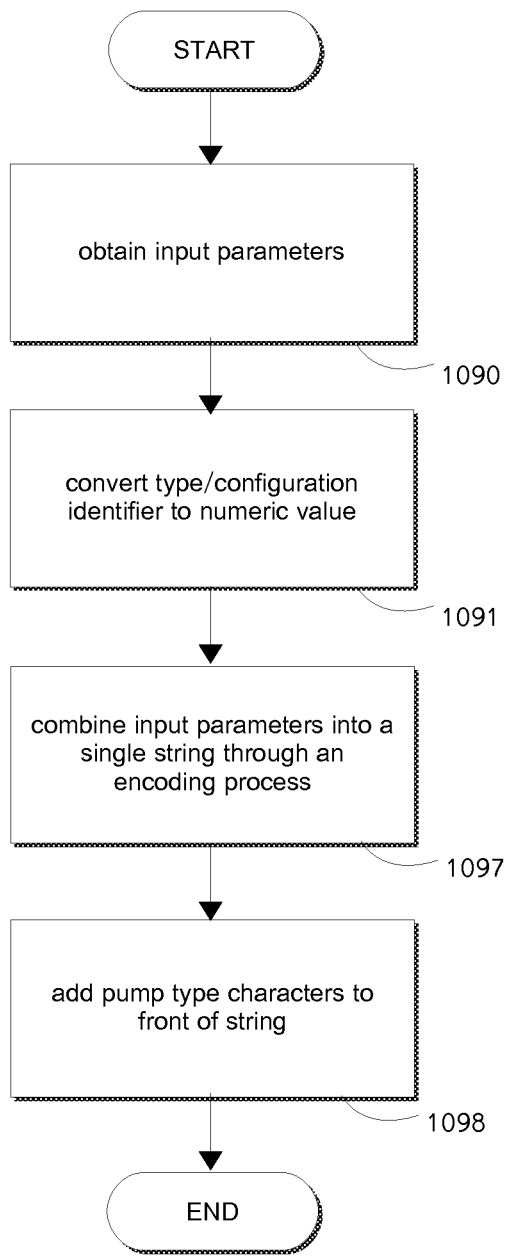
FIG. 33 is a flowchart of an exemplary encoding process used in the assembly process for the fluid pump device shown in FIG. 2.
Figure 34:
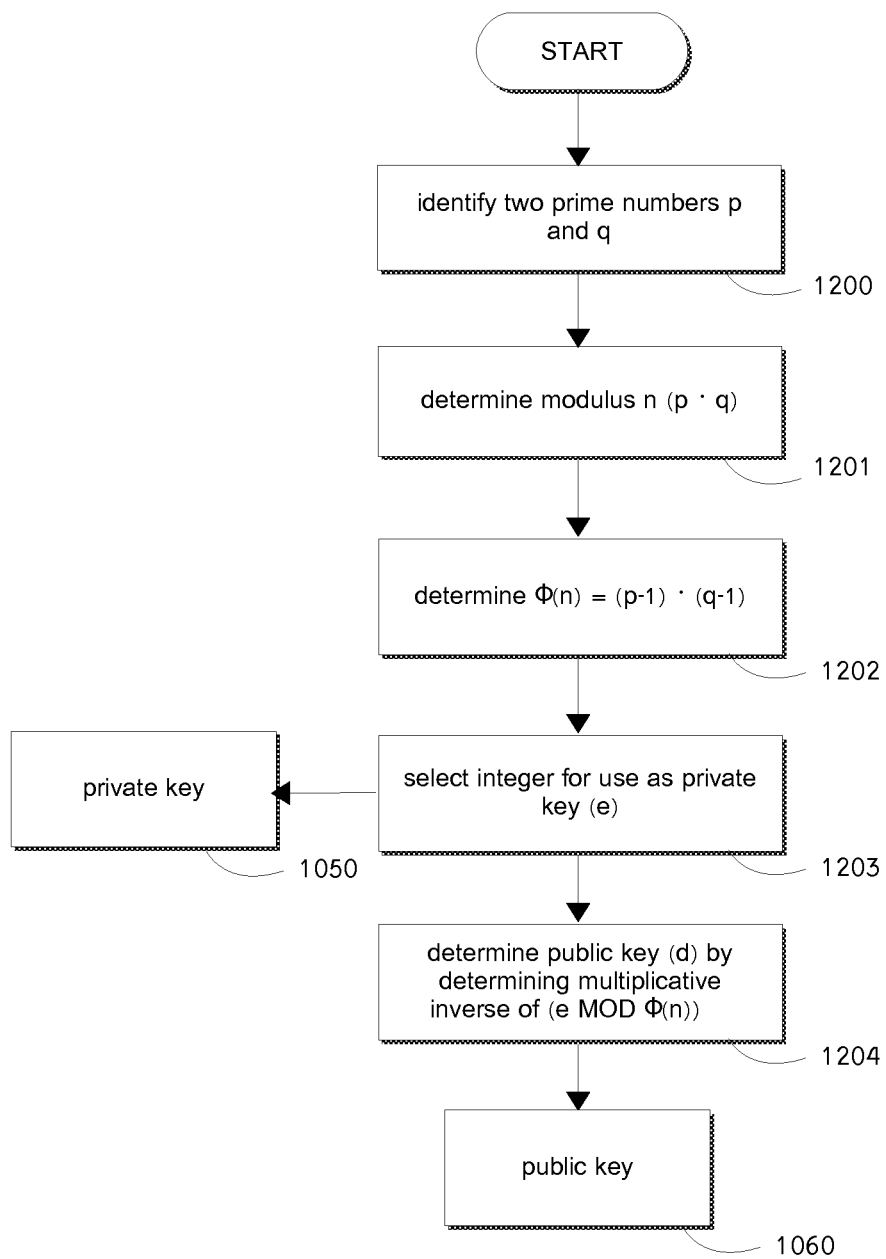
FIG. 34 is a flowchart of an exemplary algorithm used to generate encryption and decryption keys in the assembly process and operation of the fluid pump device shown in FIG. 2.

Referring to FIGS. 31-38, FIG. 31 depicts an exemplary flowchart for a method of manufacturing/assembling the disposable fluid pump devices 10 utilizing an encoding algorithm 1020, such as that depicted in FIG. 34. As a first step 1070, an operator (e.g., an individual or a machine) inputs pump input parameters, such as a pump configuration/type number 1021 and a manufacturing batch number 1022, into the manufacturing process computer 1030 or other computing device connected to the manufacturing process computer 1030 with an input device, such as a keyboard. As a second step 1071, the manufacturing process computer 1030 assigns a unique, pump sequential identification number 1023 to each pump 10. This number will typically begin with 00001 (or some other representation of 1) for the first pump 10 of a particular batch, and will be incremented by 1 for each subsequent pump 10. If the pump sequential identification number 1023 is not to begin with 00001 (or some other representation of 1), the starting number must also be inputted.

As a third step 1072, the manufacturing process computer 1030 assigns/determines an inlet selector valve position number 1024 for each pump 10. This number may be assigned sequentially (e.g., starting with 01 and incrementing for each subsequent pump 10). Once the maximum value is reached (e.g., 36 for a pump 10 having two inlet selector valve stems 306 with 6 possible angular positions), the counter may reset back to 01. It is also possible for the manufacturing process computer 1030 to assign the inlet selector valve position number 1024 for each pump 10 randomly instead of sequentially assigning values.

As a fourth step 1073, an encoded string of characters is generated by combining the inlet selector valve position number 1024, the pump sequential identification number 1023, and other information (e.g., the manufacturing batch code/number 1022, pump configuration/type number 1021, etc.) for each pump 10. It will be appreciated that a number of processes and/or algorithms may be applied to generate the encoded string of characters with various pump identification information. An exemplary, but non-limiting, algorithm will be described herein and is shown in FIG. 34. The pump configuration/type number 1021 is determined by the capabilities/configuration of the pump 10, and may be based at least in part on the type of pump 10 required, as shown in FIGS. 25-28, wherein various different versions and embodiments of the fluid supply set 32 are associated with the pump 10.

As a fifth step 1074, the manufacturing process computer 1030 or other computing device generates identifying indicia 172 representing the string of characters created previously. It will be appreciated that such identifying indicia 172 may include, but is not limited to, a machine-readable barcode, a human-readable string, an RFID tag/transponder, a QR Code (e.g., a type of matrix barcode), and/or other indicia capable of representing the string of characters. This identifying indicia 172 may be printed on a label with the barcode printer (e.g., indicia creating device) 1034 and affixed to the exterior of the pump 10 as described previously. Alternatively, the identifying indicia 172 may be etched or otherwise encoded into the exterior of the pump body 100. For example, the identifying indicia 172 may be laser-etched into the exterior of the pump body 100.

As a sixth step 1075, an indicia reader 1032 connected to an assembly station or other like device reads the identifying indicia 172 associated with the pump 10 to identify the encoded string of characters. It will be appreciated that this step may be accomplished through any number of automated methods, depending on the type of identifying indicia 172 used, and may involve a typical infrared scanner, an image and/or character recognition device, an RFID reader, or other type of indicia-identifying sensor or device.

As a seventh step 1076, a computing device connected to the valve assembly station, for example the manufacturing process computer 1030 or other like device, decodes the encoded string of characters using a process or algorithm corresponding to that used in the fourth step 1073 to determine/extract the inlet selector valve position number 1024 for each pump 10. However, it will be appreciated that the decoding process may not necessarily be the inverse of the encoding process performed in step 1073 and, as described herein, asymmetrical public and private keys may be used for encoding and decoding.

As an eighth step 1077, the computing device used in the seventh step 1076 determines the valve positions of both inlet selector valve stems 306 from the inlet selector valve position number 1024. A look-up table may be used for this step to match corresponding valve positions from each inlet selector valve position number 1024.

As a ninth step 1078, the angular orientations of the inlet selector valve stems 306 are set according to the values calculated in the eighth step 1077 as the inlet selector valve stems 306 are physically assembled into the pump body 100 (e.g., inserted into the receiving inlet selector valve body 302). This assembly step may be completed by a machine or device, such as an automated insertion device 1040. The automated insertion device 1040 may use servo motors to adjust the angular orientation of the respective inlet selector valve stems 306 to match the positions indicated or determined This machine or device may also insert the plungers 200 into the respective pump cylinders 104. However, it will be appreciated that the inlet selector valve stems 306 may also be positioned manually if so desired.

Once the inlet selector valve stems 306 are inserted and set at the correct angular orientation, or at any time prior, additional steps 1079 related to the manufacture, assembly or packaging of the pump 10 may be completed. For example, the saline manifold cap 136 may be installed over the saline manifold channels 132, 134 and laser-welded in place. Further, the inlet and outlet check valves 194, 196 may be placed in their respective receiving recesses. The front manifold plate 230 may be installed onto the pump body 100, capturing the check valves 194, 196 between these two components, and may be laser welded (or otherwise affixed) to the pump body 100. The inlet manifold cap 262 may be installed onto each of the two inlet manifold channels 236 and affixed to the front manifold plate 230. A lubricant (e.g., silicone lubricant) may be sprayed or otherwise applied on the inside surface of the pump cylinders 104, inlet selector valve cylinders 114, and outlet selector valve cylinder 264. Other final assembly steps to complete the pump 10 were described previously.

During manufacture of the pump 10, each inlet selector valve stem 306 may be placed in a plurality (N) of possible angular positions. Therefore, the total number of possible configurations for both inlet selector valve stems 306 is equal to N*N. In the present embodiment, there are six (6) possible positions for each inlet selector valve stem 306 in relation to the receiving inlet selector valve body 302, and a seventh "OFF" position, resulting in thirty-six (36) possible configurations for each pump 10, not including the "OFF" positions. These angular positions are preferably evenly spaced apart and, for example, the "OFF" position represents a 0° (or 360°) angular position, position one (1) a 51° angular position, position two (2) a 102° angular position, position three (3) a 153° angular position, position four (4) a 207° angular position, position five (5) a 258° angular position, and position six (6) a 309° angular position. However, it will be appreciated that there may be any number of different angular positions, and that the spacing or angular rotation of such positions may differ.

As just described, a plurality of input parameters may be associated with each pump 10 and this information may be encoded into a string of characters for later identification. As shown in FIG. 32, such parameters may include, but are not limited to, a pump configuration/type number 1021, a manufacturing batch number 1022, a unique, pump sequential identification number 1023, and an inlet selector valve position number 1024. The pump configuration/type number or identifier 1021 may indicate the type of unit/device and its physical condition and may be represented by a two-character alpha-numeric identifier with a range of 00-ZZ. This identifier may be used to indicate that a particular unit/device is intended to be used with a particular system, whether the disposable device is a pump cartridge or a single-patient disposable set, and/or a specific configuration of that device or system. For example, there may be four different configurations for the pump 10: basic (FIG. 25), high-use (FIG. 26), limited use/emergency-use (FIG. 27), and single-dose container use (FIG. 28), represented respectively by A2-A5. The different configurations may indicate, for example, the number of bottles of contrast or bags of saline, the physical arrangement/configuration of such containers, whether a contrast bottle may be replaced after each patient, and/or whether fluid supply containers may be replaced.

The manufacturing batch number 1022 indicates the manufacturing batch or lot number associated with each pump 10. The manufacturing batch number 1022 may always be a set number of digits (e.g., 6) and, when necessary, leading zeros (e.g., 000010 instead of 10) may be added to ensure that the batch number always has the set number of digits. For example, if the set number of digits is six (6), the permitted range of the manufacturing batch number parameter would be 000001 to 999999.

The pump sequential identification number 1023 distinguishes multiple pumps from the same batch from one another. The pump sequential identification number 1023 may be a set number of digits (e.g., 5) and, when necessary, leading zeros (e.g., 00010 instead of 10) may be added to ensure that the pump sequential identification number 1023 is the set number of digits. Typically, this identifier will begin with 00001 for the first device in a given batch and can increment with each subsequent device up to 99999.

As already mentioned, each pump 10 may have two (2) rotary inlet selector valve stems 306 and each valve stem 306 may be assembled in any one of a number of possible angular positions, one of which is an "OFF" position. The inlet selector valve position number 1024 represents the angular positions of both rotary inlet selector valve stems 306, and a look-up table may be used to identify the angular position of the inlet selector valve stems 306 from the inlet selector valve position number 1024. In this example, there are six (6) possible angular positions for each inlet selector valve stem 306 in relation to each inlet selector valve body 302. Every possible combination of angular positions for both the left and right inlet selector valve stems 306 is represented by an inlet selector valve position number 1024 from 01-36. For example, an inlet selector valve position number of 01 indicates that both the first and second inlet selector valve stems 306 are at a first angular position and an inlet selector valve position number of 10 indicates that the first inlet selector valve stem 306 is at a second angular position and the second inlet selector valve stem 306 is at a fourth angular position.

Referring specifically to FIGS. 33-34, an algorithmic process for generating the encoded string of characters and identifying indicia 172 based on specific features or parameters associated with the fluid pump device 10 will now be described. The pump configuration/type number 1021 (e.g., "A2"), manufacturing batch number 1022 (e.g., "654321"), pump sequential identification number 1023 (e.g., "12345") and pump inlet selector valve position number 1024 (e.g., "33") are processed according to the encoding algorithm 1020, which generates a character string of a specified number of characters. The string of characters may then be formatted as a human-readable string (e.g., "A2-348Z-5989-ZQV2") and/or encoded into a machine-readable identifying indicia 172, such as a standard barcode (e.g., UPC, EAN, Code 93, Code 128, etc.), a matrix barcode (e.g., a 2-dimensional code such as a Quick Response (QR) code, Aztec code, etc.), an electronic programmable memory (e.g., an RFID tag/transponder), or any other indicia capable of being read or otherwise recognized by a device, by an indicia generating algorithm 1092.

FIG. 33 illustrates a flowchart for an exemplary but non-limiting method for processing various input parameters (e.g., the pump configuration/type number 1021, manufacturing batch number 1022, pump sequential identification number 1023, and pump inlet selector valve position number 1024) into a string of characters. As a first step 1090, the input parameters are identified/obtained through manual input or an automated process. Then, at a second step 1091, the pump configuration/type number 1021 is converted from alpha-numeric characters ("A2") to a conventional four (4)

digit number. This may be accomplished by using a look-up table (conversion chart), or by another method. As a third step 1097, the input parameters are combined into a single encoded string of characters through an encoding process. In one example, the encoding process includes applying an encoding or encryption algorithm 1020 to the pump parameters. The encoding algorithm 1020 may be executed with one or more keys and/or mathematical formulas. After the final string is determined, it may then be printed on a label, etched onto the pump body 100, and/or encoded onto a machine-readable identifying indicia 172 such as a standard barcode, a matrix barcode, electronic programmable memory (e.g., an RFID tag/transponder), or any other indicia capable of being read or otherwise recognized by a device.

The encoding algorithm 1020 may use one or more symmetrical or asymmetrical key values to encode and/or decode the string containing the input parameters. In one example, an asymmetrical key exchange system is used to encode the string at a manufacturing stage and decode the string by an end-user or fluid delivery system 2. One such key exchange system includes the use of a public-private key encryption algorithm, such as the RSA algorithm or other like algorithm. The RSA algorithm is explained in further detail in U.S. Pat. No. 4,405,829, which is hereby incorporated by reference. In an asymmetrical public-private key process, a first key is a string of alpha-numeric characters, as an example, that is used to encrypt the pump parameters. In one example, a binary representation of the first key may be combined with a binary representation of the pump parameters through an exclusive-or (XOR) operation. A second key, different from the first key, is then used to decode the pump parameters. Although either key (e.g., encoding or decoding) may be public or private, in one example, the encoding key is private and resides only in the manufacturing process computer 1030. Likewise, the decoding key may be the public key, and may be included in the on-board software of a fluid delivery system 2 to allow the actuators to position the pump valves appropriately. By using separate keys for the encoding and decoding processes, the value of the public key (i.e., the decoding key) can be determined without compromising the private key (i.e., the encoding key).

Referring now to FIG. 34, a flowchart for a key generation process for generating a public key 1060 and a private key 1050 is shown. Initially, at a first step 1200, two prime numbers (e.g., 'p' and 'q') are identified. These numbers may be arbitrary and, as an example, may be randomly generated. At a second step 1201, a modulus (e.g., 'n') is determined by multiplying 'p' and 'q'. From the values of 'p' and 'q', $\phi(n)$ is determined by the equation $(p-1)*(q-1)$ at a third step 1202, where $\phi(n)$ is Euler's totient function. At a fourth step 1203, an integer (e.g., 'e') is selected for use as an exponent of the private key 1050, and the private key 1050 consists of the exponent 'e' and modulus 'n'. At a fifth step 1204, an exponent 'd' is determined by calculating the multiplicative inverse of 'e mod $\phi(n)$' (i.e., $e^{-1}*(\bmod \phi(n))$). The public key 1060 thus consists of exponent 'd' and modulus 'n', and cannot be used to reverse-engineer the private key 1050.

Figure 35:
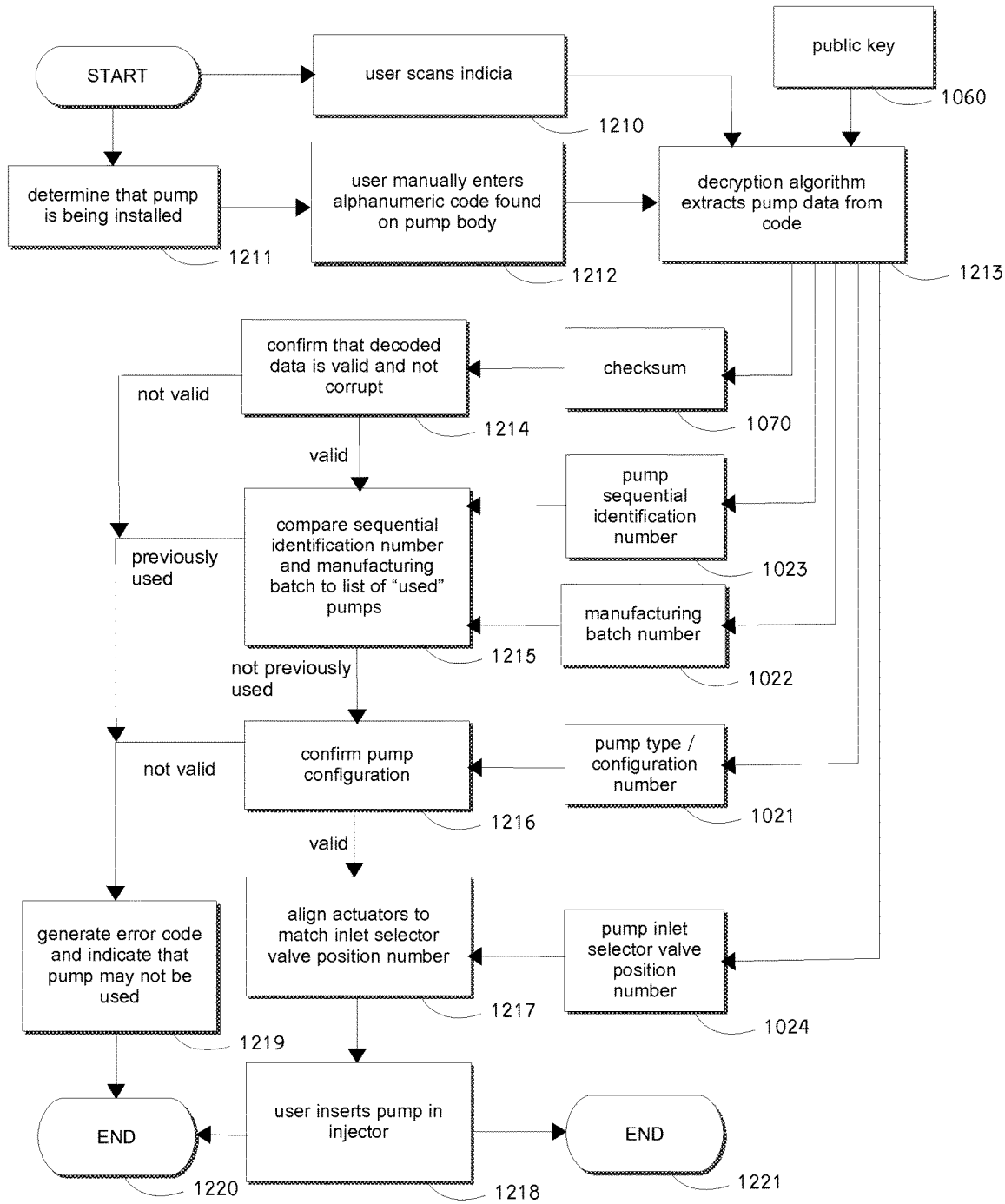
FIG. 35 is a flowchart of an exemplary process for installing and verifying the fluid pump device shown in FIG. 2 in a drive and actuating system which operates the fluid pump device.

With reference to FIG. 35, a flowchart for an installation process for a pump 10 is shown. A user of a pump 10 may begin by scanning identifying indicia 172 at step 1210 or, alternatively, by an injector determining that the pump 10 is being installed at step 1211. If the identifying indicia 172 is not scanned, the user may be prompted to enter an alpha-numeric code representing the encoded parameters (e.g., human-readable data) from the pump 10 into an input device 1036 in communication with the fluid delivery system 2 at step 1212. At a next step 1213, a decryption algorithm is used to extract pump parameters from the encoded data with a public key 1060, or by some other method. At step 1214, a checksum 1070 obtained from the decoded data is used to confirm that the remainder of the decoded data is valid and not corrupt. If the data is corrupt, the method proceeds to step 1219, where an error code is generated and an indication provided to a user that the pump may not be used, and the method unsuccessfully ends at step 1220. If the decoded data is valid and not corrupt, the method proceeds to step 1215 and the pump sequential identification number 1023 and manufacturing batch number 1022 are compared to a database of pumps that have already been used or are otherwise expired. If the pump 10 has been used before or is otherwise expired, the method proceeds to step 1219 where an error code is generated, and then to step 1220 where the method unsuccessfully ends. Otherwise, if the pump is determined to have not been used or is not otherwise expired, at a next step 1216, the pump type/configuration number is used to confirm the configuration of the pump 10. If the confirmation fails, the method proceeds to step 1219, where an error code is generated and the method ends unsuccessfully at step 1220. Otherwise, if the confirmation is successful, the method proceeds to step 1217 and the actuators of the fluid delivery system 2 are automatically aligned to match the pump inlet selector valve position number 1024. Once the pump 10 is inserted into the injector at step 1218, the method ends successfully at step 1221 by allowing operation of the pump 10, or ends unsuccessfully at step 1220, disallowing operation of the pump 10.

Figure 36:
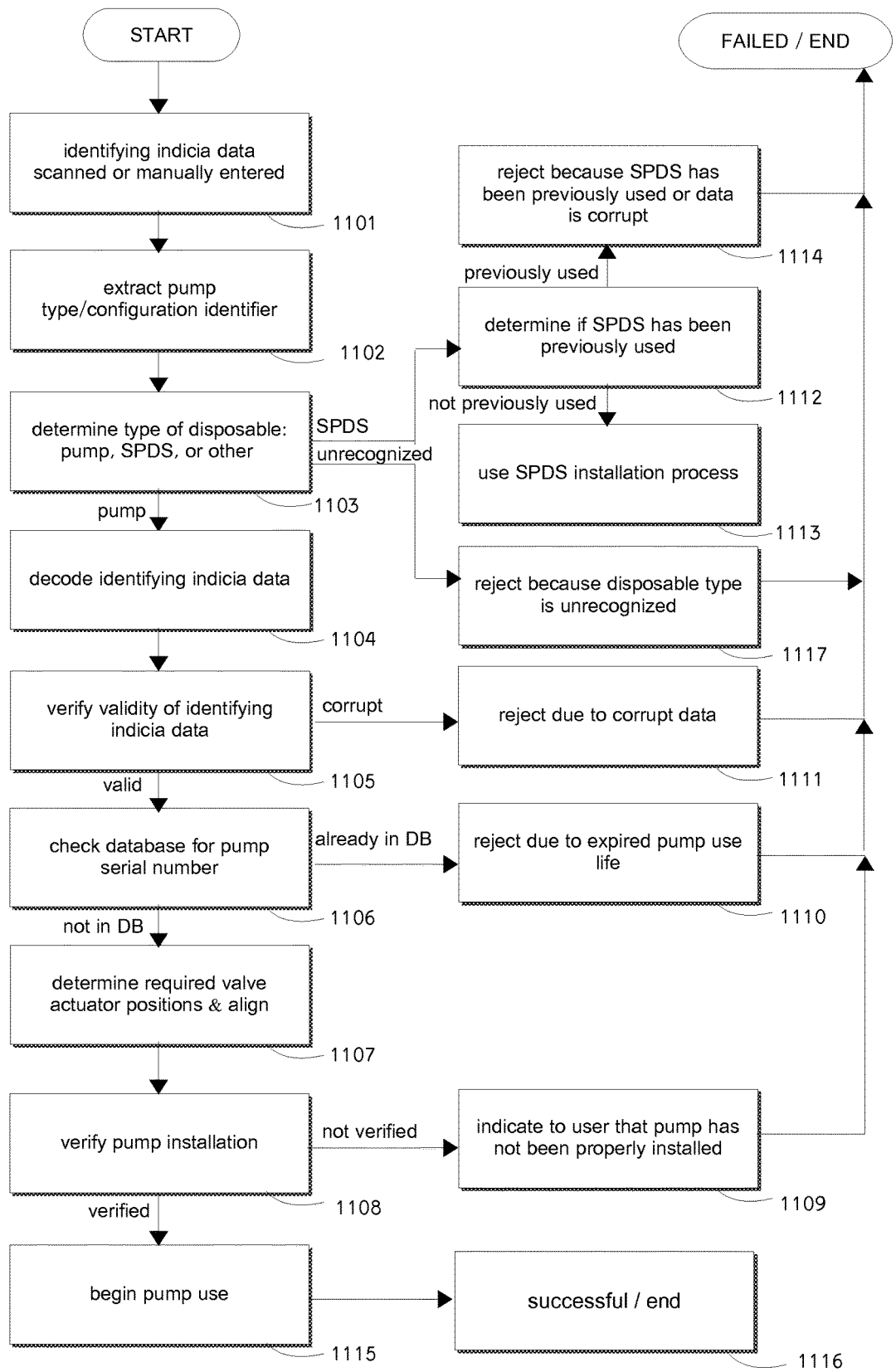
FIG. 36 is another flowchart for an exemplary process for installing and verifying the fluid pump device shown in FIG. 2 in a drive and actuating system which operates the fluid pump device.

Referring now to FIG. 36, a flowchart for the installation process of the pump 10 in the drive and actuating system (not shown) is presented. In a preferred but non-limiting embodiment, this process occurs when the pump 10 is installed in the drive and actuating system (not shown but described in U.S. Provisional Application No. 61/537,371 incorporated previously by reference in its entirety). The first installation step 1101 involves inputting the final string of characters (represented by the identifying indicia 172) into the control system (not shown but also described in U.S. Provisional Application No. 61/537,371 incorporated previously by reference in its entirety) that is provided to control operation of the various components of the drive and actuating system. This step may be done using a barcode or other indicia scanner, or may be inputted manually through an input device 1036.

In a second step 1102, at least a portion of the string may be used to identify the type of pump 10 and its specific configuration (e.g., the pump configuration/type number 1021). Since this information may not actually be encoded, the type of pump 10 may be determined without any additional decoding steps. In one embodiment, the first character may identify the type of cartridge and the second character may identify the configuration. For example, at step 1103, it may be determined that the pump 10 is in a "basic" configuration, as shown in FIG. 25. If the identifier does not indicate a compatible pump 10, or if the type or configuration is otherwise unrecognized, an error message may be generated and reported to the user through a suitable display at step 1117. If the identifier indicates a non-pump device, an alternative installation process may be initiated at steps 1112, 1113, 1114. For example, at step 1112, it may be determined whether the single-patient disposable supply set ("SPDS") connected to the installed pump may be used with the fluid delivery system 2. If the connected SPDS has not been previously used, a suggested installation process may be followed at step 1113. Alternatively, if the connected SPDS has been previously used, the installed pump may be rejected at step 1114 for being previously used or for having corrupt indicia data (e.g., the checksum does not match the encoded data, or the data cannot otherwise be processed).

If the pump 10 is compatible, as a next step 1104, a computing device connected to or integrated with the control system associated with the drive and actuating system decodes the string of characters to identify all of the original input parameters in the identifying indicia 172 (e.g., the pump configuration/type number 1021, manufacturing batch number 1022, pump sequential identification number 1023, and pump inlet selector valve position number 1024. The decoding process may involve an algorithm that reverses the steps used to encode the various parameters, or may utilize any other decoding algorithm capable of obtaining the various parameters from the encoded data.

Once the input parameters are identified, the computing device associated with the control system may then be used to confirm that the decoded data is valid at step 1105. Step 1105 may be performed by verifying that each of the decoded input parameters in the identifying indicia 172 (e.g., the pump configuration/type number 1021, manufacturing batch number 1022, pump sequential identification number 1023, and pump inlet selector valve position number 1024) are within an expected range for each. If the decoded data is invalid, the installed pump 10 is rejected at step 1111 for being associated with corrupt data. Further, the decoded data may also be confirmed with the checksum 1070 value of the decoded input parameters, which may be recalculated to confirm that the recalculated value matches the decoded checksum 1070 value. If any of these confirmation steps indicate that the decoded parameters are invalid, the installation process may be ended due to corrupt indicia data (at step 1111). An error message may be generated and communicated to a user, indicating the reason(s) that the installation failed.

At step 1106, once the input parameters are verified, the pump configuration/type number 1021 (e.g., a serial number) is compared with an internally-stored or remotely-stored list of used or otherwise expired pumps 10. It will be appreciated that this list may be stored in any type of data structure, such as a database. If a match is found, it may be determined that the pump 10 has been previously used, or is otherwise indicated to be expired, and the pump installation process may be ended due to expired pump use life (step 1110). An error message may be generated and communicated to a user indicating the reason(s) that the installation failed.

At the next step, step 1107, once it is determined that the pump 10 has not been previously used or used less than a maximum number of times (e.g., the serial number) has been accepted), the required inlet selector valve actuator positions are determined for the drive and actuating system. The pump inlet selector valve position number 1024 that was extracted from the identifying indicia 172 may be used in conjunction with a look-up table or conversion chart to determine the angular position for each inlet selector valve stem 306. The angular position of the inlet selector valve actuators are then adjusted in the drive and actuating system to align with the expected angular position for each inlet selector valve stem 306, and this will reposition these actuators while a user is installing the pump 10.

Once it is confirmed at step 1108 that the pump 10 has been properly installed and clamped within the drive and actuating system, normal use of the pump 10 may begin. If the inlet selector valve stems 306 are not in their expected positions, it may not be physically possible for the operator to install the pump 10 in the drive and actuating system, and the pump 10 therefore cannot be used with the fluid delivery system 2. At step 1109, an error message may be generated to alert the user that the pump 10 was not installed properly, and the installation process is ended. If the pump installation is verified, use of the pump may begin at step 1115, and the method may end successfully at step 1116.

Figure 37:
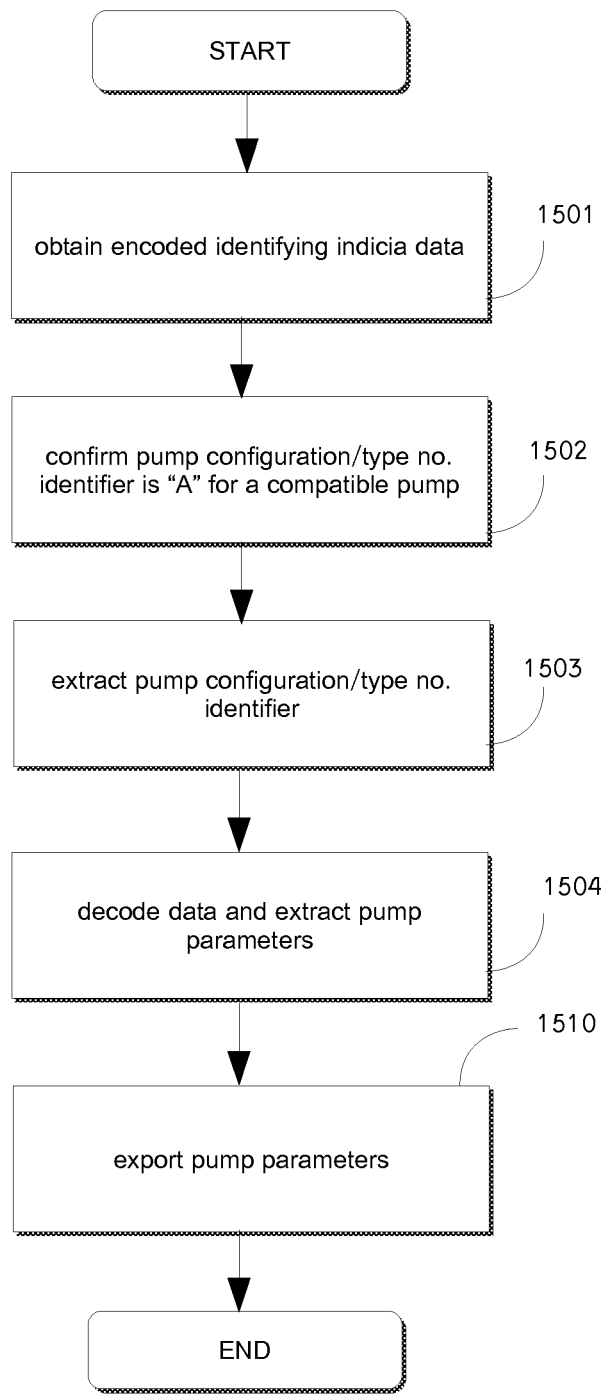
FIG. 37 is a flowchart of an exemplary decoding process for extracting specific features or input parameters associated with the fluid pump device shown in FIG. 2.

FIG. 37 shows a flowchart for the decoding process described above, which essentially reverses the encoding process depicted in FIG. 33. However, it will be appreciated that the decoding process may not necessarily reverse the encoding process, and that numerous decoding methods are possible. First, the encoded data is obtained at step 1501 and the pump configuration/type number 1021 is confirmed at step 1502. After extracting the pump configuration/type number 1021 at step 1503, the control system decodes the data using a decoding algorithm as already explained and extracts the pump parameters from the decoded data at step 1504. As described herein, any number of decoding methods and/or algorithms may be used. In one example, the decoding algorithm utilizes a public key 1060, residing on the on-board software of a fluid delivery system 2 or otherwise in possession of an end-user, which is generated according to the method shown in FIG. 34. The public key 1060 decodes data that is encoded with the private key 1050 that is also generated according to the method shown in FIG. 34. After the data is decoded, the pump parameters are exported from the decoded data at step 1510 for use by the fluid delivery system 2 and/or an end-user of the pump 10.

Figure 38:
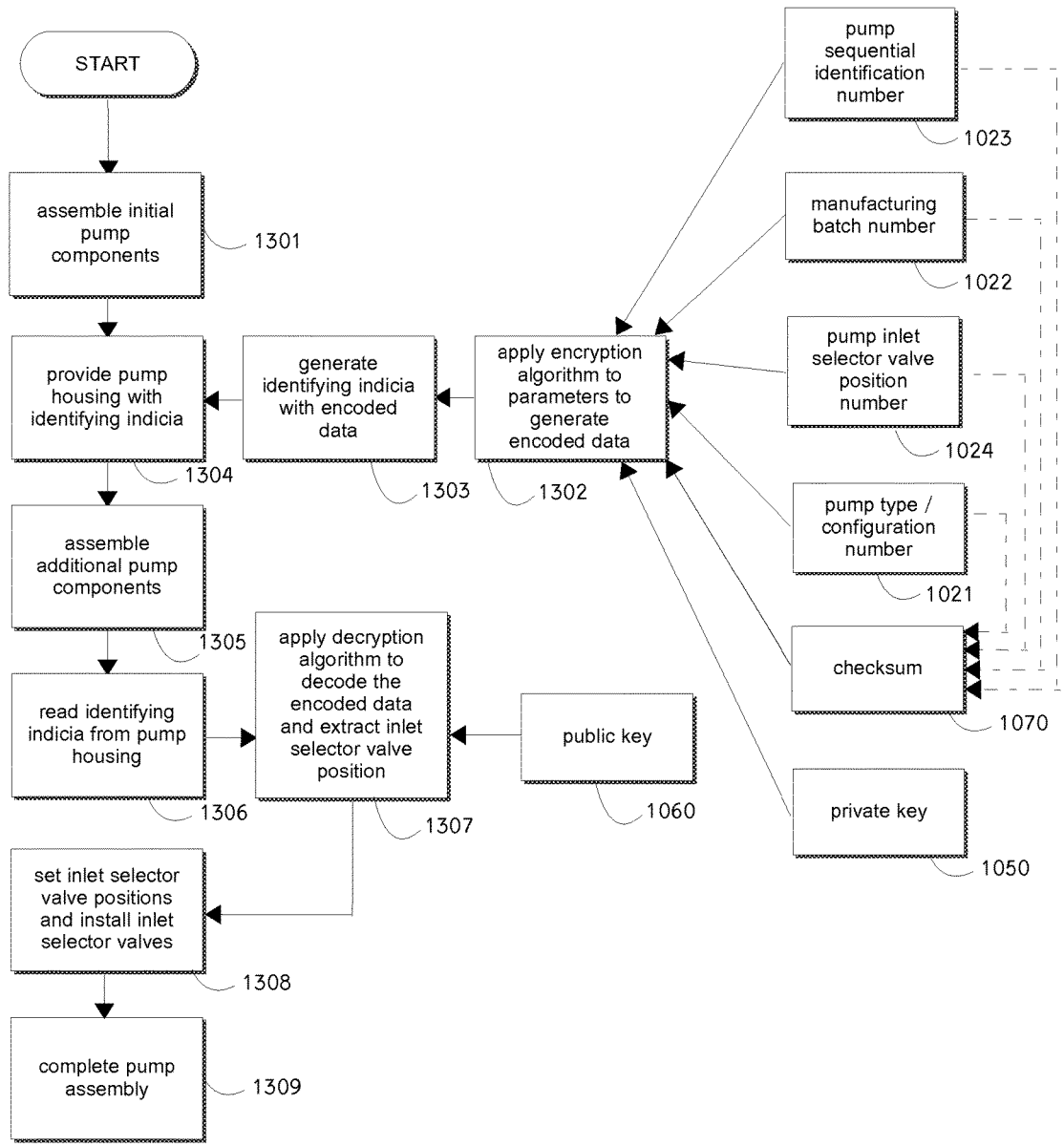
FIG. 38 is a flowchart of an exemplary assembly process for the fluid pump device shown in FIG. 2 using asymmetrical keys.

FIG. 38 shows a flowchart for an assembly process of a pump 10 utilizing a public-private encryption scheme. At a first step 1301, and as explained herein, the initial pump components are assembled (e.g., saline manifold cap 136, inlet and outlet check valves 194, 196, front manifold plate 230, inlet selector valves 300, pump cylinders 104, outlet selector valve cylinder 264, and the like). The pump parameters (e.g., the pump configuration/type number 1021, manufacturing batch number 1022, pump sequential identification number 1023, and pump inlet selector valve position number 1024) are used at step 1302 to generate a string of characters with an encoding algorithm. As already described, a private key 1050 may be used to encode the pump parameters. Next, at step 1303, identifying indicia is generated using the encoded string of characters using an indicia generating algorithm. This may include, for example, a matrix barcode. At step 1304, the pump 10 housing is provided with the identifying indicia. As an example, the identifying indicia may be laser-etched onto the pump 10 housing, or printed on a medium that is affixed to the pump 10 housing. At step 1305, any additional components that were not assembled in step 1301 may be assembled. Next, at step 1306, the identifying indicia is read by a manufacturing process computer 1030 or other like device, and the inlet selector valve position number 1024 is extracted at step 1307 using a decoding process. As described herein, the decoding process may use a public key 1060. Once one or more inlet selector valve position numbers 1024 are extracted from the encoded data, the inlet selector valves are set to a corresponding position at step 1308. It will be appreciated that the inlet selector valves may be set manually, or may be set with an automated insertion device 1040. Finally, at step 1309, the assembly process is completed and any final components are assembled.

While embodiments of a fluid delivery system including a fluid pumping device, optionally provided as a disposable pump cassette, and methods of use and operation thereof were provided in the foregoing description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A method of assembling a fluid pump device, the method comprising:
   providing a pump body comprising:
   a plurality of pump cylinders; and
   at least one inlet selector valve cylinder laterally outboard of the plurality of pump cylinders;
   inserting an inlet selector valve stem into the at least one inlet selector valve cylinder such that the inlet selector valve stem is in a predetermined angular orientation in the at least one inlet selector valve cylinder;
   inserting respective plungers into the plurality of pump cylinders;
   generating an inlet selector valve position number; and
   encoding the inlet selector valve position number as identifying indicia provided on the pump body,
   wherein the inlet selector valve position number corresponds to an angular position of the inlet selector valve stem, and
   wherein the identifying indicia is configured for being decoded to orient a drive mechanism based on the inlet selector valve position number.

2. The method of claim 1, wherein the pump body further comprises a saline manifold extending across the plurality of pump cylinders and defining at least one saline channel, and wherein the method further comprises installing a saline manifold cap onto the pump body to enclose the at least one saline channel.

3. The method of claim 1, wherein the pump body comprises a front plate and the plurality of pump cylinders extend proximally from the front plate, and wherein the method further comprises installing a manifold plate onto the front plate to form a pump manifold.

4. The method of claim 3, further comprising installing at least one check valve between the manifold plate and the front plate during the step of installing the manifold plate onto the front plate to form the pump manifold.

5. The method of claim 3, wherein the front plate comprises at least one inlet manifold channel defined by at least one channel member, and wherein the method further comprises installing an inlet manifold cap on the at least one channel member to enclose the at least one inlet manifold channel.

6. The method of claim 3, wherein the manifold plate comprises an outlet selector valve cylinder, and wherein the method further comprises inserting an outlet selector valve stem into the outlet selector valve cylinder.

7. The method of claim 6, wherein the outlet selector valve cylinder comprises a patient outlet port and a waste outlet port and the outlet selector valve stem defines a flow passage, and wherein inserting the outlet selector valve stem into the outlet selector valve cylinder comprises aligning the flow passage to be in fluid communication with the waste outlet port.

8. The method of claim 6, wherein inserting the outlet selector valve stem into the outlet selector valve cylinder is preceded by spraying a lubricant onto an interior wall surface of the outlet selector valve cylinder.

9. The method of claim 1, further comprising spraying a lubricant onto an interior wall surface of the plurality of pump cylinders and onto an interior surface of the at least one inlet selector valve cylinder prior to inserting the inlet selector valve stem into the at least one inlet selector valve cylinder and inserting the respective plungers into the plurality of pump cylinders.

10. The method of claim 1, wherein inserting the inlet selector valve stem into the at least one inlet selector valve cylinder and inserting the respective plungers into the plurality of pump cylinders occur concurrently.

11. The method of claim 1, wherein the inlet selector valve position number corresponds to the predetermined angular orientation of the inlet selector valve stem in the at least one inlet selector valve cylinder.

12. The method of claim 1, further comprising determining an initial angular orientation of the inlet selector valve stem in the at least one inlet selector valve.

* * * * *

UNITED STATES PATENT AND TRADEMARK OFFICE
CERTIFICATE OF CORRECTION

PATENT NO. : 9,649,436 B2  
APPLICATION NO. : 14/346196  
DATED : May 16, 2017  
INVENTOR(S) : Capone et al.

Page 1 of 1

It is certified that error appears in the above-identified patent and that said Letters Patent is hereby corrected as shown below:

In the Specification  
    In Column 6, Line 32, delete "12-12" and insert -- 11B-11B --, therefor.  
    In Column 14, Line 45, delete "member 212." and insert -- member 210. --, therefor.  
    In Column 18, Line 60, delete "plate 100" and insert -- plate 102 --, therefor.  
    In Column 21, Line 58, delete "Si" and insert -- S1 --, therefor.  
    In Column 24, Line 49, delete "tubes 32" and insert -- tubes 34 --, therefor.  
    In Column 25, Line 20, delete "tubes 32" and insert -- tubes 34 --, therefor.

Signed and Sealed this  
Twenty-sixth Day of September, 2017

Joseph Matal  
*Performing the Functions and Duties of the*  
*Under Secretary of Commerce for Intellectual Property and*  
*Director of the United States Patent and Trademark Office*